United States Patent
Hamanaka et al.

(10) Patent No.: US 6,974,813 B2
(45) Date of Patent: Dec. 13, 2005

(54) N-[(SUBSTITUTED FIVE-MEMBERED DI-OR TRIAZA DIUNSATURATED RING) CARBONYL] GUANIDINE DERIVATIVES FOR THE TREATMENT OF ISCHEMIA

(75) Inventors: Ernest S. Hamanaka, Gales Ferry, CT (US); Angel Guzman-Perez, Stonington, CT (US); Christian J. Mularski, Chester, CT (US); Roger B. Ruggeri, Waterford, CT (US); Ronald T. Wester, Ledyard, CT (US)

(73) Assignee: Warner-Lambert Company, Morris Plains, NJ (US)

( * ) Notice: Subject to any disclaimer, the term of this patent is extended or adjusted under 35 U.S.C. 154(b) by 137 days.

(21) Appl. No.: 10/315,369

(22) Filed: Dec. 9, 2002

(65) Prior Publication Data

US 2003/0149043 A1 Aug. 7, 2003

Related U.S. Application Data

(62) Division of application No. 09/367,731, filed on Aug. 18, 1999, now Pat. No. 6,492,401.

(30) Foreign Application Priority Data

Feb. 5, 1999 (WO) ............................... PCT/IB99/00206

(51) Int. Cl.$^7$ ...................... A61K 31/495; A61K 31/44; A61K 31/415; C07D 401/00; C07D 215/02
(52) U.S. Cl. ...................... 514/248; 514/341; 514/406; 544/238; 546/166; 546/275.7; 548/374.1
(58) Field of Search .................... 544/238; 514/248, 514/341, 406, 359; 546/166, 275.7; 548/374.1, 362.2, 255, 306.1, 262.2

(56) References Cited

U.S. PATENT DOCUMENTS

| 5,698,581 A | 12/1997 | Kleemann et al. ........... 514/447 |
| 5,852,046 A | 12/1998 | Lang et al. .................. 514/419 |
| 6,492,401 B1 * | 12/2002 | Hamanaka et al. .......... 514/359 |

FOREIGN PATENT DOCUMENTS

| DE | 2144568 | 9/1970 | ............ C07D/49/18 |
| EP | 0708091 | 4/1996 | ......... C07D/209/42 |
| EP | 0787728 | 8/1997 | ......... C07D/471/06 |
| EP | 0622356 | 7/1998 | ......... C07D/209/42 |
| EP | 0803501 | 7/2000 | ......... C07D/209/90 |
| WO | WO 9426709 | 11/1994 | ......... C07D/207/32 |
| WO | WO 9827061 | 6/1998 | ......... C07D/231/14 |

OTHER PUBLICATIONS

Takasaki, Koichiro, et al. 69: pp 977–994. 1973 "Hypoglycemic Activity of Certain Heterocyclic Acid Derivatives", Nichi–Yakuri–shi (Folia pharmacol. Japan).

* cited by examiner

*Primary Examiner*—Cecilia J. Tsang
*Assistant Examiner*—Binta Robinson
(74) *Attorney, Agent, or Firm*—Steven R. Eck; Charles W. Ashbrook

(57) ABSTRACT

NHE-1 inhibitors, methods of using such NHE-1 inhibitors and pharmaceutical compositions containing such NHE-1 inhibitors. The NHE-1 inhibitors are useful for the reduction of tissue damage resulting from tissue ischemia.

6 Claims, No Drawings

N-[(SUBSTITUTED FIVE-MEMBERED DI-OR TRIAZA DIUNSATURATED RING) CARBONYL] GUANIDINE DERIVATIVES FOR THE TREATMENT OF ISCHEMIA

This application is a divisional of U.S. application Ser. No. 09/367,731 filed under 35 U.S.C. section 371 on Aug. 18, 1999 now U.S. Pat. No. 6,492,401 based on PCT/IB99/00206 which was filed Feb. 5, 1999 which claims priority from U.S. provisional application Ser. No. 60/076,362 filed Feb. 27, 1998.

BACKGROUND OF INVENTION

This invention relates to sodium-hydrogen exchanger type 1 (NHE-1) inhibitors, pharmaceutical compositions containing such inhibitors and the use of such inhibitors to treat for example, ischemia particularly, perioperative myocardial ischemic injury in mammals, including humans.

Mycardial ischemic injury can occur in out-patient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and reduce hospitalizations, enhance quality of life and reduce overall health care costs of high risk patients.

Pharmacological cardioprotection would reduce the incidence and progression of myocardial infarction and dysfunction occurring in these surgical settings (perioperatively). In addition to reducing myocardial damage and improving post-ischemic myocardial function in patients with ischemic heart disease, cardioprotection would also decrease the incidence of cardiac morbidity and mortality due to myocardial infarction and dysfunction in patients "at risk" (such as greater than 65 years, exercise intolerant, coronary artery disease, diabetes mellitus, hypertension) that require non-cardiac surgery.

The mechanism(s) responsible for the myocardial injury observed after ischemia and reperfusion is not fully understood.

A variety of publications have disclosed the use of guanidine derivatives as useful for the treatment of, for example arrhythmias.

U.S. Pat. No. 5,698,581, granted Dec. 16, 1997 (EP 676395 A2 published 1995), discloses certain substituted N-heteroarylguanidines as inhibitors of the (Na+/H+) exchange transport system useful for the treatment of, for example, arrhythmias.

EP 803 501 A1, published Oct. 10, 1997, discloses substituted guanidine derivatives useful as (Na+/H+) exchange inhibitors.

WO 94/26709 discloses guanidine derivatives as inhibitors of (Na+/H+) exchange in cells.

PCT/JP97/04650 application published on Jun. 25, 1998 discloses N-[(substituted five-membered heteroaryl) carbonyl]guanidine compounds which are stated to be useful as inhibitors of $Na^+/H^+$ exchange and consequently effective for the treatment of various diseases such as hypertension, arrhythmia, angina pectoris, myocardial infarct, arteriosclerosis, and complications of diabetes.

Thus, there is clearly a need and a continuing search in this field of art for treatments for perioperative myocardial ischemia.

SUMMARY OF THE INVENTION

This invention is directed to a compound of Formula I

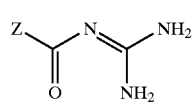

Formula I a prodrug thereof, or a pharmaceutically acceptable salt of said compound or of said prodrug wherein Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$) cycloalkyl optionally mono-or di-substituted independently with hydroxy, ($C_1$–$C_4$)alkoxy, ($C_1$–$C_4$)alklthio, ($C_1$–$C_4$) alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$)alkoxy, ($C_1$–$C_4$) alkoxycarbonyl, ($C_1$–$C_4$)alkyl, formyl, ($C_1$–$C_4$)alkanoyl, ($C_1$–$C_4$)alkanoyloxy, ($C_1$–$C_4$)alkanoylamino, ($C_1$–$C_4$) alkoxycarbonylamino, sulfonamido, ($C_1$–$C_4$) alkylsulfonamido, amino, mono-N- or di-N,N-($C_1$–$C_4$) alkylamino, carbamoyl, mono-N- or di-N,N-($C_1$–$C_4$) alkylcarbamoyl, cyano, thiol, ($C_1$–$C_4$)alkylthio, ($C_1$–$C_4$) alkylsulfinyl, ($C_1$–$C_4$)alkylsulfonyl, mono-N- or di-N,N-($C_1$–$C_4$)alkylaminosulfonyl, ($C_2$–$C_4$)alkenyl, ($C_2$–$C_4$) alkynyl or ($C_5$–$C_7$)cycloalkenyl, wherein said ($C_1$–$C_4$)alkoxy, ($C_1$–$C_4$)alkyl, ($C_1$–$C_7$) alkanoyl, ($C_1$–$C_4$)alkylthio, mono-N- or di-N,N-($C_1$–$C_4$) alkylamino or ($C_3$–$C_7$)cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$–$C_4$)alkanoylamino, ($C_1$–$C_4$) alkanoyloxy, ($C_1$–$C_4$)alkoxycarbonylamino, sulfonamido, ($C_1$–$C_4$)alkylsulfonamido, amino, mono-N- or di-N,N-

($C_1$–$C_4$)alkylamino, carbamoyl, mono-N- or di-N,N-($C_1$–$C_4$)alkylcarbamoyl, cyano, thiol, nitro, ($C_1$–$C_4$)alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines.

A preferred group of compounds, designated the A group, contains those compounds having the Formula I as shown above wherein Z is

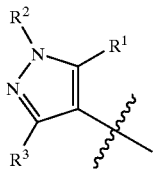

$R^1$ and $R^3$ are each independently hydrogen, ($C_1$–$C_4$)alkyl, ($C_3$–$C_7$)cycloalkyl, phenyl or phenyl($C_1$–$C_4$)alkyl, said ($C_1$–$C_4$)alkyl optionally substituted with from one to nine fluorines, said $R^1$ and $R^3$ substituents optionally mono- or di-substituted independently with hydroxy, ($C_1$–$C_4$) alkoxy, ($C_1$–$C_4$)alkylthio, ($C_1$–$C_4$)alkylsulfinyl or ($C_1$–$C_4$)alkylsulfonyl; and $R^2$ is unsubstituted ($C_1$–$C_4$)alkyl or ($C_3$–$C_7$)cycloalkyl; or $R^2$ is phenyl, phenyl($C_1$–$C_4$)alkyl, pyridyl or pyrimidinyl or a bicyclic ring consisting of two fused five and/or six membered rings taken independently optionally having one to four heteroatoms selected independently from nitrogen, sulfur and oxygen, said $R^2$ substituent optionally mono-, di- or tri-substituted independently with halo, ($C_1$–$C_4$)alkyl, ($C_1$–$C_4$)alkoxy, hydroxy, ($C_1$–$C_4$) alkoxycarbonyl, mono-N- or di-N,N-($C_1$–$C_4$) alkylcarbamoyl, mono-N- or di-N,N-($C_1$–$C_4$)alkylamino, ($C_1$–$C_4$)alkylsulfonyl or sulfonamido, said ($C_1$–$C_4$)alkyl or ($C_1$–$C_4$)alkoxy optionally substituted with from one to nine fluorines or the pharmaceutically acceptable salts thereof.

A group of compounds which is preferred among the A Group of compounds designated the B Group, contains those compounds wherein
$R^1$ is ($C_1$–$C_4$)alkyl or ($C_3$–$C_7$)cycloalkyl;
$R^2$ is phenyl, optionally mono- or di-substituted; and
$R^3$ is hydrogen or the pharmaceutically acceptable salts thereof.

Especially preferred compounds of Formula I are the compounds
[1-(2-chlorophenyl)-5-methyl-1H-pyrazole-4-carbonyl] guanidine;
[5-methyl-1-(2-trifluoromethylphenyl)-1H-pyrazole-4-carbonyl]guanidine;
[5-ethyl-1-phenyl-1H-pyrazole-4-carbonyl]guanidine;
[5-cyclopropyl-1-(2-trifluoromethylphenyl)-1H-pyrazole-4-carbonyl]guanidine;
[5-cyclopropyl-1-phenyl-1H-pyrazole-4-carbonyl] guanidine;
[5-cyclopropyl-1-(2,6-dichlorophenyl)-1H-pyrazole-4-carbonyl]guanidine and the pharmaceutically acceptable salts thereof.

Especially preferred compounds within the B Group of compounds are compounds wherein
a. $R^2$ is 2-chlorophenyl; and $R^1$ is methyl;
b. $R^2$ is 2-trifluoromethylphenyl; and $R^1$ is methyl;
c. $R^2$ is phenyl; and $R^1$ is ethyl;
d. $R^2$ is 2-trifluoromethylphenyl; and $R^1$ is cyclopropyl;
e. $R^2$ is phenyl; and $R^1$ is cyclopropyl; and
f. $R^2$ is 2,6-dichlorophenyl; and $R^1$ is cyclopropyl or the pharmaceutically acceptable salts thereof.

A group of compounds which is preferred among the A Group of compounds designated the C Group, contains those compounds wherein
$R^1$ is ($C_1$–$C_4$)alkyl or ($C_3$–$C_7$)cycloalkyl;
$R^2$ is naphthalenyl, quinolinyl, isoquinolinyl, cinnolinyl, phthalazinyl, quinoxalinyl, quinazolinyl, benzopyranyl, benzothiophenyl, benzodioxanyl or benzodioxolyl, said $R^2$ substituent optionally mono-substituted; and
$R^3$ is hydrogen or the pharmaceutically acceptable salts thereof.

Especially preferred compounds of Formula I are the compounds
[5-methyl-1-(quinolin-6-yl)-1H-pyrazole-4-carbonyl] guanidine;
[5-methyl-1-(naphthalen-1-yl)-1H-pyrazole-4-carbonyl] guanidine;
[5-cyclopropyl-1-(quinolin-5-yl)-1H-pyrazole-4-carbonyl] guanidine;
[5-cyclopropyl-1-(quinolin-8-yl)-1H-pyrazole-4-carbonyl] guanidine and the pharmaceutically acceptable salts thereof.

Especially preferred compounds within the C Group of compounds are compounds wherein
a. $R^2$ is 1-naphthalenyl; and $R^1$ is methyl;
b. $R^2$ is 5-quinolinyl; and $R^1$ is cyclopropyl;
c. $R^2$ is 8-quinolinyl; and $R^1$ is cyclopropyl; and
d. $R^2$ is 6-quinolinyl; and $R^1$ is methyl or the pharmaceutically acceptable salts thereof.

A group of compounds which is preferred among the A Group of compounds, designated the D Group, contains those compounds wherein
$R^1$ is hydrogen;
$R^2$ is phenyl, optionally mono- or di-substituted; and
$R^3$ is ($C_1$–$C_4$)alkyl or ($C_3$–$C_7$)cycloalkyl or the pharmaceutically acceptable salts thereof.

Especially preferred compounds of Formula I are the compounds
[3-methyl-1-phenyl-1H-pyrazole-4-carbonyl]guanidine;
[3-methyl-1-(naphthalen-1-yl)-1H-pyrazole-4-carbonyl] guanidine;
[3-methyl-1-(isoquinolin-5-yl)-1H-pyrazole-4-carbonyl] guanidine and the pharmaceutically acceptable salts thereof.

An especially preferred compound within the D Group of compounds is the compound wherein
$R^2$ is phenyl; and
$R^3$ is methyl or the pharmaceutically acceptable salts thereof.

A group of compounds which is preferred among the A Group of compounds, designated the E Group, contains those compounds wherein
$R^1$ is hydrogen;
$R^2$ is naphthalenyl, quinolinyl, isoquinolinyl, cinnolinyl, phthalazinyl, quinoxalinyl, quinazolinyl, benzopyranyl, benzothiophenyl, benzodioxanyl or benzodioxolyl, said $R^2$ substituent optionally mono-substituted; and
$R^3$ is ($C_1$–$C_4$)alkyl or ($C_3$–$C_7$)cycloalkyl or the pharmaceutically acceptable salts thereof.

Especially preferred compounds within the E Group of compounds are compounds wherein
a. $R^2$ is 1-naphthalenyl; and $R^3$ is methyl; and
b. $R^2$ is 5-isoquinolyl; and $R^3$ is methyl or the pharmaceutically acceptable salts thereof.

A preferred group of compounds, designated the F Group, contains those compounds having the Formula I as shown above wherein Z is

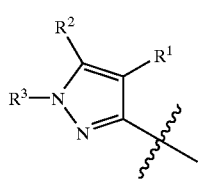

$R^1$ is hydrogen, $(C_1–C_4)$alkyl, $(C_3–C_7)$cycloalkyl, phenyl or phenyl$(C_1–C_4)$alkyl, said $(C_1–C_4)$alkyl optionally substituted with from one to nine fluorines, said $R^1$ substituents optionally mono- or di-substituted independently with hydroxy, $(C_1–C_4)$alkoxy, $(C_1–C_4)$alkylthio, $(C_1–C_4)$alkylsulfinyl or $(C_1–C_4)$alkylsulfonyl; and $R^2$ and $R^3$ are each independently unsubstituted $(C_1–C_4)$alkyl or $(C_3–C_7)$cycloalkyl; or $R^2$ and $R^3$ are each independently phenyl or phenyl$(C_1–C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^2$ and $R^3$ substituents optionally mono-, di- or tri-substituted independently with halo, $(C_1–C_4)$alkyl, $(C_1–C_4)$alkoxy, hydroxy, trifluoromethoxy, $(C_1–C_4)$alkoxycarbonyl, mono-N- or di-N,N-$(C_1–C_4)$alkylcarbamoyl, mono-N- or di-N,N-$(C_1–C_4)$alkylamino, $(C_1–C_4)$alkylsulfonyl or sulfonamido, said $(C_1–C_4)$alkyl or $(C_1–C_4)$alkoxy optionally substituted with from one to nine fluorines or the pharmaceutically acceptable salts thereof.

An especially preferred compound of Formula I is [4-methyl-1-phenyl-1H-pyrazole-3-carbonyl]guanidine and a pharmaceutically acceptable salt thereof.

An especially preferred compound within the F Group of compounds is a compound wherein
$R^3$ is phenyl;
$R^1$ is methyl; and
$R^2$ is H or the pharmaceutically acceptable salts thereof.

A preferred group of compounds, designated the G Group, contains those compounds having the Formula I as shown above wherein Z is

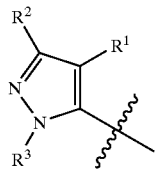

$R^1$ and $R^3$ are each independently hydrogen, $(C_1–C_4)$alkyl, $(C_3–C_7)$cycloalkyl, phenyl or phenyl$(C_1–C_4)$alkyl, said $(C_1–C_4)$alkyl optionally substituted with from one to nine fluorines, said $R^1$ and $R^3$ substituents optionally mono- or di-substituted independently with hydroxy, $(C_1–C_4)$alkoxy, $(C_1–C_4)$alkylthio, $(C_1–C_4)$alkylsulfinyl or $(C_1–C_4)$alkylsulfonyl; and $R^2$ is unsubstituted $(C_1–C_4)$alkyl or $(C_3–C_7)$cycloalkyl; or $R^2$ is phenyl, phenyl$(C_1–C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^2$ substituent optionally mono-, di- or tri-substituted independently with halo, $(C_1–C_4)$alkyl, $(C_1–C_4)$alkoxy, hydroxy, $(C_1–C_4)$alkoxycarbonyl, mono-N- or di-N,N-$(C_1–C_4)$alkylcarbamoyl, mono-N- or di-N,N-$(C_1–C_4)$alkylamino, $(C_1–C_4)$alkylsulfonyl or sulfonamido, said $(C_1–C_4)$alkyl or $(C_1–C_4)$alkoxy optionally substituted with from one to nine fluorines or the pharmaceutically acceptable salts thereof.

A group of compounds which is preferred among the G Group of compounds, designated the H Group, contains those compounds wherein
$R^1$ is $(C_1–C_4)$alkyl or $(C_3–C_7)$cycloalkyl;
$R^2$ is phenyl, optionally mono- or di-substituted; and
$R^3$ is hydrogen or the pharmaceutically acceptable salts thereof.

A group of compounds which is preferred among the G Group of compounds, designated the I Group, contains those compounds wherein
$R^1$ is $(C_1–C_4)$alkyl or $(C_3–C_7)$cycloalkyl;
$R^2$ is naphthalenyl, quinolinyl, isoquinolinyl, cinnolinyl, phthalazinyl, quinoxalinyl, quinazolinyl, benzopyranyl, benzothiophenyl, benzodioxanyl or benzodioxolyl, said $R^2$ substituent optionally mono-substituted; and
$R^3$ is hydrogen.

A group of compounds which is preferred among the G Group of compounds, designated the J Group, contains those compounds wherein
$R^1$ is hydrogen;
$R^2$ is phenyl, optionally mono- or di-substituted; and
$R^3$ is $(C_1–C_4)$alkyl or $(C_3–C_7)$cycloalkyl.

Especially preferred compounds of Formula I are the compounds
[2-methyl-5-phenyl-2H-pyrazole-3-carbonyl]guanidine;
[2-methyl-5-(naphthalen-1-yl)-2H-pyrazole-3-carbonyl]guanidine and the pharmaceutically acceptable salts thereof.

An especially preferred compound within the J Group of compounds is the compound wherein
$R^2$ is phenyl; and
$R^3$ is methyl or the pharmaceutically acceptable salts thereof.

A group of compounds which is preferred among the G Group of compounds, designated the K Group, contains those compounds wherein
$R^1$ is hydrogen;
$R^2$ is naphthalenyl, quinolinyl, isoquinolinyl, cinnolinyl, phthalazinyl, quinoxalinyl, quinazolinyl, benzopyranyl, benzothiophenyl, benzodioxanyl or benzodioxolyl, said $R^2$ substituent optionally mono-substituted; and
$R^3$ is $(C_1–C_4)$alkyl or $(C_3–C_7)$cycloalkyl or the pharmaceutically acceptable salts thereof.

An especially preferred compound within the K Group of compounds is the compound wherein
$R^2$ is 1-naphthalenyl; and
$R^3$ is methyl and the pharmaceutically acceptable salts thereof.

A preferred group of compounds, designated the L Group, contains those compounds having the Formula I as shown above wherein Z is

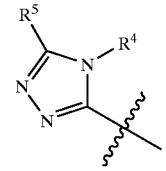

$R^4$ is hydrogen, $(C_1–C_4)$alkyl, $(C_3–C_7)$cycloalkyl, phenyl or phenyl$(C_1–C_4)$alkyl, said $(C_1–C_4)$alkyl optionally substituted with from one to nine fluorines, said $R^4$ substituent optionally mono- or di-substituted independently with hydroxy, $(C_1–C_4)$alkoxy, $(C_1–C_4)$alkylthio, $(C_1–C_4)$alkylsulfinyl or $(C_1–C_4)$alkylsulfonyl; and $R^5$ is unsubstituted $(C_1-C_4)$alkyl or $(C_3-C_7)$cycloalkyl; or $R^5$ is phenyl, phenyl$(C_1-C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^5$ substituent optionally mono-, di- or tri-substituted independently with halo, $(C_1-C_4)$alkyl, $(C_1-C_4)$alkoxy, hydroxy, $(C_1-C_4)$alkoxycarbonyl, mono-N- or di-N,N-$(C_1-C_4)$alkylcarbamoyl, mono-N- or di-N,N-$(C_1-C_4)$alkylamino, $(C_1-C_4)$alkylsulfonyl, or sulfonamido, said $(C_1-C_4)$alkyl or $(C_1-C_4)$alkoxy optionally substituted with from one to nine fluorines or the pharmaceutically acceptable salts thereof.

A preferred group of compounds, designated the M Group, contains those compounds having the Formula I as shown above wherein Z is

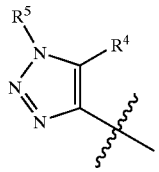

$R^4$ is hydrogen, $(C_1-C_4)$alkyl, $(C_3-C_7)$cycloalkyl, phenyl, phenyl$(C_1-C_4)$alkyl, said $(C_1-C_4)$alkyl optionally substituted with from one to nine fluorines, said $R^4$ substituent optionally mono- or di-substituted independently with hydroxy, $(C_1-C_4)$alkoxy, $(C_1-C_4)$alkylthio, $(C_1-C_4)$alkylsulfinyl or $(C_1-C_4)$alkylsulfonyl; and $R^5$ is unsubstituted $(C_1-C_4)$alkyl or $(C_3-C_7)$cycloalkyl; or $R^5$ is phenyl, phenyl$(C_1-C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^5$ substituent optionally mono-, di- or tri-substituted independently with halo, $(C_1-C_4)$alkyl, $(C_1-C_4)$alkoxy, hydroxy, $(C_1-C_4)$alkoxycarbonyl, mono-N- or di-N,N-$(C_1-C_4)$alkylcarbamoyl, mono-N- or di-N,N-$(C_1-C_4)$alkylamino, $(C_1-C_4)$alkylsulfonyl or sulfonamido, said $(C_1-C_4)$alkyl or $(C_1-C_4)$alkoxy optionally substituted with from one to nine fluorines or the pharmaceutically acceptable salts thereof.

A preferred group of compounds, designated the N Group, contains those compounds having the Formula I as shown above wherein Z is

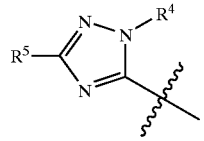

$R^4$ is hydrogen, $(C_1-C_4)$alkyl, $(C_3-C_7)$cycloalkyl, phenyl or phenyl$(C_1-C_4)$alkyl, said $(C_1-C_4)$alkyl optionally substituted with from one to nine fluorines, said $R^4$ substituent optionally mono- or di-substituted independently with hydroxy, $(C_1-C_4)$alkoxy, $(C_1-C_4)$alkylthio, $(C_1-C_4)$alkylsulfinyl or $(C_1-C_4)$alkylsulfonyl; and $R^5$ is unsubstituted $(C_1-C_4)$alkyl or $(C_3-C_7)$cycloalkyl; or $R^5$ is phenyl, phenyl$(C_1-C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^5$ substituent optionally mono-, di- or tri-substituted independently with halo, $(C_1-C_4)$alkyl, $(C_1-C_4)$alkoxy, hydroxy, $(C_1-C_4)$alkoxycarbonyl, mono-N- or di-N,N-$(C_1-C_4)$alkylcarbamoyl, mono-N- or di-N,N-$(C_1-C_4)$alkylamino, $(C_1-C_4)$alkylsulfonyl or sulfonamido, said $(C_1-C_4)$alkyl or $(C_1-C_4)$alkoxy optionally substituted with from one to nine fluorines or the pharmaceutically acceptable salts thereof.

A preferred group of compounds, designated the O Group, contains those compounds having the Formula I as shown above wherein Z is

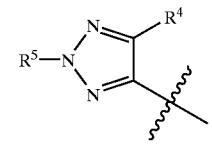

$R^4$ is hydrogen, $(C_1-C_4)$alkyl, $(C_3-C_7)$cycloalkyl, phenyl or phenyl$(C_1-C_4)$alkyl, said $(C_1-C_4)$alkyl optionally substituted with from one to nine fluorines, said $R^4$ substituent optionally mono- or di-substituted independently with hydroxy, $(C_1-C_4)$alkoxy, $(C_1-C_4)$alkylthio, $(C_1-C_4)$alkylsulfinyl or $(C_1-C_4)$alkylsulfonyl; and $R^5$ is unsubstituted $(C_1-C_4)$alkyl or $(C_3-C_7)$cycloalkyl; or $R^5$ is phenyl, phenyl$(C_1-C_4)$alkyl, pyridyl or pyrimidinyl or a bicyclic ring consisting of two fused five and/or six membered rings taken independently optionally having one to four heteroatoms selected independently from nitrogen, sulfur and oxygen, said $R^5$ substituent optionally mono-, di- or tri-substituted independently with halo, $(C_1-C_4)$alkyl, $(C_1-C_4)$alkoxy, hydroxy, $(C_1-C_4)$alkoxycarbonyl, mono-N- or di-N,N-$(C_1-C_4)$alkylcarbamoyl, mono-N- or di-N,N-$(C_1-C_4)$alkylamino, $(C_1-C_4)$alkylsulfonyl or sulfonamido, said $(C_1-C_4)$alkyl or $(C_1-C_4)$alkoxy optionally substituted with from one to nine fluorines or the pharmaceutically acceptable salts thereof.

A group of compounds which is preferred among the O Group of compounds designated the P Group, contains those compounds wherein $R^4$ is $(C_1-C_4)$alkyl or $(C_3-C_7)$cycloalkyl; and $R^5$ is phenyl, optionally mono- or di-substituted or the pharmaceutically acceptable salts thereof.

Especially preferred compounds of Formula I are the compounds

[5-methyl-2-phenyl-2H-1,2,3-triazole-4-carbonyl]guanidine;

[5-methyl-2-(3-methoxyphenyl)-2H-1,2,3-triazole-4-carbonyl]guanidine;

[2-(3-bromophenyl)-5-methyl-2H-1,2,3-triazole-4-carbonyl]guanidine and the pharmaceutically acceptable salts thereof.

Especially preferred compounds within the P Group of compounds are compounds wherein a. $R^5$ is phenyl; and $R^4$ is methyl;

b. $R^5$ is 3-methoxyphenyl; and $R^4$ is methyl; and c. $R^5$ is 3-bromophenyl; and $R^4$ is methyl or the pharmaceutically acceptable salts thereof.

A group of compounds which is preferred among the O Group of compounds, designated the Q Group, contains those compounds wherein $R^4$ is $(C_1-C_4)$alkyl or $(C_3-C_7)$cycloalkyl; and $R^5$ is naphthalenyl, quinolinyl, isoquinolinyl, cinnolinyl, phthalazinyl, quinoxalinyl, quinazolinyl, benzopyranyl, benzothiophenyl, benzodioxanyl or benzodioxolyl, said $R^5$ substituents optionally mono-substituted or the pharmaceutically acceptable salts thereof.

Especially preferred compounds of Formula I are the compounds

[2-(naphthalen-1-yl)-5-methyl-2H-1,2,3-triazole-4-carbonyl]guanidine;

[2-(isoquinolin-5-yl)-5-methyl-2H-1,2,3-triazole-4-carbonyl]guanidine;

[5-methyl-2-(quinolin-5-yl)-2H-1,2,3-triazole-4-carbonyl]guanidine and the pharmaceutically acceptable salts thereof.

Especially preferred compounds within the Q Group of compounds are compounds wherein a. $R^5$ is 1-naphthalenyl; and $R^4$ is methyl;
b. $R^5$ is 5-isoquinolinyl; and $R^4$ is methyl; and
c. $R^5$ is 5-quinolinyl; and $R^4$ is methyl or the pharmaceutically acceptable salts thereof.

Another aspect of this invention is directed to the following compounds:

5-Methyl-2-(5-quinolinyl)-2H-1,2,3-triazole-4-carboxylic acid,

5-Methyl-2-(5-isoquinolinyl)-2H-1,2,3-triazole-4-carboxylic acid, 2-(1-Naphtalenyl)-5-methyl-2H-1,2,3-triazole4-carboxylic acid, Ethyl 5-cyclopropyl-1-(2-trifluoromethylphenyl)-1H-pyrazole-4-carboxylate, Ethyl 5-methyl-1-(6-quinolinyl)-1H-pyrazole-4-carboxylate, Ethyl 5-methyl-1-naphthalenyl-1H-pyrazole-4-carboxylate, Ethyl 5-cyclopropyl-1-(quinolin-8-yl)-1H-pyrazole-4-carboxylate, Ethyl 5-cyclopropyl-1-(quinolin-5-yl)-1H-pyrazole-4-carboxylate, Methyl 5-ethyl-1-(quinolin-5-yl)-1H-pyrazole-4-carboxylate, n-Butyl 1-(isoquinolin-5-yl)-3-methyl-1H-pyrazole-4-carboxylate, 5-Methyl-1-(6-quinolinyl)-1H-pyrazole-4-carboxylic acid, 5-Methyl-1-naphthalenyl-1H-pyrazole-4-carboxylic acid, 5-Cyclopropyl-1-(quinolin-8-yl)-1H-pyrazole-4-carboxylic acid, 5-Cyclopropyl-1-(2-trifluoromethylphenyl)-1H-pyrazole-4-carboxylic acid, 5-Ethyl-1-(quinolin-5-yl)-1H-pyrazole-4-carboxylic acid, 5-Cyclopropyl-1-(quinolin-5-yl)-1H-pyrazole-4-carboxylic acid or 1-(Isoquinolin-5-yl)-3-methyl-1H-pyrazole-4-carboxylic acid or a pharmaceutically acceptable salt of said compound.

A preferred group of compounds designated the R group, contains those compounds having the Formula I as shown above wherein Z is

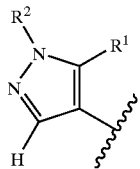

$R^1$ is $(C_3-C_7)$cycloalkyl, phenyl or phenyl$(C_1-C_4)$alkyl, said $(C_3-C_7)$cycloalkyl optionally substituted with from one to three fluorines, said $R^1$ substituent optionally mono- or di-substituted independently with $(C_1-C_4)$alkoxy, $(C_1-C_4)$alkylthio, $(C_1-C_4)$alkylsulfinyl or $(C_1-C_4)$alkylsulfonyl; and $R^2$ is $(C_1-C_4)$alkyl, $(C_3-C_4)$cycloalkyl, M or M$(C_1-C_4)$alkyl, any of said previous $(C_1-C_4)$alkyl moieties optionally having from one to nine fluorines; said $(C_1-C_4)$alkyl or $(C_3-C_4)$cycloalkyl optionally mono-or di-substituted independently with hydroxy, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkyl, mono-N- or di-N,N-$(C_1-C_4)$alkylcarbamoyl or mono-N- or di-N,N-$(C_1-C_4)$alkylaminosulfonyl; and said $(C_3-C_4)$cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_4)$alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines or the pharmaceutically acceptable salts thereof.

An especially preferred compound of Formula I is the compound

[1-(Naphthalen-1-yl)-5-cyclopropyl-1H-pyrazole-4-carbonyl]guanidine or the pharmaceutically acceptable salts thereof.

A group of compounds which is preferred among the R Group of compounds designated the S Group, contains those compounds wherein $R^1$ is cyclopropyl; and $R^2$ is 1-naphthalenyl or the pharmaceutically acceptable salts thereof.

A group of compounds which is preferred among the R Group of compounds designated the T Group, contains those compounds wherein $R^1$ is $(C_3-C_7)$cycloalkyl; and $R^2$ is a five to six membered monocyclic aromatic ring optionally having one to two heteroatoms selected independently from oxygen, sulfur and nitrogen;

said R² ring is optionally mono-substituted on carbon or nitrogen with a fully saturated or fully unsaturated five to six membered ring optionally having one to two heteroatoms selected independently from oxygen, sulfur and nitrogen, said ring optionally mono-substituted with $(C_1-C_4)$alkyl said R² ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino are optionally mono-substituted with hydroxy, $(C_1-C_4)$alkoxycarbonyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines or the pharmaceutically acceptable salts thereof.

A group of compounds which is preferred among the T Group of compounds designated the U Group, contains those compounds wherein R¹ is cyclopropyl; and R² is phenyl, optionally mono- or di-substituted independently with hydroxy, halo, $(C_1-C_4)$alkoxy, $(C_1-C_4)$alkoxycarbonyl, $(C_1-C_4)$alkyl, $(C_1-C_4)$alkanoylamino, $(C_1-C_4)$alkoxycarbonylamino, sulfonamido, $(C_1-C_4)$alkylsulfonamido, mono-N- or di-N,N-$(C_1-C_4)$alkylamino, carbamoyl, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl, wherein said $(C_1-C_4)$alkoxy, $(C_1-C_4)$alkyl, mono-N- or di-N,N-$(C_1-C_4)$alkylamino substituents are optionally mono-substituted with hydroxy, $(C_1-C_4)$alkanoylamino, $(C_1-C_4)$alkylsulfonamido, amino, mono-N- or di-N,N-$(C_1-C_4)$alkylamino, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl or optionally substituted with one to five fluorines;

or the pharmaceutically acceptable salts thereof.

Especially preferred compounds of Formula I are the compounds

[5-cyclopropyl-1-(2-trifluoromethylphenyl)-1H-pyrazole-4-carbonyl]guanidine;

[5-cyclopropyl-1-phenyl-1H-pyrazole-4-carbonyl]guanidine; or

[5-cyclopropyl-1-(2,6-dichlorophenyl)-1H-pyrazole-4-carbonyl]guanidine or the pharmaceutically acceptable salts of said compounds.

Other especially preferred compounds of Formula I are the compounds

[1-(2-Chloro-4-methylsulfonylphenyl)-5-cyclopropyl-1H-pyrazole-4-carbonyl]guanidine;

[1-(2-Chlorophenyl)-5-cyclopropyl-1H-pyrazole-4-carbonyl]guanidine;

[1-(2-Trifluoromethyl-4-fluorophenyl)-5-cyclopropyl-1H-pyrazole4-carbonyl]guanidine;

[1-(2-Bromophenyl)-5-cyclopropyl-1H-pyrazole-4-carbonyl]guanidine;

[1-(2-Fluorophenyl)-5-cyclopropyl-1H-pyrazole-4-carbonyl]guanidine;

[1-(2-Chloro-5-methoxyphenyl)-5-cyclopropyl-1H-pyrazole-4-carbonyl]guanidine;

[1-(2-Chloro-4-methylaminosulfonylphenyl)-5-cyclopropyl-1H-pyrazole-4-carbonyl]guanidine;

[1-(2,5-Dichlorophenyl)-5-cyclopropyl-1H-pyrazole-4-carbonyl]guanidine;

[1-(2,3-Dichlorophenyl)-5-cyclopropyl-1H-pyrazole-4-carbonyl]guanidine;

[1-(2-Chloro-5-aminocarbonylphenyl)-5-cyclopropyl-1H-pyrazole-4-carbonyl]guanidine;

[1-(2-Chloro-5-aminosulfonylphenyl)-5-cyclopropyl-1H-pyrazole-4-carbonyl]guanidine;

[1-(2-Fluoro-6-trifluoromethylphenyl)-5-cyclopropyl-1H-pyrazole-4-carbonyl]guanidine;

[1-(2-Chloro-5-methylsulfonylphenyl)-5-cyclopropyl-1H-pyrazole-4-carbonyl]guanidine;

[1-(2-Chloro-5-dimethylaminosulfonylphenyl)-5-cyclopropyl-1H-pyrazole-4-carbonyl]guanidine;

[1-(2-Trifluoromethyl-4-chlorophenyl)-5-cyclopropyl-1H-pyrazole-4-carbonyl]guanidine;

or pharmaceutically acceptable salts of said compounds.

Especially preferred compounds within the U Group are compounds wherein a. R² is 2-chloro-4-methylsulfonylphenyl;
b. R² is 2-chlorophenyl;
c. R² is 2-trifluoromethyl-4-fluorophenyl;
d. R² is 2-bromophenyl;
e. R² is 2-fluorophenyl;
f. R² is 2-chloro-5-methoxyphenyl;
g. R² is 2-chloro-4-methylaminosulfonylphenyl;
h. R² is 2,5-dichlorophenyl;
i. R² is 2,3-dichlorophenyl;
j. R² is 2-chloro-5-aminocarbonylphenyl;
k. R² is 2-chloro-5-aminosulfonylphenyl;
l. R² is 2-fluoro-6-trifluoromethylphenyl;
m. R² is 2-chloro-5-methylsulfonylphenyl;
n. R² is 2-chloro-5-dimethylaminosulfonylphenyl;
o. R² is 2-trifluoromethyl-4-chlorophenyl; or the pharmaceutically acceptable salts of said compounds.

A group of compounds which is preferred among the R Group of compounds designated the W Group, contains those compounds wherein R² is a five to six membered nonaromatic heterocyclic ring having one to two heteroatoms selected independently from nitrogen, sulfur and oxygen or R² is unsubstituted $(C_1-C_4)$alkyl, unsubstituted $(C_3-C_7)$cycloalkyl or phenyl $(C_1-C_4)$alkyl, wherein said phenyl$(C_1-C_4)$alkyl is optionally mono-or di-substituted independently with hydroxy, halo, $(C_1-C_4)$alkoxy, $(C_1-C_4)$alkoxycarbonyl, $(C_1-C_4)$alkyl, $(C_1-C_4)$alkanoylamino, $(C_1-C_4)$alkoxycarbonylamino, sulfonamido, $(C_1-C_4)$alkylsulfonamido, mono-N- or di-N,N-$(C_1-C_4)$alkylamino, carbamoyl, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl, wherein said $(C_1-C_4)$alkoxy, $(C_1-C_4)$alkyl, mono-N- or di-N,N-$(C_1-C_4)$alkylamino substituents are optionally mono-substituted with hydroxy, $(C_1-C_4)$alkanoylamino, $(C_1-C_4)$alkylsulfonamido, amino, mono-N- or di-N,N-$(C_1-C_4)$alkylamino, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl or optionally substituted with one to five fluorines;

or the pharmaceutically acceptable salts thereof.

A group of compounds which is preferred among the R Group of compounds designated the X Group, contains those compounds wherein $R^2$ is a bicyclic ring consisting of two fused five and/or six membered partially saturated, fully saturated or fully unsaturated rings taken independently having one to four heteroatoms selected independently from nitrogen, sulfur and oxygen, said $R^2$ substituent optionally substituted on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_4)$alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines, or the pharmaceutically acceptable salts thereof.

A group of compounds which is preferred among the X Group of compounds designated the Y Group, contains those compounds wherein $R^1$ is $(C_3-C_7)$cycloalkyl; and $R^2$ is a bicyclic ring consisting of two fused five and/or six membered partially saturated, fully saturated or fully unsaturated rings taken independently having one to three heteroatoms selected independently from nitrogen, sulfur and oxygen, said $R^2$ bicyclic ring is optionally mono-substituted on carbon or nitrogen with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ bicyclic ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N ,N-$(C_1-C_4)$alkylamino, carbamoyl, mono-N- or di-N, N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino are optionally mono-substituted with hydroxy, $(C_1-C_4)$alkoxycarbonyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines or the pharmaceutically acceptable salts thereof.

A group of compounds which is preferred among the Y Group of compounds designated the Z Group, contains those compounds wherein $R^1$ is cyclopropyl; and $R^2$ is a quinazolinyl, phthalazinyl, quinolinyl, isoquinolinyl, cinnolinyl, benzodioxanyl, quinoxalinyl, benzopyranyl, benzothiophenyl, benzodioxolyl, benzimidazolyl, indazolyl, indolyl, benzotriazolyl, benzoxazolyl, benzisoxazolyl, benzothiazolyl, benzisothiazolyl, benzoxadiazolyl or benzothiadiazolyl ring, wherein said $R^2$ bicyclic ring is optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoylamino, $(C_1-C_4)$alkoxycarbonylamino, sulfonamido, $(C_1-C_4)$alkylsulfonamido, mono-N- or di-N,N-$(C_1-C_4)$alkylamino, carbamoyl, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl, wherein said $(C_1-C_4)$alkoxy, $(C_1-C_4)$alkyl, mono-N- or di-N,N-$(C_1-C_4)$alkylamino substituents are optionally mono-substituted with hydroxy, $(C_1-C_4)$alkanoylamino, $(C_1-C_4)$alkylsulfonamido, amino, mono-N- or di-N,N-$(C_1-C_4)$alkylamino, mono-N- or di-N,N-$(C_1-C_4)$alkylcarbamoyl, $(C_1-C_4)$alkylsulfonyl or mono-N- or di-N, N-$(C_1-C_4)$alkylaminosulfonyl or optionally substituted with one to five fluorines;

or the pharmaceutically acceptable salts thereof.

A group of compounds which is preferred among the Z Group of compounds designated the AA Group, contains those compounds wherein $R^2$ is a quinolinyl, isoquinolinyl, indazolyl or benzimidazolyl ring, wherein said $R^2$ bicyclic ring is optionally mono- or di-substituted independently with hydroxy, halo, $(C_1-C_4)$alkoxy, $(C_1-C_4)$alkoxycarbonyl, $(C_1-C_4)$alkyl, $(C_1-C_4)$alkanoylamino, $(C_1-C_4)$alkoxycarbonylamino, sulfonamido, $(C_1-C_4)$alkylsulfonamido, mono-N- or di-N,N-$(C_1-C_4)$alkylamino, carbamoyl, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl, wherein said $(C_1-C_4)$alkoxy or $(C_1-C_4)$alkyl substituents are optionally mono-substituted with hydroxy, $(C_1-C_4)$alkanoylamino, $(C_1-C_4)$alkylsulfonamido, amino, mono-N- or di-N,N-$(C_1-C_4)$alkylamino, mono-N- or di-N,N-$(C_1-C_4)$alkylcarbamoyl, $(C_1-C_4)$alkylsulfonyl or mono-N- or di-N, N-$(C_1-C_4)$alkylaminosulfonyl or optionally substituted with one to five fluorines;

or the pharmaceutically acceptable salts thereof.

Especially preferred compounds of Formula I are the compounds

[5-cyclopropyl-1-(quinolin-8-yl)-1H-pyrazole-4-carbonyl] guanidine; or

[5-cyclopropyl-1-(quinolin-5-yl)-1H-pyrazole-4-carbonyl] guanidine;

or the pharmaceutically acceptable salts of said compounds.

Preferred salts of the immediately preceding compound are the mono- or di-mesylate salts.

Other especially preferred compounds of Formula I are the compounds

[1-(8-Bromoquinolin-5-yl)-5-cyclopropyl-1H-pyrazole-4-carbonyl]guanidine;
[1-(6-Chloroquinolin-5-yl)-5-cyclopropyl-1H-pyrazole-4-carbonyl]guanidine;
[1-(Indazol-7-yl)-5-cyclopropyl-1H-pyrazole-4-carbonyl]guanidine;
[1-(Benzimidazol-5-yl)-5-cyclopropyl-1H-pyrazole-4-carbonyl]guanidine;
[1-(1-Isoquinolyl)-5-cyclopropyl-1H-pyrazole-4-carbonyl]guanidine;
[5-Cyclopropyl-1-(4-quinolinyl)-1H-pyrazole-4-carbonyl]guanidine;
or the pharmaceutically acceptable salts of said compounds.

Especially preferred compounds within the AA Group are compounds wherein
a. $R^2$ is 8-bromoquinolin-5-yl;
b. $R^2$ is 6-Chloroquinolin-5-yl;
c. $R^2$ is indazol-7-yl;
d. $R^2$ is benzimidazol-5-yl;
e. $R^2$ is 1-isoquinolyl;
f. $R^2$ is 4-quinolinyl;
or the pharmaceutically acceptable salts of said compounds.

A preferred group of compounds, designated the BB Group, contains those comounds having the Formula I as shown above wherein Z is

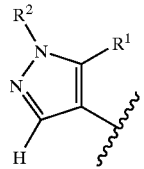

$R^1$ is $(C_1-C_4)$alkyl, $(C_3-C_7)$cycloalkyl, phenyl or phenyl $(C_1-C_4)$alkyl, said $(C_1-C_4)$alkyl optionally substituted with from one to nine fluorines, said $R^1$ substituent optionally mono- or di-substituted independently with $(C_1-C_4)$alkoxy, $(C_1-C_4)$alkylthio, $(C_1-C_4)$alkylsulfinyl or $(C_1-C_4)$alkylsulfonyl; and $R^2$ is a five to six membered nonaromatic heterocyclic ring having one to two heteroatoms selected independently from nitrogen, sulfur and oxygen or $R^2$ is unsubstituted $(C_1-C_4)$alkyl or unsubstituted $(C_3-C_7)$cycloalkyl; or $R^2$ is phenyl$(C_1-C_4)$alkyl, or a bicyclic ring consisting of two fused five and/or six membered partially saturated, fully saturated or fully unsaturated rings taken independently having one to four heteroatoms selected independently from nitrogen, sulfur and oxygen, said $R^2$ substituents optionally substituted on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_4)$ alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$ alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$ alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$ alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines,
or the pharmaceutically acceptable salts thereof.

A group of compounds which is preferred among the BB Group of compounds designated the CC Group, contains those compounds wherein
$R^1$ is $(C_1-C_4)$alkyl; and
$R^2$ is a bicyclic ring consisting of two fused five and/or six membered partially saturated, fully saturated or fully unsaturated rings taken independently having one to three heteroatoms selected independently from nitrogen, sulfur and oxygen, said $R^2$ bicyclic ring is optionally mono-substituted on carbon or nitrogen with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ bicyclic ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N, N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino are optionally mono-substituted with hydroxy, $(C_1-C_4)$alkoxycarbonyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$ alkylaminosulfonyl or optionally substituted with one to nine fluorines or the pharmaceutically acceptable salts thereof.

A group of compounds which is preferred among the CC Group of compounds designated the DD Group, contains those compounds wherein $R^2$ is a quinazolinyl, phthalazinyl, quinolinyl, isoquinolinyl, cinnolinyl, benzodioxanyl, quinoxalinyl, benzopyranyl, benzothiophenyl, benzodioxolyl, benzimidazolyl, indazolyl, indolyl, benzotriazolyl, benzoxazolyl, benzisoxazolyl, benzothiazolyl, benzisothiazolyl, benzoxadiazolyl or benzothiadiazolyl ring, wherein said $R^2$ bicyclic ring is optionally mono- or di-substituted independently with hydroxy, halo, $(C_1-C_4)$ alkoxy, $(C_1-C_4)$alkoxycarbonyl, $(C_1-C_4)$alkyl, $(C_1-C_4)$ alkanoylamino, ($C_1$–$C_4$)alkoxycarbonylamino, sulfonamido, ($C_1$–$C_4$)alkylsulfonamido, mono-N- or di-N,N-($C_1$–$C_4$)alkylamino, carbamoyl, mono-N- or di-N,N-($C_1$–$C_4$)alkylcarbamoyl, ($C_1$–$C_4$)alkylsulfonyl or mono-N- or di-N,N-($C_1$–$C_4$)alkylaminosulfonyl, wherein said ($C_1$–$C_4$)alkoxy, ($C_1$–$C_4$)alkyl, mono-N- or di-N,N-($C_1$–$C_4$)alkylamino substituents are optionally mono-substituted with hydroxy, ($C_1$–$C_4$)alkanoylamino, ($C_1$–$C_4$)alkylsulfonamido, amino, mono-N- or di-N,N-($C_1$–$C_4$)alkylamino, mono-N- or di-N,N-($C_1$–$C_4$) alkylcarbamoyl, ($C_1$–$C_4$)alkylsulfonyl or mono-N- or di-N, N-($C_1$–$C_4$)alkylaminosulfonyl or optionally substituted with one to five fluorines;

or the pharmaceutically acceptable salts thereof.

Especially preferred compounds of Formula I are the compounds

[1-(Indazol-6-yl)-5-ethyl-1H-pyrazole-4-carbonyl] guanidine;

[1-(Indazol-5-yl)-5-ethyl-1H-pyrazole-4-carbonyl] guanidine;

[1-(Benzimidazol-5-yl)-5-ethyl-1H-pyrazole-4-carbonyl] guanidine;

[1-(1-Methylbenzimidazol-6-yl)-5-ethyl-1H-pyrazole-4-carbonyl]guanidine

[1-(5-Quinolinyl)-5-n-propyl-1H-pyrazole-4-carbonyl] guanidine;

[1-(5-Quinolinyl)-5-isopropyl-1H-pyrazole-4-carbonyl] guanidine;

[5-Ethyl-1-(6-quinolinyl)-1H-pyrazole-4-carbonyl] guanidine;

[1-(2-Methylbenzimidazol-5-yl)-5-ethyl-1H-pyrazole-4-carbonyl]guanidine;

[1-(1,4-Benzodioxan-6-yl)-5-ethyl-1H-pyrazole-4-carbonyl]guanidine;

[1-(Benzotriazol-5-yl)-5-ethyl-1H-pyrazole-4-carbonyl] guanidine;

[1-(3-Chloroindazol-5-yl)-5-ethyl-1H-pyrazole-4-carbonyl] guanidine;

[1-(5-Quinolinyl)-5-butyl-1H-pyrazole-4-carbonyl] guanidine;

[5-propyl-1-(6-quinolinyl)-1H-pyrazole-4-carbonyl] guanidine;

[5-Isopropyl-1-(6-quinolinyl)-1H-pyrazole-4-carbonyl] guanidine;

or pharmaceutically acceptable salts of said compounds.

Especially preferred compounds within the DD Group are compounds wherein a. $R^1$ is ethyl; and $R^2$ is indazol-6-yl;
b. $R^1$ is ethyl; and $R^2$ is indazol-5-yl;
c. $R^1$ is ethyl; and $R^2$ is benzimidazol-5-yl;
d. $R^1$ is ethyl; and $R^2$ is 1-methylbenzimidazol-6-yl;
e. $R^1$ is n-propyl; and $R^2$ is 5-quinolinyl;
f. $R^1$ is isopropyl; and $R^2$ is 5-quinolinyl;
g. $R^1$ is ethyl; and $R^2$ is 6-quinolinyl;
h. $R^1$ is ethyl; and $R^2$ is 2-methylbenzimidazol-5-yl;
i. $R^1$ is ethyl; and $R^2$ is 1,4-benzodioxan-6-yl;
j. $R^1$ is ethyl; and $R^2$ is benzotriazol-5-yl;
k. $R^1$ is ethyl; and $R^2$ is 3-Chloroindazol-5-yl;
l. $R^1$ is butyl; and $R^2$ is 5-quinolinyl;
m. $R^1$ is n-propyl; and $R^2$ is 6-quinolinyl;
n. $R^1$ is isopropyl; and $R^2$ is 6-quinolinyl;

or the pharmaceutically acceptable salts of said compounds.

A preferred group of compounds, designated the EE Group, contains those comounds having the Formula I as shown above wherein Z is

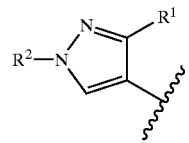

$R^1$ is ($C_1$–$C_4$)alkyl, ($C_3$–$C_7$)cycloalkyl, phenyl or phenyl ($C_1$–$C_4$)alkyl, said ($C_1$–$C_4$)alkyl optionally substituted with from one to nine fluorines, said $R^1$ substituent optionally mono- or di-substituted independently with ($C_1$–$C_4$)alkoxy, ($C_1$–$C_4$)alkylthio, ($C_1$–$C_4$)alkylsulfinyl or ($C_1$–$C_4$)alkylsulfonyl; and $R^2$ is a five to six membered nonaromatic heterocyclic ring having one to two heteroatoms selected independently from nitrogen, sulfur and oxygen or $R^2$ is unsubstituted ($C_1$–$C_4$)alkyl or unsubstituted ($C_3$–$C_7$)cycloalkyl; or $R^2$ is phenyl($C_1$–$C_4$)alkyl, or a bicyclic ring consisting of two fused five and/or six membered partially saturated, fully saturated or fully unsaturated rings taken independently having one to four heteroatoms selected independently from nitrogen, sulfur and oxygen, said $R^2$ substituents optionally substituted on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$)alkoxy, ($C_1$–$C_4$)alkoxycarbonyl, ($C_1$–$C_4$) alkyl, formyl, ($C_1$–$C_4$)alkanoyl, ($C_1$–$C_4$)alkanoyloxy, ($C_1$–$C_4$)alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$) alkylthio, ($C_1$–$C_4$)alkylsulfinyl, ($C_1$–$C_4$)alkylsulfonyl, mono-N- or di-N,N-($C_1$–$C_4$)alkylaminosulfonyl, ($C_2$–$C_4$) alkenyl, ($C_2$–$C_4$)alkynyl or ($C_5$–$C_7$)cycloalkenyl, wherein said ($C_1$–$C_4$)alkoxy, ($C_1$–$C_4$)alkyl, ($C_1$–$C_7$) alkanoyl, ($C_1$–$C_4$)alkylthio, mono-N- or di-N,N-($C_1$–$C_4$) alkylamino or ($C_3$–$C_7$)cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$–$C_4$)alkanoylamino, ($C_1$–$C_4$) alkanoyloxy, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, nitro, ($C_1$–$C_4$) alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines, or the pharmaceutically acceptable salts thereof.

A group of compounds which is preferred among the EE Group of compounds designated the FF Group, contains those compounds wherein $R^1$ is ($C_1$–$C_4$)alkyl; and $R^2$ is a bicyclic ring consisting of two fused five and/or six membered partially saturated, fully saturated or fully unsaturated rings taken independently having one to three heteroatoms selected independently from nitrogen, sulfur and oxygen, said $R^2$ bicyclic ring is optionally mono-substituted on carbon or nitrogen with a fully saturated or fully unsaturated five to six membered ring optionally having one to two heteroatoms selected independently from oxygen, sulfur and nitrogen, said ring optionally mono-substituted with ($C_1$–$C_4$)alkyl said R² bicyclic ring is also optionally mono- or di-substituted independently on carbon or nitrogen with hydroxy, halo, (C₁–C₄)alkoxy, (C₁–C₄)alkoxycarbonyl, (C₁–C₄)alkyl, (C₁–C₄)alkanoyl, (C₁–C₄)alkanoyloxy, (C₁–C₄)alkanoylamino, (C₁–C₄)alkoxycarbonylamino, sulfonamido, (C₁–C₄)alkylsulfonamido, amino, mono-N- or di-N,N-(C₁–C₄)alkylamino, carbamoyl, mono-N- or di-N,N-(C₁–C₄)alkylcarbamoyl, cyano, (C₁–C₄)alkylthio, (C₁–C₄)alkylsulfinyl, (C₁–C₄)alkylsulfonyl or mono-N- or di-N,N-(C₁–C₄)alkylaminosulfonyl wherein said (C₁–C₄)alkoxy, (C₁–C₄)alkyl, (C₁–C₇)alkanoyl, (C₁–C₄)alkylthio, mono-N- or di-N,N-(C₁–C₄)alkylamino are optionally mono-substituted with hydroxy, (C₁–C₄)alkoxycarbonyl, (C₁–C₄)alkanoyl, (C₁–C₄)alkanoylamino, (C₁–C₄)alkanoyloxy, (C₁–C₄)alkoxycarbonylamino, sulfonamido, (C₁–C₄)alkylsulfonamido, amino, mono-N- or di-N,N-(C₁–C₄)alkylamino, carbamoyl, mono-N- or di-N,N-(C₁–C₄)alkylcarbamoyl, (C₁–C₄)alkylthio, (C₁–C₄)alkylsulfinyl, (C₁–C₄)alkylsulfonyl or mono-N- or di-N,N-(C₁–C₄)alkylaminosulfonyl or optionally substituted with one to nine fluorines.

or the pharmaceutically acceptable salts thereof.

A group of compounds which is preferred among the FF Group of compounds designated the GG Group, contains those compounds wherein R² is a quinazolinyl, phthalazinyl, quinolinyl, isoquinolinyl, cinnolinyl, benzodioxanyl, quinoxalinyl, benzopyranyl, benzothiophenyl, benzodioxolyl, benzimidazolyl, indazolyl, indolyl, benzotriazolyl, benzoxazolyl, benzisoxazolyl, benzothiazolyl, benzisothiazolyl, benzoxadiazolyl or benzothiadiazolyl ring, wherein said R² bicyclic ring is optionally mono- or di-substituted independently with hydroxy, halo, (C₁–C₄)alkoxy, (C₁–C₄)alkoxycarbonyl, (C₁–C₄)alkyl, (C₁–C₄)alkanoylamino, (C₁–C₄)alkoxycarbonylamino, sulfonamido, (C₁–C₄)alkylsulfonamido, mono-N- or di-N,N-(C₁–C₄)alkylamino, carbamoyl, mono-N- or di-N,N-(C₁–C₄)alkylcarbamoyl, (C₁–C₄)alkylsulfonyl or mono-N- or di-N,N-(C₁–C₄)alkylaminosulfonyl, wherein said (C₁–C₄)alkoxy, (C₁–C₄)alkyl, mono-N- or di-N,N-(C₁–C₄)alkylamino substituents are optionally mono-substituted with hydroxy, (C₁–C₄)alkanoylamino, (C₁–C₄)alkylsulfonamido, amino, mono-N- or di-N,N-(C₁–C₄)alkylamino, mono-N- or di-N,N-(C₁–C₄)alkylcarbamoyl, (C₁–C₄)alkylsulfonyl or mono-N- or di-N,N-(C₁–C₄)alkylaminosulfonyl or optionally substituted with one to five fluorines;

or the pharmaceutically acceptable salts thereof.

Especially preferred compounds of Formula I are the compounds

[1-(Indazol-7-yl)-3-methyl-1H-pyrazole-4-carbonyl]guanidine;

[1-(2,1,3-Benzothiadiazol-4-yl)-3-methyl-1H-pyrazole-4-carbonyl]guanidine;

[3-Methyl-1-(quinolin-5-yl)-1H-pyrazole-4-carbonyl]guanidine;

or the pharmaceutically acceptable salts of said compounds.

Especially preferred compounds within the GG Group of compounds are compounds wherein a. R¹ is methyl; and R² is indazol-7-yl;
b. R¹ is methyl; and R² is 2,1,3-benzothiadiazol-4-yl;
c. R¹ is methyl; and R² is quinolin-5-yl;

or the pharmaceutically acceptable salts of said compounds.

A preferred group of compounds, designated the HH Group, contains those comounds having the Formula I as shown above wherein Z is

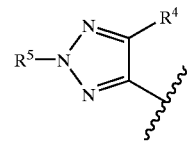

R⁴ is (C₁–C₄)alkyl, (C₃–C₇)cycloalkyl, phenyl or phenyl (C₁–C₄)alkyl, said (C₁–C₄)alkyl optionally substituted with from one to nine fluorines, said R⁴ substituent optionally mono- or di-substituted independently with (C₁–C₄)alkoxy, (C₁–C₄)alkylthio, (C₁–C₄)alkylsulfinyl or (C₁–C₄)alkylsulfonyl; and R⁵ is a five to six membered nonaromatic heterocyclic ring having one to two heteroatoms selected independently from nitrogen, sulfur and oxygen or R⁵ is unsubstituted (C₁–C₄)alkyl or (C₃–C₇)cycloalkyl; or R⁵ is phenyl (C₁–C₄)alkyl, or a bicyclic ring consisting of two fused five and/or six membered partially saturated, fully saturated or fully unsaturated rings taken independently having one to four heteroatoms selected independently from nitrogen, sulfur and oxygen, said R⁵ substituents optionally substituted on carbon or nitrogen with up to three substituents independently selected from R⁶, R⁷ and R⁸, wherein one of R⁶, R⁷ and R⁸ is optionally a partially saturated, fully saturated, or fully unsaturated three to seven membered ring optionally having one to three heteroatoms selected independently from oxygen, sulfur and nitrogen optionally substituted with (C₁–C₄)alkyl and additionally R⁶, R⁷ and R⁸ are optionally hydroxy, nitro, halo, (C₁–C₄)alkoxy, (C₁–C₄)alkoxycarbonyl, (C₁–C₄)alkyl, formyl, (C₁–C₄)alkanoyl, (C₁–C₄)alkanoyloxy, (C₁–C₄)alkanoylamino, (C₁–C₄)alkoxycarbonylamino, sulfonamido, (C₁–C₄)alkylsulfonamido, amino, mono-N- or di-N,N-(C₁–C₄)alkylamino, carbamoyl, mono-N- or di-N,N-(C₁–C₄)alkylcarbamoyl, cyano, thiol, (C₁–C₄)alkylthio, (C₁–C₄)alkylsulfinyl, (C₁–C₄)alkylsulfonyl, mono-N- or di-N,N-(C₁–C₄)alkylaminosulfonyl, (C₂–C₄)alkenyl, (C₂–C₄)alkynyl or (C₅–C₇)cycloalkenyl, wherein said (C₁–C₄)alkoxy, (C₁–C₄)alkyl, (C₁–C₇)alkanoyl, (C₁–C₄)alkylthio, mono-N- or di-N,N-(C₁–C₄)alkylamino or (C₃–C₇)cycloalkyl R⁶, R⁷ and R⁸substituents are optionally mono-substituted independently with hydroxy, (C₁–C₄)alkoxycarbonyl, (C₃–C₇)cycloalkyl, (C₁–C₄)alkanoyl, (C₁–C₄)alkanoylamino, (C₁–C₄)alkanoyloxy, (C₁–C₄)alkoxycarbonylamino, sulfonamido, (C₁–C₄)alkylsulfonamido, amino, mono-N- or di-N,N-(C₁–C₄)alkylamino, carbamoyl, mono-N- or di-N,N-(C₁–C₄)alkylcarbamoyl, cyano, thiol, nitro, (C₁–C₄)alkylthio, (C₁–C₄)alkylsulfinyl, (C₁–C₄)alkylsulfonyl or mono-N- or di-N,N-(C₁–C₄)alkylaminosulfonyl or optionally substituted with one to nine fluorines, or the pharmaceutically acceptable salts thereof.

A group of compounds which is preferred among the HH Group of compounds designated the II Group, contains those compounds wherein R⁴ is (C₁–C₄)alkyl; and R⁵ is a bicyclic ring consisting of two fused five and/or six membered partially saturated, fully saturated or fully unsaturated rings taken independently having one to three heteroatoms selected independently from nitrogen, sulfur and oxygen, said R⁵ bicyclic ring is optionally mono-substituted on carbon with a fully saturated or fully unsaturated five to six membered ring optionally having one to two heteroatoms selected independently from oxygen, sulfur and nitrogen, said ring optionally mono-substituted with (C₁–C₄)alkyl said $R^5$ bicyclic ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino are optionally mono-substituted with hydroxy, $(C_1-C_4)$alkoxycarbonyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines.

or the pharmaceutically acceptable salts thereof.

A group of compounds which is preferred among the II Group of compounds designated the JJ Group, contains those compounds wherein $R^5$ is a quinazolinyl, phthalazinyl, quinolinyl, isoquinolinyl, cinnolinyl, benzodioxanyl, quinoxalinyl, benzopyranyl, benzothiophenyl, benzodioxolyl, benzimidazolyl, indazolyl, indolyl, benzotriazolyl, benzoxazolyl, benzisoxazolyl, benzothiazolyl, benzisothiazolyl, benzoxadiazolyl or benzothiadiazolyl ring, wherein said $R^5$ bicyclic ring is optionally mono- or di-substituted independently with hydroxy, halo, $(C_1-C_4)$alkoxy, $(C_1-C_4)$alkoxycarbonyl, $(C_1-C_4)$alkyl, $(C_1-C_4)$alkanoylamino, $(C_1-C_4)$alkoxycarbonylamino, sulfonamido, $(C_1-C_4)$alkylsulfonamido, mono-N- or di-N,N-$(C_1-C_4)$alkylamino, carbamoyl, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl, wherein said $(C_1-C_4)$alkoxy, $(C_1-C_4)$alkyl, mono-N- or di-N,N-$(C_1-C_4)$alkylamino substituents are optionally mono-substituted with hydroxy, $(C_1-C_4)$alkanoylamino, $(C_1-C_4)$alkylsulfonamido, amino, mono-N- or di-N,N-$(C_1-C_4)$alkylamino, mono-N- or di-N,N-$(C_1-C_4)$alkylcarbamoyl, $(C_1-C_4)$alkylsulfonyl or mono-N- or di-N,N-$(C_1-C_4)$alkylaminosulfonyl or optionally substituted with one to five fluorines;

or the pharmaceutically acceptable salts thereof.

A preferred group of compounds, designated the KK Group, contains those comounds having the Formula I as shown above wherein Z is Z is

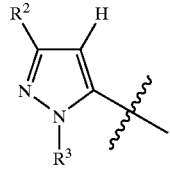

$R^2$ is $(C_1-C_4)$alkyl, $(C_3-C_7)$cycloalkyl, M or M$(C_1-C_4)$alkyl, any of said previous $(C_1-C_4)$alkyl moieties optionally having from one to nine fluorines; said $(C_1-C_4)$alkyl or $(C_3-C_4)$cycloalkyl optionally mono- or di-substituted independently with hydroxy, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkyl, mono-N- or di-N,N-$(C_1-C_4)$alkylcarbamoyl or mono-N- or di-N,N-$(C_1-C_4)$alkylaminosulfonyl; and said $(C_3-C_4)$cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_4)$alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines; and $R^3$ is $(C_1-C_4)$alkyl, $(C_3-C_7)$cycloalkyl, phenyl or phenyl $(C_1-C_4)$alkyl, said $(C_1-C_4)$alkyl optionally substituted with from one to nine fluorines, said $R^3$ substituent optionally mono- or di-substituted independently with $(C_1-C_4)$alkoxy, $(C_1-C_4)$alkylthio, $(C_1-C_4)$alkylsulfinyl, $(C_1-C_4)$alkylsulfonyl or $(C_1-C_4)$alkyl, or a pharmaceutically acceptable salt thereof.

A group of compounds which is preferred among the KK Group of compounds designated the LL Group, contains those compounds wherein $R^3$ is $(C_1-C_4)$alkyl;

$R^2$ is phenyl, said phenyl optionally mono-substituted on carbon with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ ring is also optionally mono- or di-substituted independently on carbon with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$ alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino are optionally mono-substituted with hydroxy, $(C_1-C_4)$alkoxycarbonyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$ alkylaminosulfonyl or optionally substituted with one to nine fluorines, or the pharmaceutically acceptable salts thereof.

A group of compounds which is preferred among the KK Group of compounds designated the MM Group, contains those compounds wherein $R^3$ is $(C_1-C_4)$alkyl;

$R^2$ is a bicyclic ring consisting of two fused five and/or six membered partially saturated, fully saturated or fully unsaturated rings taken independently said $R^2$ bicyclic ring is optionally mono-substituted on carbon with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ bicyclic ring is also optionally mono- or di-substituted independently on carbon with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$ alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino are optionally mono-substituted with hydroxy, $(C_1-C_4)$alkoxycarbonyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$ alkylaminosulfonyl or optionally substituted with one to nine fluorines,
or the pharmaceutically acceptable salts thereof.

A group of compounds which is preferred among the KK Group of compounds designated the NN Group, contains those compounds wherein $R^3$ is $(C_1-C_4)$alkyl;

$R^2$ is a five to six membered monocyclic aromatic ring having one to two heteroatoms selected independently from oxygen, sulfur and nitrogen;

said $R^2$ ring is optionally mono-substituted on carbon with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$ alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino are optionally mono-substituted with hydroxy, $(C_1-C_4)$alkoxycarbonyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$ alkylaminosulfonyl or optionally substituted with one to nine fluorines or the pharmaceutically acceptable salts thereof.

A group of compounds which is preferred among the KK Group of compounds designated the OO Group, contains those compounds wherein $R^3$ is $(C_1-C_4)$alkyl;

$R^2$ is a bicyclic ring consisting of two fused five and/or six membered partially saturated, fully saturated or fully unsaturated rings taken independently having one to three heteroatoms selected independently from nitrogen, sulfur and oxygen, said $R^2$ bicyclic ring is optionally mono-substituted on carbon or nitrogen with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ bicyclic ring is also optionally mono- or di-substituted independently on carbon or nitrogen with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N, N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_7)$ alkanoyl, $(C_1-C_4)$alkylthio, mono-N- or di-N,N-$(C_1-C_4)$ alkylamino are optionally mono-substituted with hydroxy, $(C_1-C_4)$alkoxycarbonyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$ alkylaminosulfonyl or optionally substituted with one to nine fluorines or the pharmaceutically acceptable salts thereof.

Another aspect of this invention is directed to the esters of
5-cyclopropyl-1-(2-trifluoromethylphenyl)-1H-pyrazole-4-carboxylate,
5-methyl-1-(6-quinolinyl)-1H-pyrazole-4-carboxylate,
5-methyl-1-naphthalenyl-1H-pyrazole-4-carboxylate,
5-cyclopropyl-1-(quinolin-8-yl)-1H-pyrazole-4-carboxylate,
5-cyclopropyl-1-(quinolin-5-yl)-1H-pyrazole-4-carboxylate,
5-ethyl-1-(quinolin-5-yl)-1H-pyrazole-4-carboxylate or
n-butyl 1-(isoquinolin-5-yl)-3-methyl-1H-pyrazole-4-carboxylate wherein said esters are benzyl, $(C_1–C_6)$alkyl or $(C_4–C_8)$ cycloalkyl, said $(C_4–C_8)$cycloalkyl optionally monosubstituted with $(C_1–C_4)$alkyl or a salt of said esters.

Yet another aspect of this invention is directed to the following compounds
5-methyl-2-(5-quinolinyl)-2H-1,2,3-triazole-4-carboxylic acid,
5-methyl-2-(5-isoquinolinyl)-2H-1,2,3-triazole-4-carboxylic acid,
2-(1-naphthalenyl)-5-methyl-2H-1,2,3-triazole-4-carboxylic acid,
5-methyl-1-(6-quinolinyl)-1H-pyrazole-4-carboxylic acid,
5-methyl-1-naphthalenyl-1H-pyrazole-4-carboxylic acid,
5-cyclopropyl-1-(quinolin-8-yl)-1H-pyrazole-4-carboxylic acid,
5-cyclopropyl-1-(2-trifluoromethylphenyl)-1H-pyrazole-4-carboxylic acid,
5-ethyl-1-(quinolin-5-yl)-1H-pyrazole-4-carboxylic acid,
5-cyclopropyl-1-(quinolin-5-yl)-1H-pyrazole-4-carboxylic acid or
1-(isoquinolin-5-yl)-3-methyl-1H-pyrazole-4-carboxylic acid or the acid chlorides thereof or a salt of said compounds or of said acid chlorides.

Another aspect of this invention is a method of treating a mammal (e.g., human) having a disease or condition mediated by NHE-1 by administering a pharmaceutically acceptable amount of a compound of Formula I, a prodrug thereof, or a pharmaceutically acceptable salt of said compound or of said prodrug to the mammal.

Another aspect of this invention is directed to a method of reducing tissue damage (e.g., substantially preventing tissue damage, inducing tissue protection) resulting from ischemia comprising administering to a mammal (e.g., a female or male human) in need of such treatment a therapeutically effective amount of a compound of Formula I a prodrug thereof, or a pharmaceutically acceptable salt of said compound or of said prodrug.

Preferred ischemic tissues taken individually or as a group are wherein the ischemic tissue is cardiac, brain, liver, kidney, lung, gut, skeletal muscle, spleen, pancreas, nerve, spinal cord, retina tissue, the vasculature, or intestinal tissue.

An especially preferred ischemic tissue is cardiac tissue.

It is especially preferred that the compounds are administered to prevent perioperative myocardial ischemic injury.

Preferably, the compounds of this invention are administered prophylactically.

The ischemic damage may occur during organ transplantation.

Preferably, the compounds of this invention are administered prior to, during or shortly after, cardiac surgery or non-cardiac surgery.

In one aspect of this invention a compound of Formula I is administered locally.

A preferred dosage is about 0.001 to 100 mg/kg/day of the Formula I compound a prodrug thereof. An especially preferred dosage is about 0.01 to 50 mg/kg/day of a compound of Formula I, a prodrug thereof, or a pharmaceutically acceptable salt of said compound or of said prodrug.

Another aspect of this invention is directed to a method of reducing myocardial tissue damage (e.g., substantially preventing tissue damage, inducing tissue protection) during surgery (e.g., coronary artery bypass grafting (CABG) surgeries, vascular surgeries, percutaneous transluminal coronary angioplasty (PTCA) or any percutaneous transluminal coronary intervention (PTCI), organ transplantation, or other non-cardiac surgeries) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method of reducing myocardial tissue damage (e.g., substantially preventing tissue damage, inducing tissue protection) in patients presenting with ongoing cardiac (acute coronary syndromes, e.g. myocardial infarction or unstable angina) or cerebral ischemic events (e.g. stroke) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a chronic method of reducing myocardial tissue damage (e.g., substantially preventing tissue damage, inducing tissue protection) in a patient with diagnosed coronary heart disease (e.g. previous myocardial infarction or unstable angina) or patients who are at high risk for myocardial infarction (age>65 and two or more risk factors for coronary heart disease) comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method of preventing ischemic damage comprising the chronic oral administration to a mammal in need of such treatment of a therapeutically effective amount of a compound of Formula I a prodrug of said compound or a pharmaceutically acceptable salt of said compound or of said prodrug.

Another aspect of this invention is directed to a method for treating cardiovascular diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating arteriosclerosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating hypertension comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating arrhythmia comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating angina pectoris comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cardiac hypertrophy comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating renal diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diabetic complications comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating restenosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating diseases of cell proliferation comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cancerous diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating fibrotic diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating glomerular nephrosclerosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating organ hypertrophies or hyperplasias comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating pulmonary fibrosis comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebro ischemic disorders comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating myocardial stunning comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating myocardial dysfunction comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating cerebrovascular diseases comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating organ hypertrophies or hyperplasias comprising administering to a mammal (e.g., a female or male human) a therapeutically effective amount of a compound of Formula I, a prodrug thereof, or a pharmaceutically acceptable salt of said compound or of said prodrug.

Another aspect of this invention is directed to a method for treating organ hypertrophies or hyperplasias comprising administering to a mammal (e.g., a female or male human) a therapeutically effective amount of a compound of Formula I, a prodrug thereof, or a pharmaceutically acceptable salt of said compound or of said prodrug.

This invention is also directed to pharmaceutical compositions which comprise a therapeutically effective amount of a compound of Formula I, a prodrug thereof, or a pharmaceutically acceptable salt of said compound or of said prodrug and a pharmaceutically acceptable carrier.

This invention is also directed to pharmaceutical compositions for the reduction of tissue damage resulting from ischemia which comprise a therapeutically effective amount of a compound of Formula I, a prodrug thereof, or a pharmaceutically acceptable salt of said compound or of said prodrug and a pharmaceutically acceptable carrier.

Yet another aspect of this invention are combinations of a compound of Formula I, a prodrug thereof, or a pharmaceutically acceptable salt of said compound or of said prodrug and other compounds as described below.

Yet another aspect of this invention is directed to pharmaceutical compositions comprising a compound of Formula I or a pharmaceutically acceptable salt or prodrug thereof and a cardiovascular agent and for the use of such compositions for the reduction of tissue damage resulting from tissue ischemia in mammals (e.g., humans, male or female).

In the above pharmaceutical compositions and methods preferred Formula I compounds include the preferred groups of compounds described above labeled as Group A-to Group OO.

Another aspect of this invention is a method of reducing tissue damage (e.g., substantially preventing tissue damage, inducing tissue protection) resulting from or which could result from ischemia comprising administering to a mammal (e.g., a female or male human)

a. a first compound, said first compound being a Formula I compound, a prodrug thereof, or a pharmaceutically acceptable salt of said compound or of said prodrug; and b. a second compound, said second compound being a cardiovascular agent wherein the amounts of the first and second compounds result in a therapeutic effect.

Another aspect of this invention is a kit comprising:

a. a therapeutically effective amount of a Formula I compound, a prodrug thereof, or a pharmaceutically acceptable salt of said compound or of said prodrug and a pharmaceutically acceptable carrier, vehicle or diluent in a first unit dosage form;

b. a therapeutically effective amount of a cardiovascular agent and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits, preferably the cardiovascular agents are for example, β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), potassium channel openers, adenosine, adenosine agonists, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g. tPA), platelet inhibitors (e.g., reopro), aspirin, dipyridamol, potassium chloride, clonidine, prazosin or adenosine $A_3$ receptor agonists.

In the above combination compositions, combination methods and kits preferred Formula I compounds include the preferred groups of compounds described above labeled as Group A to Group OO.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being a glycogen phosphorylase inhibitor; and/or optionally a pharmaceutical carrier, vehicle or diluent.

Another aspect of this invention is a method of reducing tissue damage (e.g., substantially preventing tissue damage, inducing tissue protection) resulting from or which could result from ischemia comprising administering to a mammal (e.g., a female or male human)

a. a first compound, said first compound being a Formula I compound, a prodrug thereof, or a pharmaceutically acceptable salt of said compound or of said prodrug; and b. a second compound, said second compound being a glycogen phosphorylase inhibitor wherein the amounts of the first and second compounds result in a therapeutic effect.

Another aspect of this invention is a kit comprising:

a. a therapeutically effective amount of a Formula I compound, a prodrug thereof, or a pharmaceutically acceptable salt of said compound or of said prodrug and a pharmaceutically acceptable carrier, vehicle or diluent in a first unit dosage form;

b. a therapeutically effective amount of a glycogen phosphorylase inhibitor and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits preferred Formula I compounds include the preferred groups of compounds described above labeled as Group A to Group OO.

In the above combination compositions, combination methods and kits preferred glycogen phosphorylase inhibitors are 5-chloro-1H-indole-2-carboxylic acid [(1S)-((R)-hydroxy-dimethylcarbamoyl-methyl)-2-phenyl-ethyl]-amide, 5,6-dichloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid ((1S)-{(R)-hydroxy-[(2-hydroxy-ethyl)-methyl-carbamoyl]-methyl}-2-phenyl-ethyl)-amide, 5-chloro-1H-indole-2-carboxylic acid {(1S)-[(R)-hydroxy-(methyl-pyridin-2-yl-carbamoyl)-methyl]-2-phenyl-ethyl}-amide or 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide.

5-chloro-1H-indole-2-carboxylic acid [(1S)-benzyi-(2R)-hydroxy-3-(4-methyl-piperazin-1-yl)-3-oxo-propyl]-amide hydrochloride, 5-chloro-1H-indole-2-carboxylic acid [(1S)-benzyl-(2R)-hydroxy-3-(3-hydroxy-azetidin-1-yl)-3-oxo-propyl]-amide, 5-chloro-1H-indole-2-carboxylic acid ((1S)-benzyl-(2R)-hydroxy-3-isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-chloro-1H-indole-2-carboxylic acid [(1S)-benzyl-(2R)-hydroxy-3-((3S)-hydroxy-pyrrolidin-1-yl)-3-oxo-propyl]-amide, 5-chloro-1H-indole-2-carboxylic acid [(1S)-benzyl-3-((3S,4S)-dihydroxy-pyrrolidin-1-yl)-(2R)-hydroxy-3-oxo-propyl]-amide, 5-chloro-1H-indole-2-carboxylic acid [(1S)-benzyl-3-((3R,4S)-dihydroxy-pyrrolidin-1-yl)-(2R)-hydroxy-3-oxo-propyl]-amide or 5-chloro-1H-indole-2-carboxylic acid ((1S)-benzyl-(2R)-hydroxy-3-morpholin-4-yl-3-oxo-propyl)-amide.

5-chloro-1H-indole-2-carboxylic acid [(1S)-benzyl-2-(3-hydroxyimino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S,4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-2-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S,4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-chloro-1H-indole-2-carboxylic acid [(1S)-benzyl-2-(3-hydroxyimino-azetidin-1-yl)-2-oxo-ethyl]-amide or 5-chloro-1H-indole-2-carboxylic acid [(1S)-benzyl-2-(4-hydroxyimino-piperidin-1-yl)-2-oxo-ethyl]-amide.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being an aldose reductase inhibitor; and/or optionally a pharmaceutical carrier, vehicle or diluent.

Another aspect of this invention is a method of reducing tissue damage (e.g., substantially preventing tissue damage, inducing tissue protection) resulting from or which could result from ischemia comprising administering to a mammal (e.g., a female or male human)

a. a first compound, said first compound being a Formula I compound, a prodrug thereof, or a pharmaceutically acceptable salt of said compound or of said prodrug; and b. a second compound, said second compound being an aldose reductase inhibitor wherein the amounts of the first and second compounds result in a therapeutic effect.

Another aspect of this invention is a kit comprising:

a. a therapeutically effective amount of a Formula I compound, a prodrug thereof, or a pharmaceutically acceptable salt of said compound or of said prodrug and a pharmaceutically acceptable carrier, vehicle or diluent in a first unit dosage form;

b. a therapeutically effective amount of an aldose reductase inhibitor and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits preferred Formula I compounds include the preferred groups of compounds described above labeled as Group A to Group OO.

In the above combination compositions, combination methods and kits a preferred aldose reductase inhibitor is zopolrestat: 1-phthalazineacetic acid, 3,4-dihydro-4-oxo-3-[[5-trifluoromethyl)-2-benzothiazolyl]methyl]-.

In the methods of treatment as applied to the combinations described above the following are preferred administration routes, modes etc.

Preferred ischemic tissues taken individually or as a group are wherein the ischemic tissue is cardiac, brain, liver, kidney, lung, gut, skeletal muscle, spleen, pancreas, nerve, spinal cord, retina tissue, the vasculature, or intestinal tissue.

An especially preferred ischemic tissue is cardiac tissue.

It is especially preferred that the compounds are administered to prevent perioperative myocardial ischemic injury.

Preferably, the compounds of this invention are administered prophylactically.

The ischemic damage may occur during organ transplantation.

Preferably, the compounds of this invention are administered prior to, during or shortly after, cardiac surgery or non-cardiac surgery.

In one aspect of this invention the compounds are administered locally.

In one aspect of this method myocardial tissue damage is reduced during surgery.

In another aspect of this method myocardial tissue damage is reduced in patients presenting with ongoing cardiac or cerebral ischemic events.

In yet another aspect of this method myocardial tissue damage is reduced by chronic administration of the combination in a patient with diagnosed coronary heart disease.

The term "reduction" is intended to include partial prevention or prevention which, although greater than that which would result from taking no compound or from taking a placebo, is less than 100% in addition to substantially total prevention.

The term "damage resulting from ischemia" as employed herein refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/or necrosis. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis ensues.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form).

Exemplary five to six membered aromatic rings optionally having one or two heteroatoms selected independently from oxygen, nitrogen and sulfur are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to three heteroatoms selected independently from oxygen, sulfur and nitrogen are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl and 1,4,2-oxadiazinyl.

Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms selected independently from nitrogen, sulfur and oxygen are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c) thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompases the particular example) are methylene, ethylene, propylene, butylene, pentylene, hexylene, heptylene).

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-($C_1$–$C_x$)alkyl . . . refers to the ($C_1$–$C_x$)alkyl moiety taken independently when it is di-N,N-($C_1$–$C_x$)alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

DMF means N,N-dimethylformamide. DMSO means dimethyl sulfoxide. THF means tetrahydrofuran.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

Other features and advantages will be apparent from the specification and claims which describe the invention.

DETAILED DESCRIPTION OF THE INVENTION

In general the compounds of this invention can be made by processes which include processes known in the chemical arts, particularly in light of the description contained herein. Certain processes for the manufacture of the compounds of this invention are provided as further features of the invention and are illustrated by the following reaction schemes. Other processes are described in the experimental section.

Briefly, in general, a compound of the Fomula Z—C(O) OH is coupled with guanidine in the presence of a suitable coupling agent.

SCHEME I
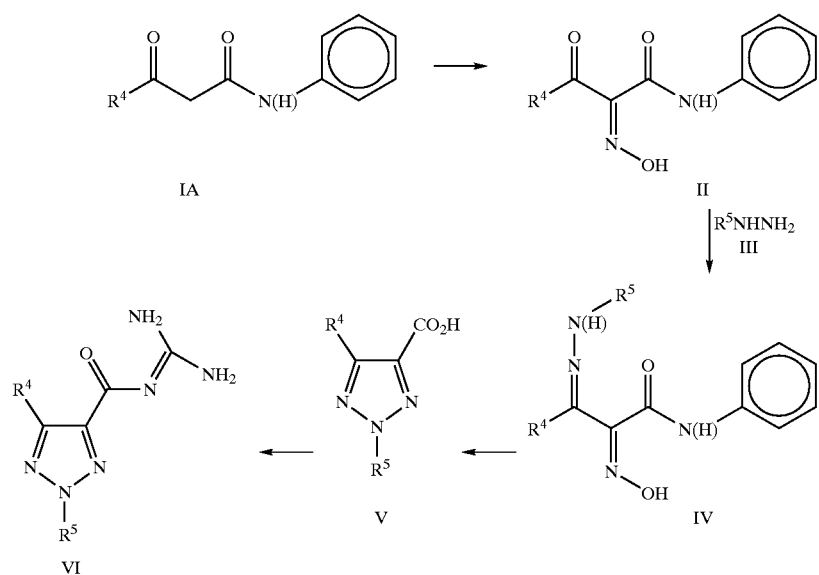
SCHEME II
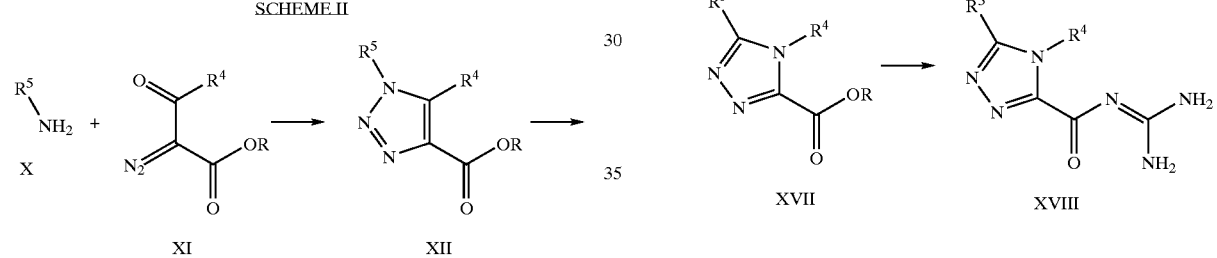
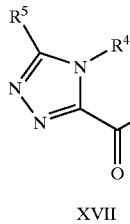
-continued
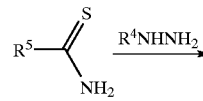
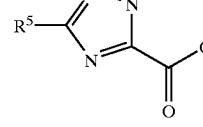
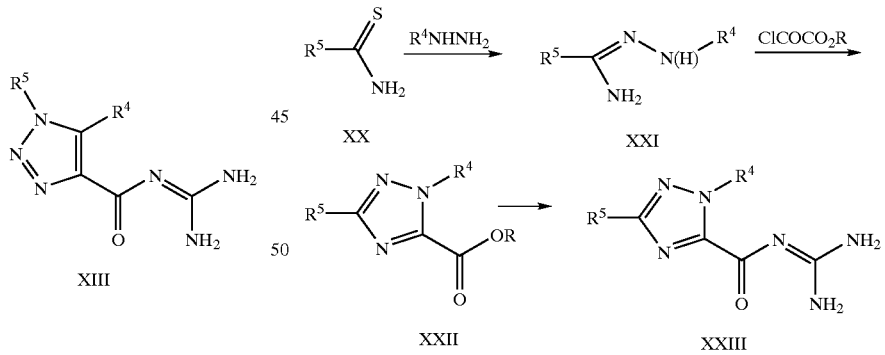
SCHEME III
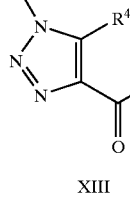
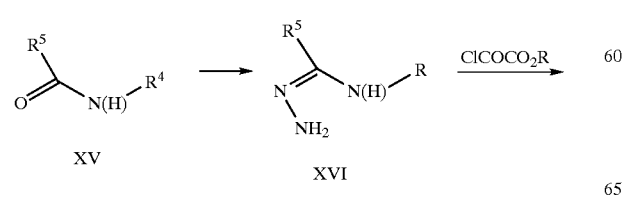
SCHEME V
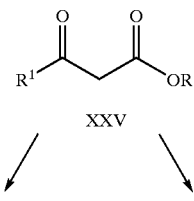

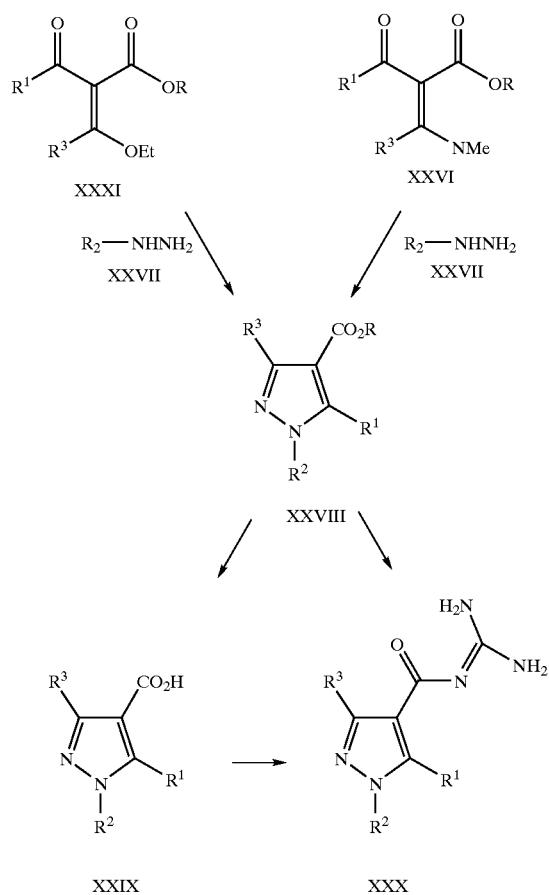

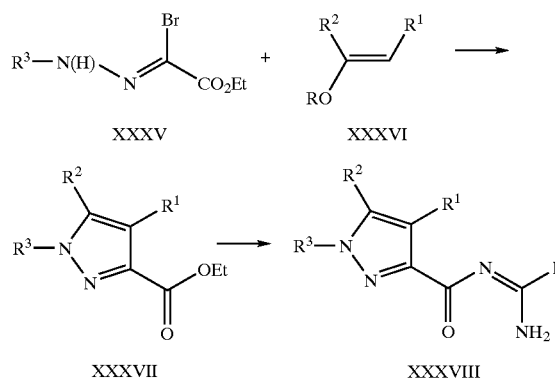

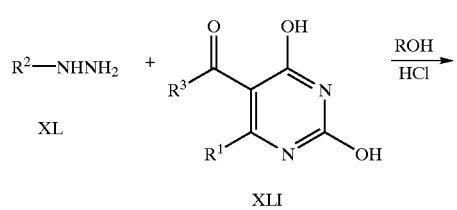

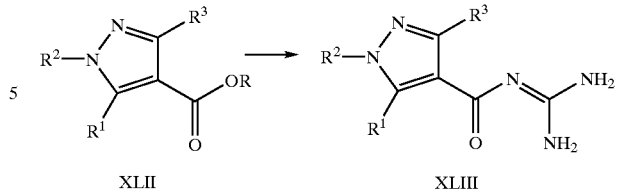

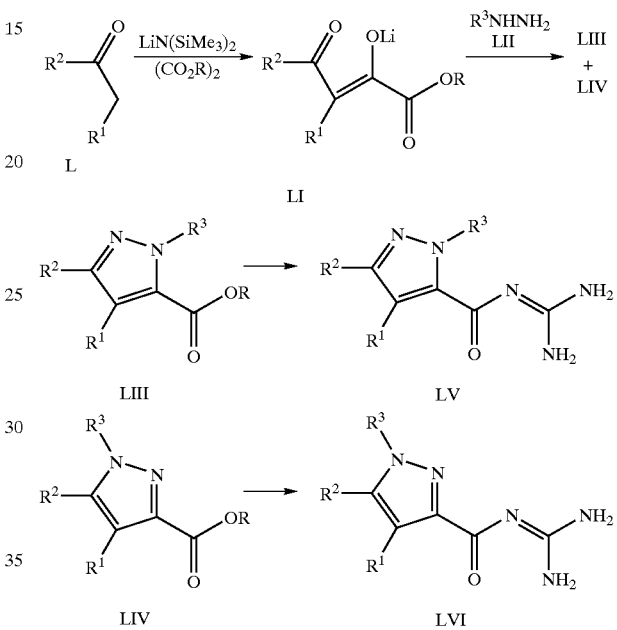

According to Scheme I the Formula IA compound, wherein $R^4$ is as described above, is dissolved or suspended in an aqueous alkali metal hydroxide solution (e.g. 1 N sodium hydroxide) along with sodium nitrite and the mixture is added to an aqueous acidic solution (e.g. 10% v/v sulfuric acid) at a pH of about 0 at a temperature of about 0° C. to about 5° C. for about 30 mmn to about 1 hour. The resulting mixture is filtered to yield the Formula II oxime. Alternatively, the Formula IA compound is dissolved in 1:1 acetic acid/propionic acid and solid sodium nitrite is added at about 0° C. The reaction mixture is stirred at about 0° C. for about 2 hours, then poured into ice water and the Formula II oxime is obtained by filtration.

The Formula II compound is reacted with a Formula III compound, wherein $R^5$ is as described above in a protic solvent such as ethanol at a temperature of about 50° C. to about 110° C. for about 10 min to about 1 hour to form the Formula IV hydrazone.

The Formula IV hydrazone is cyclized and hydrolyzed to the Formula V triazole in an alcoholic solvent such as 2-ethoxyethanol under basic conditions (e.g., potassium hydroxide) at a temperature of about 100° C. to about 175° C. for about ½ hour to about 2 hours followed by acidification to yield the Formula V triazole acid.

The Formula V acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HBT), dicyclohexylcarbodiimide/hydroxybenzotriazole(HBT), 2-ethoxy-1-ethoxycarbonyl-1,2-dihydroquinoline (EEDQ), and diethylphosphorylcyanide. The coupling is performed in an inert solvent, preferably an aprotic solvent at a temperature of about −20° C. to about 50° C. for about 1 to about 48 hours, in the presence of excess guanidine as base. Exemplary solvents include acetonitrile, dichloromethane, dimethylformamide and chloroform or mixtures thereof.

The coupling agent may also be that agent which converts the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess guanidine in an appropriate solvent together with an appropriate base. Appropriate solvent/base combinations are for example, dichloromethane, dimethylformamide or acetonitrile or mixtures thereof in the presence of excess guanidine as base. Other appropriate solvent/base combinations include water or a (($C_1$–$C_5$)alcohol) or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

According to Scheme II, the Formula X primary amine wherein $R^5$ is as described above is reacted with a Formula XI α-diazo-β-keto-ester wherein $R^4$ is as described above, and R is lower alkyl, in the presence of titanium tetrachloride analogously to the method described in Eguchi S. et al. Synthesis 1993, 793 to form the Formula XII triazole carboxylic acid ester. The Formula XII ester is converted directly to the acylguanidine XIII by reaction with guanidine in an alcoholic solvent at a temperature of about 60 to about 110° C., preferably refluxing methanol, for a period of 8 to 20 hours.

According to Scheme III, the Formula XV compound wherein $R^4$ and $R^5$ are as described above is treated with Lawesson's reagent (i.e., 2,4-bis(4-methoxyphenyl)-1,3-dithia-2,4-diphosphetane-2,4-disulfide) in an aprotic solvent such as dimethoxyethane at a temperature of about 20° C. to about 120° C. for about one to eight hours. The resulting thioamide is treated with an alkylating agent such as methyl iodide in a polar, inert solvent such as acetone, conveniently at ambient temperature for about eight hours to about forty-eight hours. The resulting compound is reacted with anhydrous hydrazine in an alcoholic solvent at a temperature of about 0° C. to about 25° C. for about one to eight hours to provide the Formula XVI compound (analogously as described in Doyle and Kurzer, Synthesis 1974, 583).

The Formula XVI compound is treated with a monoalkyloxalyl chloride in an aprotic solvent at a temperature of about 25° C. to about 50° C. for about one to eight hours to provide the Formula XVII carboxylic ester compound wherein R is lower alkyl. The Formula XVII ester is directly coupled with guanidine in an alcoholic solvent at a temperature of about 60° C. to about 110° C., preferably refluxing methanol, for a period of eight to twenty hours, to prepare the Formula XVIII triazole carbonyl guanidines.

According to Scheme IV the Formula XX compound wherein $R^5$ is as described above is treated with methyl iodide in an inert solvent, conveniently at ambient temperature for about four to twenty-four hours. The resulting compound is reacted with anhydrous $R^4$-hydrazine (wherein $R^4$ is as described above) in an alcoholic solvent at a temperature of about 0° C. to about 25° C. for about one to eight hours to provide the Formula XXI amidrazone compound (analogously as described in Doyle and Kurzer, Synthesis 1974, 583).

The Formula XXI compound is treated with a monoalkyloxalyl chloride in an aprotic solvent at a temperature of about 25° C. to about 50° C. for about one to eight hours to provide the Formula XXII carboxylic ester compound wherein R is lower alkyl. The Formula XXII ester is directly coupled with guanidine in an alcoholic solvent at a temperature of about 60° C. to about 110° C., preferably refluxing methanol, for a period of eight to twenty hours to prepare the Formula XXIII triazole carbonyl guanidines.

According to Scheme V the Formula XXV compound wherein $R^1$ is as described above is combined with excess $(CH_3O)_2C(R^3)N(CH_3)_2$ (N,N-dimethyl amide dimethyl acetal) wherein $R^3$ is as described above, optionally in the presence of an acid catalyst such as p-toluenesulfonic acid at a temperature of about 90° C. to about 110° C. for about one to about two hours to prepare the Formula XXVI compound above.

The Formula XXVI compound is cyclized with a Formula XXVII compound, wherein $R^2$ is as described above, in an inert solvent such as ethanol at a temperature of about 20° C. to about 30° C. for about 5 minutes to about one hour followed by heating to a temperature of about 70° C. to about 110° C. for about two hours to about four hours to form the Formula XXVIII pyrazole.

Alternatively, according to Scheme V the Formula XXV compound, wherein $R^1$ is as described above, is combined with a triethylorthoester (i.e., $R^3C(OEt)_3$ wherein $R^3$ is as described above) and acetic anhydride at a temperature of about 120° C. to about 150° C. for about two to about five hours to prepare the Formula XXXI compound.

The Formula XXXI compound is cyclized with a Formula XXVII compound, wherein $R^2$ is as described above, to form the Formula XXVIII pyrazole.

The Formula XXVIII pyrazole is hydrolyzed with a base such as sodium hydroxide or lithium hydroxide in a solvent such as water and/or methanol and/or THF conveniently at ambient temperature or at elevated temperature (e.g., reflux) for about one hour to about five hours to prepare the Formula XXIX acid.

The Formula XXIX acid is coupled with guanidine in the presence of a suitable coupling agent as described for the above coupling of the Formula V acid and guanidine. In one embodiment, the Formula XXIX acid is activated with thionyl chloride at a temperature of about 60° C. to about 90° C. for about fifteen minutes to about two hours. The resulting activated acid chloride is combined with guanidine hydrochloride and an inorganic base (e.g., sodium hydroxide) in anhydrous tetrahydrofuran and optionally methanol and/or water. The solution is heated, conveniently at reflux, for about one hour to about eight hours to prepare the Formula XXX compound.

Alternatively according to Scheme V the Formula XXVIII compound can be directly converted to the Formula XXX compound by several methods. For example, the Formula XXVIII compound can be heated in the presence of excess guanidine, in a polar protic solvent for example, methanol or isopropanol at a suitable temperature conveniently, at reflux for about one to about seventy-two hours. This transformation may also be performed by repeatedly removing the solvent, for example removing ethanol or toluene about four times, from a mixture of the Formula XXVIII compound and excess guanidine at a pressure of about one to about 100 mmHg and at a temperature of about 25° C. to about 95° C. This reaction may also be performed in the absence of solvent by heating the mixture of the Formula XXVIII compound and excess guanidine at a temperature of about 100° C. to about 180° C., optionally at about a pressure of about 1 to about 100 mmHg for about five minutes to about eight hours.

According to Scheme VI, the Formula XXXV compound, wherein $R^3$ is as described above, is reacted with the Formula XXXVI compound, wherein $R^1$ and $R^2$ are as described above, in an aprotic solvent at a temperature of about 0° C. to about 25° C. for about two hours to about twenty-four hours in the presence of an appropriate amine base, such as triethylamine, to form the Formula XXXVII compound.

The resulting Formula XXXVII compound is hydrolyzed and coupled with guanidine using one of the methods described in earlier Schemes, such as the method employing carbonyldiimidazole, to form the Formula XXXVIII compound.

According to Scheme VII, the Formula XL hydrazine, wherein $R^2$ is as described above, is reacted with the appropriate Formula XLI compound to form the Formula XLII pyrazole ester wherein R is lower alkyl according to the method of Bajnati, A. and Hubert-Habart, M. *Bull. Soc. Chim. France* 1988, 540. The resulting pyrazole ester is converted to the Formula XLIII acyl guanidine using the hydrolysis and coupling methods described above.

According to Scheme VIII, the Formula L compound wherein $R^2$ and $R^1$ are as described above is transformed to the Formula LI lithium salt where R is lower alkyl according to the method described in *J. Het Chem.* 1989, 26, 1389. The Formula LI lithium salt is combined with the Formula LII hydrazine, wherein $R^3$ is as described above, in an inert solvent such as ethanol, in the presence of a mineral acid, at a temperature of about 20° C. to about 30° C. for about five minutes to about one hour followed by heating to a temperature of about 70° C. to about 110° C. for two hours to about four hours to form both the Formula LIII and LIV pyrazoles. The Formula LIII and LIV pyrazoles are converted to the Formula LV and LVI acyl guanidines respectively using the hydrolysis and coupling methods described above.

Some of the methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The starting materials and reagents for the above described compounds, are also readily available or can be easily synthesized by those skilled in the art using conventional methods of organic synthesis. For example, the aromatic hydrazines used in this invention can be prepared from the corresponding aromatic amines by diazotization followed by reduction conveniently using stannous chloride using procedures known to those skilled in the art. For example, many of the compounds used herein are related to, or are derived from compounds found in nature, in which there is a large scientific interest and commercial need, and accordingly many such compounds are commercially available or are reported in the literature or are easily prepared from other commonly available substances by methods which are reported in the literature.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Those skilled in the art will recognize that the compounds of Formula I can exist in several tautomeric forms. All such tautomeric forms are considered as part of this invention. For example, all of the tautomeric forms of the carbonylguanidine moiety of the compounds of Formula I are included in this invention. Also, for example all enol-keto forms of the compounds of Formula I are included in this invention.

Some of the compounds of this invention are acidic and they form a salt with a pharmaceutically acceptable cation. All of the compounds of this invention are basic and they form a salt with a pharmaceutically acceptable anion. All such salts, including di-salts are within the scope of this invention and they can be prepared by conventional methods. For example, they can be prepared simply by contacting the acidic and basic entities, in either an aqueous, non-aqueous or partially aqueous medium. The salts are recovered either by filtration, by precipitation with a non-solvent followed by filtration, by evaporation of the solvent, or, in the case of aqueous solutions, by lyophilization, as appropriate.

In addition, when the compounds of this invention form metabolites, hydrates or solvates they are also within the scope of the invention.

Other cardiovascular agents known to those skilled in the art for example,β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), potassium channel openers, adenosine, adenosine agoinists, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g. tPA), platelet inhibitors (e.g., reopro), aspirin, dipyridamol, potassium chloride, clonidine, prazosin, aldose reductase inhibitors (e.g., zopolrestat) and adenosine $A_3$ receptor agonists may be used in conjunction with the compounds of this invention.

In combination therapy treatment, both the compounds of this invention and the other drug therapies are administered to mammals (e.g., humans, male or female) by conventional methods.

Any aldose reductase inhibitor may be used as the second compound (active agent) of this invention for combination therapies. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). A variety of aldose reductase inhibitors are described and referenced below, however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose). While not wishing to be bound by any particular theory or mechanism, it is believed that an aldose reductase inhibitor, by inhibiting aldose reductase, prevents or reduces ischemic damage as described hereinafter.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl}-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);

4. 3-(4-bromo-2-fluorobenzyl)-7-chloro-3,4-dihydro-2,4-dioxo-1 (2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'imidazolidine)2',5'-dione (U.S. Pat. No. 4,438,272);

13. 2,7-di-fluoro-spiro(9H-fluorene-9,4'imidazolidine)2',5'-dione (U.S. Pat. No. 4,436,745, U.S. Pat. No. 4,438,272);

14. 2,7-di-fluoro-5-methoxy-spiro(9H-fluorene-9,4'imidazolidine)2',5'-dione (U.S. Pat. No. 4,436,745, U.S. Pat. No. 4,438,272);

15. 7-fluoro-spiro(5H-indenol[1,2-b]pyridine-5,3'-pyrrolidine)2,5'-dione (U.S. Pat. No. 4,436,745, U.S. Pat. No. 4,438,272);

16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);

17. spiro[imidazolidine-4,5'(6H)-quinoline]2,5-dione-3'-chloro-7,'8'-dihydro-7'-methyl-(5'–Cis) (U.S. Pat. No. 5,066,659);

18. (2S,4S)-6-fluoro-2',5'-dioxospiro(chroman-4,4'-imidazolidine)-2-carboxamide (U.S. Pat. No. 5,447,946); and 19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula IB

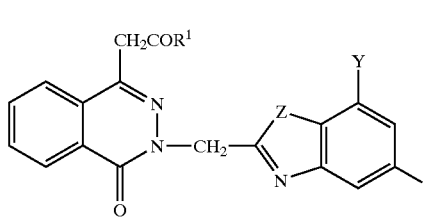

or a pharmaceutically acceptable salt thereof, wherein

Z is O or S;

$R^1$ is hydroxy or a group capable of being removed in vivo to produce a compound of formula IB wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula IB:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred.

An especially preferred aldose reductase inhibitor is 1-phthalazineacetic acid, 3,4-dihydro-4-oxo-3-[[5-trifluoromethyl)-2-benzothiazolyl]methyl]-.

The aldose reductase inhibitor compounds of this invention are readily available or can be easily synthesized by those skilled in the art using conventional methods of organic synthesis, particularly in view of the pertinent patent specification descriptions.

An amount of the aldose reductase inhibitor of this invention that is effective for the activities of this invention may be used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published international patent applications: PCT application publication WO 96/39384 and WO96/39385. However, other glycogen phosphorylase inhibitors will be known to those skilled in the art.

Preferred glycogen phosphorylase inhibitors include compounds having the Formula IC

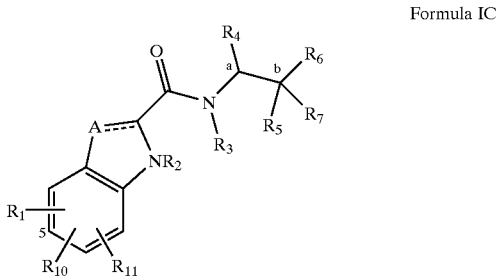

Formula IC and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)- when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy($C_1$–$C_4$)alkyl, thien-2- or -3-yl($C_1$–$C_4$)alkyl or fur-2- or -3-yl ($C_1$–$C_4$)alkyl wherein said $R_4$ rings are mono-, di- or tri-substituted independently on carbon with H, halo, ($C_1$–$C_4$) alkyl, ($C_1$–$C_4$)alkoxy, trifluoromethyl, hydroxy, amino or cyano; or $R_4$ is pyrid-2-, -3- or -4-yl($C_1$–$C_4$)alkyl, thiazol-2-, -4- or -5-yl($C_1$–$C_4$)alkyl, imidazol -1-, -2-, -4- or -5-yl($C_1$–$C_4$) alkyl, pyrrol-2- or -3-yl($C_1$–$C_4$)alkyl, oxazol-2-, -4- or -5-yl-($C_1$–$C_4$)alkyl, pyrazol-3-, -4- or -5-yl($C_1$–$C_4$)alkyl, isoxazol-3-, -4- or -5-yl($C_1$–$C_4$)alkyl, isothiazol-3-, -4- or -5-yl($C_1$–$C_4$)alkyl, pyridazin-3- or -4-yl-($C_1$–$C_4$)alkyl, pyrimidin-2-, -4-, -5- or -6-yl($C_1$–$C_4$)alkyl, pyrazin-2- or -3-yl($C_1$–$C_4$)alkyl or 1,3,5-triazin-2-yl($C_1$–$C_4$)alkyl, wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono-or di-substituents are bonded to carbon;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N, N-($C_1$–$C_4$)alkylamino($C_1$–$C_4$)alkoxy, carboxy($C_1$–$C_4$) alkoxy, ($C_1$–$C_5$)alkoxy-carbonyl($C_1$–$C_4$)alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, ($C_1$–$C_4$) alkyl, ($C_1$–$C_4$)alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is H, ($C_1$–$C_8$)alkyl, hydroxy, ($C_1$–$C_8$)alkoxy, methylene-perfluorinated($C_1$–$C_8$)alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted $(C_1–C_5)$alkyl, wherein said substituents are independently H, hydroxy, amino, mono-N- or di-N,N-$(C_1–C_5)$alkylamino; or $R_9$ is mono- or di-substituted $(C_1–C_5)$alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with $(C_1–C_6)$alkyl, benzyl, benzoyl or $(C_1–C_6)$alkoxycarbonyl and wherein the $R_9$ rings are optionally mono-substituted on carbon with halo, $(C_1–C_4)$alkyl, $(C_1–C_4)$alkoxy, hydroxy, amino, or mono-N- and di-N,N $(C_1–C_5)$alkylamino provided that no quaternized nitrogen is included and there are no nitrogen-oxygen, nitrogen-nitrogen or nitrogen-halo bonds;

$R_{12}$ is piperazin-1-yl, 4-$(C_1–C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1–C_6)$alkoxycarbonylpyrrolidin-1-yl, oxazolidin-3-yl or 2(R)-hydroxymethylpyrrolidin-1-yl; or $R_{12}$ is 3- and/or 4-mono-or di-substituted oxazetidin-2-yl, 2-, 4-, and/or 5-mono- or di-substituted oxazolidin-3-yl, 2-, 4-, and/or 5-mono- or di-substituted thiazolidin-3-yl, 2-, 4-, and/or 5-mono- or di-substituted 1-oxothiazolidin-3-yl, 2-, 4-and/or 5-mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5-mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4- and/or 5-, mono- and/or di-substituted isothiazolidin-2-yl wherein said $R_{12}$ substituents are independently H, halo, $(C_1–C_5)$-alkyl, hydroxy, amino, mono-N- or di-N,N-$(C_1–C_5)$alkylamino, formyl, oxo, hydroxyimino, $(C_1–C_5)$alkoxy, carboxy, carbamoyl, mono-N-or di-N,N-$(C_1–C_4)$alkylcarbamoyl, $(C_1–C_4)$alkoxyimino, $(C_1–C_4)$alkoxymethoxy, $(C_1–C_6)$alkoxycarbonyl, carboxy$(C_1–C_5)$alkyl or hydroxy$(C_1–C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1–C_3)$alkyl or $(C_1–C_3)$alkoxy$(C_1–C_3)$alkyl and $R_6$ is $C(O)NR_8R_9$, $C(O)R_{12}$ or $(C_1–C_4)$alkoxycarbonyl.

Preferred glycogen phosphorylase inhibitors include compounds having the Formula ID

Formula ID and the pharmaceutically acceptable salts and prodrugs thereof wherein the dotted line (---) is an optional bond;

A is —C(H)=, —C(($C_1–C_4$)alkyl)=, —C(halo)= or —N=, when the dotted line (---) is a bond, or A is methylene or —CH(($C_1–C_4$)alkyl)—, when the dotted line (---) is not a bond;

$R_1$, $R_{10}$ or $R_{11}$ are each independently H, halo, cyano, 4-, 6-, or 7-nitro, $(C_1–C_4)$alkyl, $(C_1–C_4)$alkoxy, fluoromethyl, difluoromethyl or trifluoromethyl;

$R_2$ is H;

$R_3$ is H or $(C_1–C_5)$alkyl;

$R_4$ is H, methyl, ethyl, n-propyl, hydroxy$(C_1–C_3)$alkyl, $(C_1–C_3)$alkoxy$(C_1–C_3)$alkyl, phenyl$(C_1–C_4)$alkyl, phenylhydroxy$(C_1–C_4)$alkyl, (phenyl)(($C_1–C_4$)-alkoxy)$(C_1–C_4)$alkyl, thien-2- or -3-yl$(C_1–C_4)$alkyl or fur-2- or -3-yl$(C_1–C_4)$alkyl wherein said $R_4$ rings are mono-, di- or tri-substituted independently on carbon with H, halo, $(C_1–C_4)$alkyl, $(C_1–C_4)$alkoxy, trifluoromethyl, hydroxy, amino, cyano or 4,5-dihydro-1H-imidazol-2-yl; or $R_4$ is pyrid-2-, -3- or -4-yl$(C_1–C_4)$alkyl, thiazol-2-, -4- or -5-yl$(C_1–C_4)$alkyl, imidazol-2-, -4- or -5-yl$(C_1–C_4)$alkyl, pyrrol-2- or -3-yl$(C_1–C_4)$alkyl, oxazol-2-, -4- or -5-yl $(C_1–C_4)$alkyl, pyrazol-3-, -4- or -5-yl$(C_1–C_4)$alkyl, isoxazol-3-, -4- or -5-yl$(C_1–C_4)$alkyl, isothiazol-3-, -4- or -5-yl$(C_1–C_4)$alkyl, pyridazin-3- or -4-yl$(C_1–C_4)$alkyl, pyrimidin-2-, -4-, -5- or -6-yl$(C_1–C_4)$alkyl, pyrazin-2- or -3-yl$(C_1–C_4)$alkyl, 1,3,5-triazin-2-yl$(C_1–C_4)$alkyl or indol-2-$(C_1–C_4)$alkyl, wherein said preceding $R_4$ heterocycles are optionally mono- or di-substituted independently with halo, trifluoromethyl, $(C_1–C_4)$alkyl, $(C_1–C_4)$alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, $(C_1–C_4)$alkyl, $(C_1–C_4)$alkoxy or trifluoromethyl and said mono- or di-substituents are bonded to carbon;

$R_5$ is H;

$R_6$ is carboxy, $(C_1–C_8)$alkoxycarbonyl, benzyloxycarbonyl, $C(O)NR_8R_9$ or $C(O)R_{12}$ wherein $R_8$ is H, $(C_1–C_6)$alkyl, cyclo$(C_3–C_6)$alkyl, cyclo$(C_3–C_6)$alkyl$(C_1–C_5)$alkyl, hydroxy or $(C_1–C_8)$alkoxy; and $R_9$ is H, cyclo$(C_3–C_8)$alkyl, cyclo$(C_3–C_8)$alkyl$(C_1–C_5)$alkyl, cyclo$(C_4–C_7)$alkenyl, cyclo$(C_3–C_7)$alkyl$(C_1–C_5)$alkoxy, cyclo$(C_3–C_7)$alkyloxy, hydroxy, methyleneperfluorinated$(C_1–C_8)$alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally monosubstituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N- or di-N,N-$(C_1-C_5)$alkylamino, cyano, carboxy, or $(C_1-C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N- or di-N,N-$(C_1-C_4)$alkylamino$(C_1-C_4)$alkyl, $(C_1-C_4)$alkoxy$(C_1-C_4)$alkyl, amino, mono-N- or di-N,N-$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c] isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N- or di-N,N-$(C_1-C_5)$alkylamino, formyl, carboxy, carbamoyl, mono-N- or di-N,N-$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl $(C_1-C_5)$alkyl, mono-N- or di-N,N-$(C_1-C_5)$alkylcarbamoyl $(C_1-C_5)$alkyl, hydroxy$(C_1-C_5)$alkyl, $(C_1-C_4)$alkoxy $(C_1-C_4)$alkyl, amino$(C_1-C_4)$alkyl, mono-N- or di-N,N-$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on nonaromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-Cyano and $R_4$ is (phenyl)(hydroxy)$(C_1-C_4)$alkyl, (phenyl) $((C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when both $R_8$ and $R_9$ are n-pentyl, $R_1$ is 5-chloro, 5-bromo, 5-Cyano, 5$(C_1-C_5)$alkyl, 5$(C_1-C_5)$alkoxy or trifluoromethyl;

with the proviso that when $R_{12}$ is 3,4-dihydroisoquinol-2-yl, said 3,4-dihydroisoquinol-2-yl is not substituted with carboxy$((C_1-C_4)$alkyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of NHR$_9$; and with the proviso that when $R_6$ is carboxy and $R_1$, $R_{10}$, $R_{11}$ and $R_5$ are all H, then $R_4$ is not benzyl, H, (phenyl)(hydroxy) methyl, methyl, ethyl or n-propyl.

In general an effective dosage for the pharmacological combination compositions of this invention, for example the ischemic damage reducing activities of combinations containing the glycogen phosphorylase inhibitor compounds of this invention, is in the range of 0.005 to 50 mg/kg/day, preferably 0.01 to 25 mg/kg/day and most preferably 0.1 to 15 mg/kg/day.

The compounds of the present invention inhibit the sodium/proton (Na+/H+) exchange transport system and hence are useful as a therapeutic or prophylactic agent for diseases caused or aggravated by the acceleration of the sodium/proton (Na+/H+) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [(e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema. The compounds of this invention can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries.

Preferably, the compounds of this invention can be used as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the compounds of this invention can be used as agents for myocardial protection in patients presenting with ongoing cardiac (acute coronary syndromes, e.g. myocardial infarction or unstable angina) or cerebral ischemic events (e.g. stroke).

Preferably, the compounds of this invention can be used as agents for chronic myocardial protection in patients with diagnosed coronary heart disease (e.g. previous myocardial infarction or unstable angina) or patients who are at high risk for myocardial infarction (age greater than 65 and two or more risk factors for coronary heart disease).

In addition to this, the compounds of this invention are notable for their strong inhibitory effect on the proliferation of cells, for example the proliferation of fibroblast cells and the proliferation of the smooth muscle cells of the blood vessels. For this reason, the compounds of this invention are valuable therapeutic agents for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the compounds of the present invention as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of the compounds of this invention in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the anti-arrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

Measurement of Human NHE-1 Inhibitory Activity

Methodologies for measurement of human NHE-1 activity and inhibitor potency are based on those published by Watson et al., Am. J. Physiol., 24:G229–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 min at 37° C. with the pH sensitive fluorescent probe BCECF (5 μM; Molecular Probes, Eugene, Oreg.). BCECF loaded cells are incubated for 30 min at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5) ±test compound, and NHE-mediated recovery of intracellular pH is monitored as the subsequent time-dependent increase BCECF fluorescence. The potency of human NHE-1 inhibitors is calculated as the concentration that reduces recovery of intracellular pH by 50% ($IC_{50}$). Under these conditions reference NHE inhibitors amiloride and HOE-642 had $IC_{50}$ values for human NHE-1 of 50 μM and 0.5 μM, respectively.

As background information, it is noted that brief periods of myocardial ischemia followed by coronary artery reperfusion protects the heart from subsequent severe myocardial ischemia (Murry et al., Circulation 74:1124–1136, 1986).

The therapeutic effects of the compounds of this invention in preventing heart tissue damage resulting from an ischemic insult can be demonstrated in vitro along lines presented in Liu etal. (Cardiovasc. Res., 28:1057–1061, 1994), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described below demonstrates that a test compound (i.e., a compound as claimed herein) can also pharmacologically induce cardioprotection, i.e., reduced myocardial infarct size, when administered to a rabbit isolated heart. The effects of the test compound are compared to ischemic preconditioning and the A1/A3 adenosine agonist, APNEA ($N^6$-[2-(4-aminophenyl)ethyl]adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure ≦10 mmHg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at about 200 bpm for the remainder of the experiment. Ischemic preconditioning is induced by total cessation of cardiac perfusion (global ischemia) for 5 min, followed by reperfusion for 10 min. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts which receive test compounds do not undergo the period of ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$M) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −20° C. The next day, the heart is sliced into 2 mm transverse sections from the apex to the top of the ventricles. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/AAR). All data are expressed as mean ±SE and compared statistically using a Mann-Whitney non-parametric test with a Bonferroni correction for multiple comparisons. Significance is considered as $p<0.05$.

The results from the above in vitro test demonstrate that compounds of this invention induce significant cardioprotection relative to the control group.

The therapeutic effects of the compounds of this invention in preventing heart tissue damage otherwise resulting from an ischemic insult can also be demonstrated in vivo along lines presented in Liu et al. (Circulation, Vol. 84:350–356, 1991) as described specifically herein. The in vivo assay tests the cardioprotection of the test compound relative to the control group which receives saline vehicle. Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether compounds can pharmacologically induce cardioprotection, i.e., reduced myocardial infarct size, when parenterally administered to intact, anesthetized rabbits. The effects of the compounds of this invention can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allows the affected area to reperfuse. Myocardial ischemia is evidenced by regional cyanosis; reperfusion is evidenced by reactive hyperemia.

Protocol: Once arterial pressure and heart rate have been stable for at least 30 minutes the test is started. Ischemic preconditioning is induced by occluding the coronary artery for 5 min followed by a 10 min reperfusion. Pharmacological preconditioning is induced by infusing test compound over, for example 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test compound and PIA are dissolved in saline or other suitable vehicle and delivered at 1 to 5 mg/kg, respectively.

Staining (Liu et al., Circulation 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent zinc cadmium sulphate particles (1–10 $\mu$m) Duke Scientific Corp. (Palo Alto, Calif.) is infused with the perfusate to stain all of the myocardium except the area at risk (nonfluorescent ventricle). The hearts are then quickly frozen and stored overnight at −20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (% IA/AAR). All data are expressed as Mean±SEM and compared statistically using single factor ANOVA or Mann Whitney non parametric test. Significance is considered as $p<0.05$.

The compounds of this invention can be tested for their utility in reducing or preventing ischemic injury in non-cardiac tissues, for example, the brain, or the liver, utilizing procedures reported in the scientific literature. The compounds of this invention in such tests can be administered by the preferred route and vehicle of administration and at the preferred time of administration either prior to the ischemic episode, during the ischemic episode, following the ischemic episode (reperfusion period) or during any of the below-mentioned experimental stages.

The benefit of the invention to reduce ischemic brain damage can be demonstrated, for example, in mammals using the method of Park, et al (Ann. Neurol. 1988; 24:543–551). According to the procedure of Park, et al., adult male Sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2$>90 mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a 40% formaldehyde, glacial acetic acid and absolute methanol solution (FAM; 1:1:8, v/v/v), then the animals are decapitated and the head is stored in fixative for 24 hours. The brain is then removed, dissected, embedded in paraffin wax, and sectioned (approximately 100 sections 0.2 mm per brain). The sections are then stained with hematoxylin-eosin or with a combination of cresyl violet and Luxol fast blue, and examined by light microscopy to identify and quantitate the ischemic damage using a precalibrated image analyzer. The ischemic volumes and areas are expressed in absolute units ($mm^3$ and $mm^2$) and as a percentage of the total region examined. The effect of the compositions and methods of this invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the invention to reduce ischemic brain damage include those described by Nakayama, et al. in Neurology 1988,38:1667–1673; Memezawa, et al. in Stroke 1992,23:552–559; Folbergrova, et al. in Proc. Natl. Acad. Sci 1995,92:5057–5059; and Gotti, et al. in Brain Res. 1990,522:290–307.

The benefit of the compounds, compositions and methods of this invention to reduce ischemic liver damage can be demonstrated, for example, in mammals using the method of Yokoyama, et al. (Am. J. Physiol. 1990; 258:G564–G570). According to the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MgSO_4$, 1.2 $KH_2PO_4$, 0.05 EDTA, and 11 mM glucose, plus 300 U heparin). The pH of the perfusate is maintained at 7.4 by gassing the buffer with 95% $O_2$-5% $CO_2$. Each liver is perfused at a flow rate of 20 ml/min in a single-pass manner for a 30 min washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 min of the 2 hour reperfusion period. The perfusate samples are assayed for the appearance of hepatocellular enzymes, for example, aspartate amino-transferase (AST), alanine amino-transferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995; 22:539–545). The effect of the compounds, compositions and methods of this invention in reducing ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods and parameters which could alternatively be utilized to demonstrate the benefit of the compositions and methods of this invention in reducing ischemic liver damage include those described by Nakano, et al. (Hepatology 1995; 22:539–545).

Aldose Reductase Inhibitor Assays

Male Sprague-Dawley rats are rendered diabetic by injection of streptozocin at 55 mg/kg, i.v., in pH 4.5 citrate buffer. They are fed ad libitum in controlled conditions of housing, temperature and lighting. After five weeks of diabetes, the rats are anesthetized with an overdose of pentobarbital, and tissues are rapidly removed and analyzed for sorbitol and fructose.

Sorbitol levels are analyzed according to the method of Donald M. Eades et al., "Rapid Analysis of Sorbitol, Galactitol, Mannitol and Myoinositol Mixtures From Biological Sources", *Journal of Chromatography,* 490, 1–8, (1989).

Fructose in rat tissues is enzymatically measured using a modification of the method of Ameyama (*Methods in Enzymology,* 89:20–29, 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contains 0.1 ml neutralized 6% perchloric acid nerve extract in a final volume of 1.5 ml. Following incubation for 60 minutes at room temperature in a closed drawer, sample fluorescence is determined at excitation=560 nm, emission=580 nm with slits of 5 mm each in a Perkin-Elmer model 650-40 fluorescence spectrophotometer. Fructose concentrations are calculated by comparison with a series of known fructose standards.

Glycogen Phosphorylase Inhibitor Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP and HMGP cDNAs are expressed from plasmid pKK233–2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756). The method described by Crerar, et al. (J. Biol. Chem. 270:13748–13756) for the expression of HBGP is as follows: the HBGP cDNA can be expressed from plasmid pTACTAC in *E. Coli* strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40× volume of LB/amp media containing 250 μM isopropyl-1-thio-β-D-galactoside (IPTG), 0.5 mM pyridoxine and 3 mM MgCl$_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium are infected at a multiplicity of infection (moi) of 0.5 and at a cell density of 2×10$^6$ cells/ml. After growth for 72 hours at 27° C., cells are centrifuged, and the cell pellets frozen at −70° C. until needed for purification. *Purification of Glycogen Phosphorylase expressed in E. coli*

The *E. coli* cells in pellets described above are resuspended in 25 mM β-glycerophosphate (pH 7.0) with 0.2 mM DTT, 1 mM MgCl$_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The *E. coli* cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. Journal of Chromatography (1992) 584, 77–84.). 500 mL of the filtered soluble fraction of cell lysates (prepared from approximately 160–250 g of original cell pellet) are loaded onto a 130 mL column of IMAC Chelating-Sepharose (Pharmacia LKB Biotechnology, Piscataway, N.J.) which has been charged with 50 mM CuCl$_2$ and 25 mM β-glycerophosphate, 250 mM NaCl and 1 mM imidazole at pH 7 equilibration buffer. The column is washed with equilibration buffer until the A$_{280}$ returns to baseline. The sample is then eluted from the column with the same buffer containing 100 mM imidazole to remove the bound GP and other bound proteins. Fractions containing the GP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'-AMP-Sepharose Chromatography

The desalted pooled GP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the A$_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity (described below) and visualizing the M$_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl$_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 3 μg/mL DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 μg/mL leupeptin and 1.0 μg/mL pepstatin A. The sample is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis[2-Hydroxyethyl]-2-aminoethanesulfonic acid, 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the following procedure.

GP Reaction with Immobilized Phosphorylase Kinase

Phosphorylase kinase (Sigma Chemical Company, St. Louis, Mo.) is immobilized on Affi-Gel 10 (BioRad Corp., Melvile, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM $CaCl_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel beads. NaATP is added to 5 mM and $MgCl_2$ to 6 mM. The resulting mixture is mixed gently at 25° C. for 30 to 60 minutes. The sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total HLGPa} = \frac{\text{HLGP activity} - \text{AMP}}{\text{HLGP activity} + \text{AMP}}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to *E. coli* derived GPa and GPb standards that are run in parallel on the same gels as the experimental samples.

B) GPa Activity Assay

The disease/condition treating/preventing activities described herein of the glycogen phosphorylase inhibitor compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions can be run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23, 1711–1717] modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 μl of this stock is added to 80 μl of Buffer A containing 0.47 mg/mL glycogen, 9.4 mM glucose, 0.63 mM of the oxidized form of nicotinamide adenine dinucleotide phosphate (NADP+). The compounds to be tested are added as 5 μL of solution in 14% dimethylsulfoxide (DMSO) prior to the addition of the enzymes. The basal rate of GPa enzyme activity in the absence of inhibitors is determined by adding 5 μL of 14% DMSO and a fully-inhibited rate of GPa enzyme activity is obtained by adding 20 μL of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 μg GPa is diluted to 1 mL in Buffer B (described hereinafter). Buffer B is at pH 7.2 and contains 50 mM HEPES, 100 mM KCl, 2.5 mM EGTA, 2.5 mM $MgCl_2$ and 0.5 mM dithiothreitol. 20 μL of this stock is added to 80 μL of Buffer B with 1.25 mg/mL glycogen, 9.4 mM glucose, and 0.63 mM glucose-1-phosphate. The compounds to be tested are added as 5 μL of solution in 14% DMSO prior to the addition of the enzyme. The basal rate of GPa enzyme activity in the absence of added inhibitors is determined by adding 5 µL of 14% DMSO and a fully-inhibited rate of GPa enzyme activity is obtained by adding 20 µL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 µL of 10 mg/mL ammonium molybdate, 0.38 mg/mL malachite green in 1 N HCl is added to 100 µL of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

Administration of the compounds of this invention can be via any method which delivers a compound of this invention preferentially to the desired tissue (e.g., liver and/or cardiac tissues). These methods include oral routes, parenteral, intraduodenal routes, etc. Generally, the compounds of the present invention are administered in single (e.g., once daily) or multiple doses or via constant infusion.

The compounds of this invention are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The active compound is therefore usefully employed prophylactically to prevent, i.e. (prospectively or prophylactically) to blunt or stem, tissue damage (e.g., myocardial tissue) in patients who are at risk for ischemia (e.g., myocardial ischemia).

Generally, the compounds of this invention are administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Thus, for example, in one mode of administration the compounds of this invention may be administered just prior to surgery (e.g., within twenty-four hours before surgery for example cardiac surgery) during or subsequent to surgery (e.g., within twenty-four hours after surgery) where there is risk of myocardial ischemia. The compounds of this invention may also be administered in a chronic daily mode.

An amount of the compounds of this invention is used that is effective for ischemic protection. A preferred dosage is about 0.001 to 100 mg/kg/day of the compound of this invention. An especially preferred dosage is about 0.01 to 50 mg/kg/day of the compound of this invention.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain for example 0.0001%–95% of the compound(s) of this invention. In any event, the composition or formulation to be administered will contain a quantity of a compound(s) according to the invention in an amount effective to treat the disease/condition of the subject being treated.

The two different compounds of this combination of this invention can be co-administered simultaneously or sequentially in any order, or as a single pharmaceutical composition comprising a compound of Formula I and an aldose reductase inhibitor as described above or a glycogen phosphorylase inhibitor as described above or a cardiovascular agent.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |

-continued

| Formulation 4: Suspensions | |
|---|---|
| Ingredient | Quantity (mg/5 ml) |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient | 25 mg–10,000 mg |
| Isotonic saline | 1,000 mL |

The solution of the above ingredients is intravenously administered to a patient.

The active ingredient above may also be a combination of agents.

General Experimental Procedures

NMR spectra were recorded on a Varian XL-300 (Varian Co., Palo Alto, Calif.) a Bruker AM-300 spectrometer (Bruker Co., Billerica, Mass.) or a Varian Unity 400 at about 23° C. at 300 or 400 MHz for proton. Chemical shifts are expressed in parts per million downfield from trimethylsilane. The peak shapes are denoted as follows: s, singlet; d, doublet; t, triplet, q, quartet; m, multiplet; bs,=broad singlet. Resonances designated as exchangeable did not appear in a separate NMR experiment where the sample was shaken with several drops of $D_2O$ in the same solvent. Atmospheric pressure chemical ionization mass spectra (APCIMS) were obtained on a Fisons Platform II Spectrometer. Chemical ionization mass spectra (CIMS) were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions and 1:1 for $^{79}Br/^{81}Br$-containing ions) and M is based on $^{35}Cl$ and $^{79}Br$. In some cases only representative $^1H$ NMR and APCIMS peaks are given.

Column chromatography was performed with either Baker Silica Gel (40 μm) (J. T. Baker, Phillipsburg, N.J.) or Silica Gel 60 (EM Sciences, Gibbstown, N.J.) in glass columns or in Flash 40™ or Flash 12™ (Biotage) (Charlottesville, Va.) columns under low nitrogen pressure. Radial Chromatography was performed using a Chromatron, (Harrison Research) (Palo Alto, Calif.) Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 50° C. Reactions conducted at "0–20° C." or "0–25° C." were conducted with initial cooling of the vessel in an insulated ice bath which was allowed to warm to room temperature over several hours. The abbreviation "min" and "h" stand for "minutes" and "hours" respectively.

Reference to the hydrochloride salt in the Example names below includes mono-or di-salts as appropriate in the particular Example.

EXAMPLE 1

Ethyl 5-methyl-1-phenyl-1H-1,2,3-triazole-4-carboxylate

Titanium tetrachloride (0.28 mL, 2.56 mmol) was added to a solution of ethyl diazoacetoacetate (0.35 mL, 2.56 mmol) and aniline (0.47 mL, 5.12 mmol) in 5 mL of dichloroethane. After heating at reflux for 16 hours, the solution was quenched with an aqueous 2 N KOH solution, and 10 mL each of hexanes and diethyl ether were added. The separated organic phase was washed with water, dried over sodium sulfate, filtered and concentrated in vacuo. The product was purified by silica gel chromatography eluting with 0–15% ethyl acetate in hexanes to provide 168 mg of the title compound.

$^1H$ NMR (CD$_3$OD) δ 1.4 (t, 3H), 2.6 (s, 3H), 4.4 (q, 2H), 7.5–7.6 (m, 2H), 7.6–7.7 (m, 3H).

EXAMPLE 2

Methyl 4-methyl-5-phenyl-4H-1,2,4-triazole-3-carboxylate

N-Methyl benzamide (5 g, 37 mmol) was converted to the thioamide by treatment with Lawesson's reagent (10 g, 25 mmol) in dimethoxyethane (100 mL) at 60° C. for 4 hours.

After an aqueous extractive work-up with methylene chloride, drying over sodium sulfate, and filtering, the organic phases were concentrated in vacuo to afford 2.68 g of the thioamide as a yellow solid. This material (2.86 g, 17.75 mmol) was treated directly with methyl iodide (3.87 mL, 62 mmol) in acetone (100 mL). After stirring overnight at room temperature, the mixture was concentrated in vacuo to afford 2.48 g of the N,S-dimethylisothiobenzamide hydroiodide as a yellow solid. This material (2.48 g, 8.46 mmol) was dissolved in 50 mL of methanol and cooled in an ice bath as anhydrous hydrazine (0.518 mL, 16.51 mmol, dissolved in 10 mL of methanol) was slowly added to the solution. While cooling in an ice water bath, the mixture was stirred for 2.5 h and ether (about 200 mL) was added to form a precipitate. The resulting slurry was stirred for 3 additional hours before the solid was collected by filtration and rinsed with ether, to afford 2.15 g of the N-methyl benzamidrazone hydroiodide as a white solid.

$^1$H NMR (CD$_3$OD) δ 2.95 (s, 3H), 7.6 (m, 4H), 7.7 (m, 1H).

The preceding N-methyl benzamidrazone hydroiodide (1 g, 3.61 mmol) was dissolved in 5 mL of pyridine and treated with methyl oxalyl chloride (0.89 mL, 9.6 mmol). After the exothermic addition, the reaction mixture was stirred at room temperature overnight before being concentrated in vacuo. The resulting residue was combined with 10 mL of water and extracted with ethyl acetate (3×75 mL). The combined organic phases were washed with water (2×25 mL), dried over sodium sulfate, filtered, and concentrated in vacuo to give a yellow solid which was purified by silica gel chromatography eluting with 5% methanol in methylene chloride to afford 200 mg of the title compound.

$^1$H NMR (CD$_3$OD) δ 3.9 (s, 3H), 4.0 (s, 3H), 7.6 (m, 3H), 7.7 (m, 2H).

The title compounds of Examples 3A–3T were prepared using procedures analogous to that described in Klinsberg, E. *Synthesis* 1972, 475.

EXAMPLE 3A

5-Methyl-2-(4-methoxyphenyl)-2H-1,2,3-triazole-4-carboxylic acid

Acetoacetanilide (25.0 g, 0.14 mol) and sodium nitrite (12.65 g, 0.18 mol) were dissolved in aqueous sodium hydroxide solution (140 ml, 1 N) and the resulting solution was added dropwise over 20 min to an aqueous solution of sulfuric acid (120 ml conc. H$_2$SO$_4$ in 950 ml water) cooled in an ice bath. The reaction mixture was stirred at 0° C. for 30 min, then the precipitate was filtered and washed with water to yield 2-hydroxyiminoacetanilide (22.64 g., 78% yield) as a pale yellow solid.

Sodium methoxide (0.89 g, 0.017 mol) was added to a solution of 4-methoxyphenylhydrazine hydrochloride (2.89 g, 0.016 mol) in 10 ml ethanol and after 5 min the mixture was filtered and the filtrate added to a warm solution of 2-hydroxyiminoacetoacetanilide (3.25 g, 0.0158 mol) in 5 ml ethanol. The resulting solution was briefly heated to reflux, then allowed to cool to room temperature, whereupon a precipitate formed. The precipitate was filtered and washed with 2:1 hexane/ethyl acetate to yield 2-hydroxyimino-3-(4-methoxyphenyl)hydrazonobutanoic acid anilide as a yellow solid (3.16 g, 61% yield).

2-Hydroxyimino-3-(4-methoxyphenyl) hydrazonobutanoic acid anilide (3.16 g, 0.01 mol) was added over a 2 min period to a refluxing solution of potassium hydroxide (3.2 g, 0.05 mol) in 12 ml 2-ethoxyethanol. The reaction mixture was refluxed for 15 min, then cooled to room temperature. The precipitate that formed was filtered and washed with diethyl ether. The solid was dissolved in 15 ml water and the resulting solution was acidified with dilute aqueous hydrochloric acid. The aqueous solution was extracted with 3×20 ml ethyl acetate and the combined ethyl acetate extracts were washed with 40 ml water and 40 ml brine, dried (anhydrous sodium sulfate) and concentrated in vacuo to yield the title compound (0.84 g) as a reddish solid. By a similar treatment of the solids that formed in the filtrate from the ether wash, a further 0.805 g of the product was obtained (1.65 g total yield, 73% yield).

$^1$H NMR (CD$_3$OD) δ 2.58 (s, 3H); 3.83 (s, 3H); 6.9–7.0 (m, 2H); 7.74 (d, 1H); 7.99 (d, 1H).

The title compounds of Examples 3B–3T were prepared using procedures analogous to that used for Example 3A.

EXAMPLE 3B

5-Methyl-2-(4-sulfamoylphenyl)-2H-1,2,3-triazole-4-carboxylic acid

21% yield.

$^1$H NMR (CD$_3$OD) δ 2.59 (s, 3H); 8.05 (d, 2H); 8.25 (d, 2H).

EXAMPLE 3C

5-Methyl-2-(2-methoxyphenyl)-2H-1,2,3-triazole-4-carboxylic acid

98% yield.

$^1$H NMR (CDCl$_3$) δ 2.33 (s, 3H); 3.87 (s, 3H); 6.97–7.14 (m, 2H); 7.3–7.55 (m, 2H).

EXAMPLE 3D

5-Methyl-2-(4-methylsulfonylphenyl)-2H-1,2,3-triazole-4-carboxylic acid

50% yield.

$^1$H NMR (CDCl$_3$) δ 2.6 (s, 3H); 3.06 (s, 3H); 8.01 (d, 2H); 8.29 (d, 2H).

EXAMPLE 3E

5-Methyl-2-(3-methoxyphenyl)-2H-1,2,3-triazole-4-carboxylic acid

46% yield.

$^1$H NMR (CDCl$_3$) δ 2.34 (s, 3H); 3.82 (s, 3H); 6.92 (m, 1H); 7.36 (t, 1H); 7.61–7.68 (m, 2H).

EXAMPLE 3F

5-Methyl-2-(5-quinolinyl)-2H-1,2,3-triazole-4-carboxylic acid

67% yield.

$^1$H NMR (DMSO-d$_6$) δ 2.56 (s, 3H); 7.67 (m, 1H); 7.89–7.99 (m, 2H); 8.2 (d, 1H); 8.55 (d, 1H); (9.01, s, 1H).

EXAMPLE 3G

5-Methyl-2-(5-isoquinolinyl)-2H-1,2,3-triazole-4-carboxylic acid

31% yield.

$^1$H NMR (DMSO-d$_6$) δ 2.57 (s, 3H); 7.85 (t, 1H); 8.09 (d, 1H); 8.17 (d, 1H); 8.34 (d, 1H); 8.63 (d, 1H); 9.48 (s, 1H).

EXAMPLE 3H

5-Methyl-2-(p-tolyl)-2H-1,2,3 triazole-4-carboxylic acid

44% yield $^1$H NMR (400 MHz, CDCl$_3$) δ 2.35 (s, 3H), 2.50(s, 3H), 7.36(d, J=8, 2H), 7.87(d, J=8, 2H), 13.42(s, 1H).

APCIMS 216 [M−1]$^-$

EXAMPLE 3I 2-(4-Chlorophenyl)-5-methyl-2H-1,2,3-triazole-4-carboxylic acid

22% yield $^1$H NMR (400 MHz, CDCl$_3$) δ 2.5(s, 3H), 7.41(d, J=8, 2H), 8.00(d, J=8, 2H), 13.53(s, 1H).

APCIMS 236 [M−1]$^-$

EXAMPLE 3J 2-(3,4-Dichlorophenyl)-5-methyl-2H-1,2,3-triazole-4-carboxylic acid 14% yield $^1$H NMR (400 MHz, CDCl$_3$) δ 2.48 (s, 3H), 7.43(d, J=8, 1H), 7.86(dd, J=2.4, 8.8, 1H), 8.15(d, J=2.4, 1H).

APCIMS 271 [M−1]$^-$

EXAMPLE 3K 2,5-Diphenyl-2H-1,2,3-triazole-4-carboxylic acid

29% yield $^1$H NMR (400 MHz, DMSO) δ 7.48(m, 4H) 7.60(m, 2H), 7.88(m, 2H), 8.10(m, 2H), 13.61 (s, 1H).

APCIMS 264 [M−1]$^-$

EXAMPLE 3L 2-(3,5-Dichlorophenyl)-5-methyl-2H-1,2,3-triazole-4-carboxylic acid 40% yield $^1$H NMR (400 MHz, DMSO) δ 2.47(s, 3H), 7.67(d, J=1.6, 1H), 7.92(d, J=1.6, 2H).

APCIMS 270 [M−1]$^-$

EXAMPLE 3M

5-Methyl-2-(m-tolyl)-2H-1,2,3-triazole-4-carboxylic acid

66% yield $^1$H NMR (400 MHz, DMSO) δ 2.37 (s, 3H), 2.47(s, 3H), 7.23 (m, 1H), 7.41(m, 1H), 7.77 (m, 2H), 13.40(bs, 1H).

APCIMS 216 [M−1]$^-$

EXAMPLE 3N 2-(3-Chlorophenyl)-5-methyl-2H-1,2,3-triazole-4-carboxylic acid

62% yield $^1$H NMR (400 MHz, DMSO) δ 2.50 (s, 3H), 7.51 (m, 1H), 7.59 (m, 1H), 7.96 (m, 2H).

APCIMS 236 [M−1]$^-$

EXAMPLE 3O

2-Phenyl-5-(n-propyl)-2H-1,2,3-triazole-4-carboxylic acid

20% yield.

$^1$H NMR (400 MHz, CD3OD) δ 1.00 (t, J=7, 3H), 1.78 (m, 2H), 3.13 (m, 2H), 7.42 (m, 1H), 7.52 (m, 2H), 8.07(m, 2H).

APCIMS 230 [M−1]$^-$

EXAMPLE 3P

2-Phenyl-5-ethyl-2H-1,2,3-triazole-4-carboxylic acid

63% yield $^1$H NMR (400 MHz, CD$_3$OD) δ 1.33(t, J=7.6, 3H), 3.15 (m, 2H), 7.41 (m, 1H), 7.52 (m, 2H), 8.08 (m, 2H).

APCIMS 216 [M−1]$^-$

EXAMPLE 3Q

5-Methyl-2-(3-trifluoromethylphenyl)-2H-1,2,3-triazole-4-carboxylic acid

37% yield $^1$H NMR (400 MHz, CD$_3$OD) δ 2.57(s, 3H), 7.71(m, 2H), 8.32(m, 2H).

APCIMS 270 [M−1]$^-$

EXAMPLE 3R 2-(1-Naphthalenyl)-5-methyl-2H-1,2,3-triazole-4-carboxylic acid

54% yield $^1$H NMR (400 MHz, DMSO-d$_6$) δ 2.57 (s, 3H), 7.64 (m, 3H), 7.82(d, J=7.2, 1H), 7.94(dd, J=2, 5.6, 1H), 8.12 (m, 2H).

APCIMS 252 [M−1]$^-$

EXAMPLE 3S

5-Methyl-2-(8-quinolinyl)-2H-1,2,3-triazole-4-carboxylic acid

24% yield $^1$H NMR (400 MHz, CD$_3$OD) δ 2.63(s, 3H), 7.64(dd, J=4.4, 8, 1H), 7.76 (t, J=7.8, 1H), 8.00(dd, J=1.4, 7.4, 1H), 8.18(dd, J=1.2, 8.4, 1H), 8.50(dd, J=1.6, 8.4, 1H), 8.88(dd, J=1.6, 4, 1H).

APCIMS 253 [M−1]$^-$

EXAMPLE 3T 2-(3-Bromophenyl)-5-methyl-2H-1,2,3-triazole-4-carboxylic acid

44% yield $^1$H NMR (400 MHz, DMSO-d$_6$) δ 2.47 (s, 3H), 7.51 (t, J=8, 1H), 7.64 (dd, J=8.2,1, 1H), 7.98 (dt, J=8.0,1, 1H), 8.10 (d, J=1, 1H), 13.54 (bs, 1H).

APCIMS 236 [M−1]$^-$

EXAMPLE 4

5-(N,N-Dimethylcarbamoyl)-2-phenyl-2H-1,2,3-triazole-4-carboxylic acid

A solution of 5-methyl-2-phenyl-2H-1,2,3-triazole-4-carboxylic acid (10.2 g, 50 mmol) and NaOH (17.6 g, 440 mmol) in water (375 mL) at 23° C. was treated with KMnO$_4$ (30.8 g, 195 mmol). The resulting solution was heated at reflux for 17 h, cooled to 23° C. and treated with ethanol (50 mL). The resulting mixture was filtered to remove MnO$_2$. The filtrate was acidified with HCl (conc.) to pH 1. The resulting white solid was collected by filtration. The filtrate was concentrated to half volume and more solid was collected by filtration. The two combined batches of solid were dried in vacuo to afford 11.1 g (95%) of 2-phenyl-2H-1,2,3-triazole-4,5-dicarboxylic acid.

A suspension of 2-phenyl-2H-1,2,3-triazole-4,5-dicarboxylic acid (2.00 g, 8.58 mmol) in methanol (50 mL) at 23° C. was treated with H$_2$SO$_4$ (conc., 0.477 mL, 8.58 mmol). The mixture was refluxed for 15 h, cooled to 23° C. and partitioned between NaHCO$_3$ (sat. aq. sol.) and EtOAc. The aqueous layer was extracted with another portion of EtOAc. The combined organic extracts were washed with brine, dried over MgSO$_4$ and concentrated in vacuo to afford 1.61 g (72%) of dimethyl 2-phenyl-2H-1,2,3-triazole-4,5-dicarboxylate.

$^1$H NMR (400 MHz, CDCl$_3$) δ 4.01 (s, 6H), 7.49 (m, 3H), 8.13 (m, 2H).

APCIMS 262 [M+1]$^+$

A solution of dimethyl 2-phenyl-2H-1,2,3-triazole-4,5-dicarboxylate (0.522 g, 2.00 mmol) in methanol (40 mL) at 23° C. was treated with a solution of KOH (0.236 g, 4.20 mmol) in methanol (5 mL). The resulting solution was stirred at 23° C. for 17 h and partitioned between NaHCO$_3$ (sat. aq. sol.) and ether. The aqueous layer was washed with ether and acidified carefully to pH 1 with HCl (conc.). The resulting mixture was extracted with EtOAc. The organic extract was washed with brine, dried over MgSO$_4$ and concentrated in vacuo. The residue was purified by radial chromatography (2 mm plate, CH$_2$Cl$_2$-methanol-acetic acid 90:10:1) to afford 0.42 g (85%) of 5-methoxycarbonyl-2-phenyl-2H-1,2,3-triazole-4-carboxylic acid.

A solution of 5-methoxycarbonyl-2-phenyl-2H-1,2,3-triazole-4-carboxylic acid (0.203 g, 0.82 mmol) in dry DMF (3 mL) at 23° C. was treated with carbonyldiimidazole (0.146 g, 0.90 mmol). The resulting mixture was stirred for 1.5 h at 23° C., cooled to 0° C. and treated with dimethylamine (2.0 M, in THF, 2.05 mL, 4.10 mmol). The resulting mixture was allowed to warm to 23° C. over 16 h and concentrated in vacuo. The residue was partitioned between water and EtOAc. The aqueous layer was extracted with an additional portion of EtOAc. The combined organic extracts were washed with HCl (1 M), brine, NaHCO$_3$ (sat. aq. sol.) and brine, dried over MgSO$_4$ and concentrated in vacuo. The residue was purified by filtering it through a silica gel plug (EtOAc-hexanes 50:50) to afford 0.201 g (89%) of methyl 5-(N,N-dimethylcarbamoyl)-2-phenyl-2H-1,2,3-triazole-4-carboxylate.

A solution of methyl 5-(N,N-dimethylcarbamoyl)-2-phenyl-2H-1,2,3-triazole-4-carboxylate (0.195 g, 0.71 mmol) in THF (3.6 mL) at 23° C. was treated with LiOH (1 M aq., 3.6 mL, 3.6 mmol). The resulting suspension was stirred for 15 min at 23° C. and partitioned between ether and water. The aqueous layer was acidified to pH 1 with HCl (conc.). The resulting white solid was collected by filtration, washed with water, and air-dried to provide 0.164 g (89%) of 5-(N,N-dimethylcarbamoyl)-2-phenyl-2H-1,2,3-triazole-4-carboxylic acid.

$^1$H NMR (400 MHz, CDCl$_3$) δ 3.26 (bs, 3H), 3.65 (bs, 3H), 7.50 (bs, 3H), 8.13 (bs, 2H).

APCIMS 261 [M+1]$^+$

EXAMPLE 5

(5-Methyl-2-phenyl-2H-1,2,3-triazole-4-carbonyl) guanidine hydrochloride

Guanidine hydrochloride (2.42 g, 25.32 mmol) was dissolved in 20 ml of anhydrous methanol and then treated with sodium methoxide (1.50 g, 27.83 mmol), added in one portion at room temperature. The reaction mixture was stirred under nitrogen for 1 hour, then filtered under a nitrogen atmosphere. The solids were washed with anhydrous methanol (3×10 ml) and the filtrate concentrated under reduced pressure. Anhydrous benzene (60 ml) was added to the residue, the mixture reconcentrated in vacuo and the residue was dried under high vacuum. Anhydrous dimethylformamide (10 ml), anhydrous tetrahydrofuran (20 ml) and methyl 4-methyl-2-phenyl-2H-1,2,3-triazole-5-carboxylate (1.00 g, 4.60 mmol) were added to the solid residue and the resulting mixture was heated at 70° C. under nitrogen for 7 h, then stirred at ambient temperature overnight. The reddish colored solution was then diluted with water (90 ml) to give the free base corresponding to the title compound as a tan solid (0.53 g, 47% yield).

APCIMS 242.9 [M–H]$^-$ $^1$H NMR (DMSO-d$_6$) δ 2.54 (s, 3H), 7.37 (t, 1H), 7.53 (m, 2H), 7.92 (m, 2H).

The title compound was prepared by suspending the free base (100 mg, 0.41 mmol) in 10 ml of diethyl ether and bubbling excess hydrogen chloride gas into the mixture. The mixture was stirred under nitrogen overnight then filtered to give the title compound as a white solid (85.2 mg, 74% yield).

$^1$H NMR (DMSO-d$_6$) δ 2.55 (s, 3H), 7.48 (t, 1H), 7.6 (m, 2H), 8.12 (m, 2H), 8.56 (s, 2H), 8.73 (s, 2H), 11.62 (s, 1H).

EXAMPLE 6A

[5-Methyl-2-(2-methoxyphenyl)-2H-1,2,3-triazole-4-carbonyl]guanidine hydrochloride Guanidine hydrochloride (5.29 g, 55.3 mmol) was dissolved in 30 ml of anhydrous methanol and then treated with sodium methoxide (3.04 g, 56.2 mmol), added in one portion at room temperature. The reaction mixture was stirred under nitrogen for 1 hour, then filtered under a nitrogen atmosphere. The solids were washed with anhydrous methanol (3×15 ml) and the filtrate concentrated under reduced pressure. Anhydrous benzene (60 ml) was added to the residue, the mixture reconcentrated in vacuo and the resulting guanidine free base was dried under high vacuum. The residue was suspended in a mixture of 10 ml anhydrous THF and 10 ml anhydrous DMF and the resulting mixture was used in the subsequent step.

A solution of 5-methyl-2-(2-methoxyphenyl)-2H-1,2,3-triazole-4-carboxylic acid (2.15 g, 9.2 mmol) and carbonyldiimidazole (1.64 g, 10 mmol) in 30 ml DMF was stirred at room temperature under nitrogen for 2 h. The resulting mixture was added to the mixture of guanidine in THF and DMF previously prepared and the reaction mixture was stirred overnight under nitrogen at room temperature. The reaction mixture was then poured into 200 ml of cold water and the aqueous mixture was extracted with 10×70 ml ethyl acetate. The combined organic extracts were dried (Na$_2$SO$_4$) and concentrated in vacuo to an orangish solid (1.83 g). The crude product was triturated with diethyl ether to yield 0.59 g of the free base corresponding to the title compound. The title compound was prepared by dissolving the free base in 40 ml methanol and bubbling excess hydrogen chloride gas into the solution. After stirring for several hours the resulting precipitate was filtered and washed with diethyl ether to give the title compound as a tan solid (0.5 g, 17% yield).

$^1$H NMR (DMSO-d$_6$) δ 2.54 (s, 3H); 3.8 (s, 3H); 7.14 (t, 1H); 7.32 (d, 1H); 7.52–7.7 (m, 3H); 8.45 (s, 2H); 8.66 (s, 2H); 11.37 (s, 1H).

The title compounds of Examples 6B–6V were prepared according to procedures analogous to those described in Example 6A.

EXAMPLE 6B

[5-Methyl-2-(4-methoxyphenyl)-2H-1,2,3-triazole-4-carbonyl]guanidine hydrochloride 50% yield.

$^1$H NMR (DMSO-d$_6$) δ 2.55 (s, 3H); 3.83 (s, 3H); 7.15 (d, 2H); 8.06 (d, 2H); 8.56 (s, 2H); 8.73 (s, 2H); 11.58 (s, 1H).

EXAMPLE 6C

[5-Methyl-2-(4-sulfamoylphenyl)-2H-1,2,3-triazole-4-carbonyl]guanidine hydrochloride 50% yield.

$^1$H NMR (DMSO-d$_6$) δ 2.58 (s, 3H); 7.55 (s, 2H); 8.04 (d, 2H); 8.35 (d, 2H); 8.62 (s, 2H); 8.79 (s, 2H); 11.84 (s, 1H).

EXAMPLE 6D

[5-Methyl-2-(4-methylsulfonylphenyl)-2H-1,2,3-triazole-4-carbonyl]guanidine hydrochloride 20% yield.

$^1$H NMR (DMSO-d$_6$) δ 2.58 (s, 3H); 3.3 (s, 3H); 8.15 (d, 2H); 8.47 (d, 2H); 8.81 (s, 2H); 8.99 (s, 2H); 12.12 (s, 1H).

EXAMPLE 6E

[5-Methyl-2-(3-methoxyphenyl)-2H-1,2,3-triazole-4-carbonyl]guanidine hydrochloride 35% yield.

$^1$H NMR (DMSO-d$_6$) δ 2.47 (s, 3H); 3.86 (s, 3H); 7.05 (dd, 1H); 7.5 (t, 1H); 7.67 (m, 2H); 8.47(bs, 2H); 8.74 (bs, 2H).

EXAMPLE 6F

[5-Methyl-2-(5-quinolinyl)-2H-1,2,3-triazole-4-carbonyl]guanidine hydrochloride

67% yield.

$^1$H NMR (DMSO-d$_6$) δ 2.62 (s, 3H); 7.79 (m 1H); 8.02 (m, 1H); 8.17 (d, 1H); 8.32 (d, 1H); 8.69 (bs, 4H); 8.92 (d, 1H); 9.12 (s, 1H); 11.7 (s, 1H).

EXAMPLE 6G

[5-Methyl-2-(5-isoquinolinyl)-2H-1,2,3-triazole-4-carbonyl]guanidine hydrochloride 52% yield.

$^1$H NMR (DMSO-$_6$) δ 2.63 (s, 3H); 8.01 (t, 1H); 8.46 (d, 1H); 8.52 (d, 1H); 8.7 (m, 6H); 9.74 (s, 1H); 11.7 (s, 1H).

EXAMPLE 6H

[2-(p-Tolyl)-5-methyl-2H-1,2,3-triazole-4-carbonyl]guanidine

97% yield.

$^1$H NMR (400 MHz, DMSO) δ 2.30 (s, 3H), 2.50 (s, 3H), 7.30 (d, J=8, 2H), 7.79 (d, J=8, 2H).

APCIMS 259 [M+1]$^+$

EXAMPLE 6I

[2-(4-Chlorophenyl)-5-methyl-2H-1,2,3-triazole-4-carbonyl]guanidine

98% yield $^1$H NMR (400 MHz, DMSO) δ 2.51 (s, 3H), 7.56 (d, J=8, 2H), 7.91 (d, J=8, 2H).

APCIMS 279 [M+1]$^+$

EXAMPLE 6J

[2-(3,4-Dichlorophenyl)-5-methyl-2H-1,2,3-triazole-4-carbonyl]guanidine

100% yield $^1$H NMR (400 MHz, DMSO) δ 2.55 (s, 3H), 7.81 (d, J=8, 1H), 7.92 (dd, J=2.8, 8.8, 1H), 8.11 (d, J=2.4, 1H).

APCIMS 311 [M−1]$^-$

EXAMPLE 6K (2.5-Diphenyl-2H-1,2,3-triazole-4-carbonyl)guanidine

88% yield $^1$H NMR (400 MHz, DMSO) δ 7.41 (m, 4H), 7.52 (m, 2H), 7.90 (m, 2H), 8.04 (m, 2H).

APCIMS 307 [M+1]$^+$

EXAMPLE 6L

[2-(3,5-Dichlorophenyl)-5-methyl-2H-1,2,3-triazole-4-carbonyl]guanidine

90% yield $^1$H NMR (400 MHz, DMSO) δ 2.54 (s, 3H), 7.63 (s, 1H), 7.89 (s, 2H).

APCIMS 313 [M+1]$^+$

EXAMPLE 6M

[2-(m-Tolyl)-5-methyl-2H-1,2,3-triazole-4-carbonyl]guanidine

92% yield $^1$H NMR (400 MHz, DMSO) δ 2.35 (s, 3H), 2.51 (s, 3H), 7.16 (m, 1H), 7.37 (m, 1H), 7.83 (m, 2H).

APCIMS 259 [M+1]$^+$

EXAMPLE 6N

[2-(3-Chlorophenyl)-5-methyl-2H-1,2,3-triazole-4-carbonyl]guanidine

92% yield $^1$H NMR (400 MHz, DMSO) δ 2.54 (s, 3H), 7.46 (m, 1H), 7.56 (m, 1H), 7.91 (m, 2H).

APCIMS 279 [M+1]$^+$

EXAMPLE 6O

[2-Phenyl-5-(n-propyl)-2H-1,2,3-triazole-4-carbonyl]guanidine hydrochloride

83% yield $^1$H NMR (400 MHz, CD$_3$OD) δ 1.02 (t, J=7, 3H), 1.81 (m, 2H), 3.15 (m, 2H), 7.48 (m, 1H), 7.50 (m, 2H), 8.15 (m, 2H).

APCIMS 273 [M+1]$^+$

EXAMPLE 6P (2-Phenyl-5-ethyl-2H-1,2,3-triazole-4-carbonyl) guanidine hydrochloride 79% yield $^1$H NMR (400 MHz, CD$_3$OD) δ 1.36 (t, J=8.4, 3H), 7.15 (m, 2H), 7.48 (m, 1H), 7.55 (m, 2H), 8.16 (m, 2H).

APCIMS 259 [M+1]$^+$

EXAMPLE 6Q (2-Phenyl-2H-1,2,3-triazole-4-carbonyl)guanidine

82% yield $^1$H NMR (400 MHz, DMSO) δ 7.30(m, 1H), 7.57(m, 2H), 8.01(m, 2H), 8.19 (s, 1H).

APCIMS 231 [M+1]$^+$

EXAMPLE 6R

[2-(3-Trifluoromethylphenyl)-5-methyl-2H-1,2,3-triazole-4-carbonyl]guanidine hydrochloride 94% yield $^1$H NMR (400 MHz, CD$_3$OD) δ 2.66(s, 3H), 7.81(d, J=4.8, 2H), 8.41(m, 2H).

APCIMS 313 [M+1]$^+$

EXAMPLE 6S

[2-(1-Naphthalenyl)-5-methyl-2H-1,2,3-triazole-4-carbonyl]guanidine hydrochloride 93% yield $^1$H NMR (400 MHz, CD$_3$OD) δ 2.61(s, 3H), 7.61(m, 3H), 7.82(d, J=6, 1H), 7.97(m, 1H), 8.02(m, 1H), 8.10(d, J=8, 1H).

APCIMS 295 [M+1]$^+$

EXAMPLE 6T

[2-(8-Quinolinyl)-5-methyl-2H-1,2,3-triazole-4-carbonyl]guanidine hydrochloride

6% yield $^1$H NMR (400 MHz, CD$_3$OD) δ 2.64 (s, 3H), 7.61 (m, 1H), 7.73 (t, J=7.8, 1H), 7.96 (dd, J=1.4, 7.4, 1H), 8.13(dd, J=1.4, 4.2, 1H), 8.45(dd, J=1.8, 8.6, 1H), 8.86(dd, J=1.6, 4.4, 1H).

APCIMS 296 [M+1]$^+$

EXAMPLE 6U

[2-(3-Bromophenyl)-5-methyl-2H-1,2,3-triazole-4-carbonyl]guanidine hydrochloride 89% yield $^1$H NMR (400 MHz, CD$_3$OD) δ 2.63(s, 3H), 7.50(t, J=8.2, 1H), 7.64 (dd, J=2.0, 1, 1H), 8.12(m, 1H), 8.34(t, J=2, 1H).

APCIMS 323 [M+1]$^+$

EXAMPLE 6V

[5-(N,N-Dimethylcarbamoyl)-2-phenyl-2H-1,2,3-triazole-4-carbonyl]guanidine hydrochloride 80% yield $^1$H NMR (400 MHz, CD$_3$OD) δ 3.08 (s, 3H), 3.19 (s, 3H), 7.59 (m, 3H), 8.18 (m, 2H).

APCIMS 302 [M+1]$^+$

EXAMPLE 7

(2-Phenyl-5-hydroxymethyl-2H-1,2,3-triazole-4-carbonyl)guanidine hydrochloride

A solution of guanidine hydrochloride (1.15 g, 12.0 mmol) in methanol (5 mL) at 23° C. and under a nitrogen atmosphere was treated in one portion with sodium methoxide (0.65 g, 12 mmol). The resulting suspension was stirred for 1 h and filtered. The filtrate was concentrated in vacuo. The residue was dissolved in ethanol (10 mL) and added to 2-phenyl-5-hydroxymethyl-2H-1,2,3-triazole-4-carboxylic acid lactone (0.41 g, 2.0 mmol) (Pollet, P.; Gelin, S. *Synthesis* 1979, 977) at 23° C. The resulting solution was stirred for 15 min and concentrated in vacuo. The residue was triturated with water and filtered. The solid was air-dried to afford 0.43 g (81% yield) of the free base corresponding to the title compound. This material in 5 ml methanol was treated with hydrogen chloride (4 M in dioxane, 2 ml, excess) for 1 hr at 23° C. and concentrated in vacuo to afford the title compound (0.48 g, 79% yield).

$^1$H NMR (400 MHz, DMSO-d$_6$) δ 8.74 (bs, 2H), 8.59 (bs, 2H), 8.16 (d, J=7.6, 2H), 7.62 (t, J=8.0, 2H), 7.52 (t, J=7.4, 1H), 4.83 (s, 2H),

APCIMS 261 [M+1]$^+$

EXAMPLE 8A (5-Methyl-1-phenyl-1H-1,2,3-triazole-4-carbonyl) guanidine hydrochloride 5-Methyl-1-phenyl-1H-1,2,3-triazole-4-carboxylic acid ethyl ester (333 mg, 1.44 mmol) was reacted with guanidine (7.9 mmol), obtained as in Example 5, in 10 mL of methanol at reflux. After 16 hours, the mixture was concentrated in vacuo, the residue taken up in ice water and extracted with ethyl acetate (3×20 mL). The combined organic layers were dried over sodium sulfate, filtered and concentrated in vacuo. The product was purified by silica gel chromatography eluting with 10% methanol in methylene chloride to afford 63 mg of the desired acylguanidine. Transformation to the hydrochloride salt in the manner described in Example 7 afforded the title compound.

$^1$H NMR (DMSO-d$_6$) δ 2.54 (s, 3H), 7.6–7.7 (m, 5H), 8.5 (bs, 2H), 8.7 (bs, 2H), 11.6 (bs, 1H).

APCIMS 245 [M+1]$^+$

The title compound of Example 8B was prepared using a procedure analogous to that used for Example 8A.

EXAMPLE 8B (4-Methyl-5-phenyl-4H-1,2,4-triazole-3-carbonyl) guanidine hydrochloride $^1$H NMR (DMSO-d$_6$) δ 3.9 (s, 3H), 7.6 (m, 3H), 7.8 (m, 2H), 8.5 (bs, 2H), 8.9 (bs, 2H), 11.8 (bs, 1H).

APCIMS 245 [M+1]$^+$

The title compounds of Examples 9A–9N were prepared using procedures analogous to that described in Bajnati, A.; Kokel, B.; Hubert-Habart, M. *Bull. Soc. Chim. Fr.* 1987, 318.

EXAMPLE 9A

Ethyl 3-methyl-1-(4-methoxyphenyl)-1H-pyrazole-4-carboxylate

3% yield.

$^1$H NMR (CDCl$_3$) δ 1.36 (t, 3H); 2.54 (s, 3H); 3.84 (s, 3H); 4.3 (q, 2H); 6.96 (d, 2H); 7.56 (d, 2H); 8.23 (s, 1H).

EXAMPLE 9B

Ethyl 5-methyl-1-(4-methoxyphenyl)-1H-pyrazole-4-carboxylate

6% yield.

$^1$H NMR (CDCl$_3$) δ 1.33 (t, 3H); 2.48 (s, 3H); 3.81 (s, 3H); 4.27 (q, 2H); 6.94 (q, 2H); 7.26 (q, 2H); 7.96 (s, 1H).

EXAMPLE 9C

Ethyl 5-methyl-1-(4-sulfamoylphenyl)-1H-pyrazole-4-carboxylate

77% yield.

$^1$H NMR (DMSO-d$_6$) δ 1.28 (t, 3H); 2.56 (s, 3H); 4.25 (q, 2H); 7.52 (s, 2H)); 7.78 (d, 2H); 7.96 (d, 2H); 8.05 (s, 1H).

EXAMPLE 9D

Ethyl 5-methyl-1-(4-trifluoromethoxyphenyl)-1H-pyrazole-4-carboxylate

32% yield.

$^1$H NMR (CDCl$_3$) δ 1.37 (t, 3H); 2.58 (s, 3H); 4.32 (q, 2H); 7.34 (q, 2H); 7.46 (q, 2H); 8.03 (s, 1H).

EXAMPLE 9E

Ethyl 5-methyl-1-(2-methoxyphenyl)-1H-pyrazole-4-carboxylate

63% yield.

$^1$H NMR (CDCl$_3$) δ 1.34 (t, 3H); 2.34 (s, 3H); 3.77 (s, 3H); 4.3 (q, 2H); 7.02 (m, 2H); 7.28 (q, 1H); 7.41 (m, 1H); 8.01 (s, 1H).

EXAMPLE 9F

Ethyl 5-methyl-1-(4-methylsulfonylphenyl)-1H-pyrazole-4-carboxylate

46% yield.

$^1$H NMR (CDCl$_3$) δ 1.35 (t, 3H); 6.63 (s, 3H); 3.08 (s, 3H); 4.3 (q, 2H); 7.65 (d, 2H); 8.05 (d, 2H); 8.08 (s, 1H).

EXAMPLE 9G

Ethyl 5-methyl-1-(2-pyridyl)-1H-pyrazole-4-carboxylate

50% yield.

$^1$H NMR (DMSO-d$_6$) δ 1.28 (t, 3H); 2.78 (s, 3H); 4.24 (q, 2H); 7.43–7.47 (m, 1H); 7.78 (m, 12H); 8.02 (m, 2H); 8.53 (m 1H).

EXAMPLE 9H

Ethyl 5-methyl-1-(5-quinolinyl)-1H-pyrazole-4-carboxylate

6% yield.

$^1$H NMR (DMSO-d$_6$) δ 1.27 (t, 3H); 2.27 (s, 3H); 4.25 (q, 2H); 7.55 (m, 1H); 7.60 (m, 1H); 7.74 (d, 1H); 7.89 (t, 1H); 8.1 (s, 1H); 8.2 (d, 1H); 8.97 (m, 1H).

EXAMPLE 9I

Ethyl 5-methyl-1-(4-pyridyl)-1H-pyrazole-4-carboxylate

22% yield.

$^1$H NMR (DMSO-d$_6$) δ 1.27 (t, 3H); 2.64 (s, 3H); 4.23 (q, 2H); 7.64 (d, 2H); 8.09 (s, 1H); 8.73 (d, 2H).

EXAMPLE 9J

Ethyl 5-methyl-1-(3-methoxylphenyl)-1H-pyrazole-4-carboxylate

77% yield $^1$H NMR (DMSO-d$_6$) δ 1.26 (t, 3H); 2.49 (s, 3H); 3.78 (s, 3H); 4.22 (q, 2H); 7.03–7.08 (m, 3H); 7.42 (t, 1H); 7.97 (s, 1H).

EXAMPLE 9K

Ethyl 5-methyl-1-(1-phthalazinyl)-1H-pyrazole-4-carboxylate

43% yield.

$^1$H NMR (DMSO-d$_6$) δ 1.28 (t, 3H); 2.51 (s, 3H); 4.25 (q, 2H); 7.89 (d, 1H); 8.09 (q, 1H); 8.1 (q, 1H); 8.19 (s, 1H); 8.32 (d, 1H); 9.84 (s, 1H).

EXAMPLE 9L

Ethyl 5-methyl-1-(4-quinolinyl)-1H-pyrazole-4-carboxylate and Ethyl 3-methyl-1-(4-quinolinyl)-1H-pyrazole-4-carboxylate 68% yield.

$^1$H NMR (DMSO-d$_6$) δ 1.19, 1.25 (2t, 3H); 2.33 (s, 3H); 4.06, 4.25 (2q, 2H); 7.41, 7.70 (2d, 1H); 7.61, 7.82 (2t, 1H); 8.15 (m, 2H); 9.06 (d, 1H).

EXAMPLE 9M

Ethyl 5-methyl-1-(6-quinolinyl)-1H-pyrazole-4-carboxylate

40% yield.

$^1$H NMR (DMSO-d$_6$) δ 1.26 (t, 3H); 2.57 (s, 3H); 4.22 (q, 2H); 7.61 (m, 1H); 7.89 (d, 1H); 8.04 (s, 1H); 8.16 (d, 1H); 8.19 (s, 1H); 8.43 (d, 1H); 8.96 (d, 1H).

EXAMPLE 9N

Ethyl 1-(2-bromophenyl)-5-cyclopropyl-1H-pyrazole-4-carboxylate

78% yield $^1$H NMR (400 MHz, CDCl$_3$) δ 0.80 (bs, 4H), 1.36(t, J=7.2, 3H), 1.87 (m, 1H), 4.30 (q, J=7.2, 2H), 7.41(m, 3H), 7.71(dd, J=1.4, 8, 1H), 8.03(s, 1H).

APCIMS 335 [M+1]$^+$, 337 [M+3]$^+$

The title compounds of Example 10A–10K were prepared using procedures analogous to that described in Menozzi, G.; Mosti, L.; Schenone, P. *J. Heterocycl. Chem.*, 1987, 24, 1669.

EXAMPLE 10A

Ethyl 5-cyclopropyl-1-(2,6-dichlorophenyl)-1H-pyrazole-4-carboxylate

82% yield.
APCIMS 325 [M+1]$^+$
$^1$H NMR (CDCl$_3$) δ 1.77–1.84 (m, 1H), 8.07 (s, 1H).

EXAMPLE 10B

Ethyl 5-methyl-1-(naphthalen-1-yl)-1H-pyrazole-4-carboxylate

93% yield.
APCIMS 281 [M+1]$^+$
$^1$H NMR (CDCl$_3$) δ 2.31 (s, 3H), 8.14 (s, 1H).

EXAMPLE 10C

Ethyl 5-methyl-1-(quinolin-8-yl)-1H-pyrazole-4-carboxylate

66% yield.
APCIMS 282 [M+1]$^+$
$^1$H NMR (CDCl$_3$) δ 2.33 (s, 3H), 8.13 (s, 1H).

EXAMPLE 10D

Ethyl 5-cyclopropyl-1-(quinolin-8-yl)-1H-pyrazole-4-carboxylate

89% yield.
APCIMS 308 [M+1]$^+$
$^1$H NMR (CDCl$_3$) δ 1.81–1.88 (m, 1H), 8.10 (s, 1H).

EXAMPLE 10E

Ethyl 5-cyclopropyl-1-(quinolin-5-yl)-1H-pyrazole-4-carboxylate

88% yield.
APCIMS 308 [M+1]$^+$
$^1$H NMR (CDCl$_3$) δ .8.95 (dd, J=1.8, 4.2, 1H), 8.24 (d, J=8.8, 1H), 8.10 (s, 1H), 7.79 (t, J=7.8, 1H), 7.72 (dt, J=8.4, 0.8, 1H), 7.58 (d, J=7.2, 1H), 7.41 (m, 1H), 4.31 (q, J=7.2, 2H), 1.76 (m, 1H), 1.37 (t, J=7.2, 3H), 0.67 (m, 4H).

EXAMPLE 10F

Ethyl 5-cyclopropyl-1-(quinolin-8-yl)-1H-pyrazole-4-carboxylate

82% yield.
APCIMS 308 [M+1]$^+$
NMR (CDCl$_3$) δ 1.80–1.87 (m, 1H), 8.09 (s, 1H).

EXAMPLE 10G

Methyl 5-ethyl-1-(quinolin-5-yl)-1H-pyrazole-4-carboxylate

30% yield.
APCIMS 280 [M–1]$^−$
$^1$H NMR (CDCl$_3$) δ 0.94–0.97 (t, 3H), 8.10 (s, 1H).

EXAMPLE 10H

Ethyl 5-cyclopropyl-1-(isoquinolin-8-yl)-1H-pyrazole-4-carboxylate

24% yield.
APCIMS 308 [M+1]$^+$
$^1$H NMR (CDCl$_3$) δ 3.25–3.31 (m, 1H), 9.57 (s, 1H).

EXAMPLE 10J

Ethyl 5-cyclopropyl-1-(2-trifluoromethylphenyl)-1H-pyrazole-4-carboxylate

88% yield.
APCIMS 325 [M+1]$^+$
$^1$H NMR (CDCl$_3$) δ 1.70–1.77 (m, 1H), 8.00 (s, 1H);

EXAMPLE 10K

Ethyl 5-cyclopropyl-1-phenyl-1H-pyrazole-4-carboxylate

89% yield.
APCIMS 257 [M+1]$^+$
$^1$H NMR (CDCl$_3$) δ 1.87–2.00 (m, 1H), 8.00 (s, 1H).

EXAMPLE 11

Ethyl 2-methyl-5-phenyl-2H-pyrazole-3-carboxylate (Example 11A) and Ethyl 1-methyl-5-phenyl-1H-pyrazole-3-carboxylate (Example 11B).

The lithium salt of ethyl 2,4-dioxo-4-phenyl-butyrate (Murray, W. V.; Wachter, M. P. *J. Heterocycl. Chem.* 1989, 26, 1389) (1.0 g, 4.4 mmol) was combined in 4 mL absolute ethanol with methyl hydrazine (0.2 g, 4.4 mmol), and hydrochloric acid (1.2 mL of a 4 N solution in dioxane, 4.8 mmol). After heating the mixture at reflux for 2 h, the solution was concentrated in vacuo and the residue purified by silica gel chromatography using 5–20% ethyl acetate in hexanes as eluant to provide earlier eluting Example 11A (0.32 g, 31%) and later eluting Example 11B (0.38 g, 38%).

EXAMPLE 11A

Ethyl 2-methyl-5-phenyl-2H-pyrazole-3-carboxylate $^1$H NMR (CD$_3$OD) δ 1.4 (t, 3H), 4.15 (s, 3H), 4.3 (q, 2H), 7.2 (s, 1H), 7.3 (t, 1H), 7.4 (t, 2H), 7.8 (d, 2H).
APCIMS 231 [M+1]$^+$

EXAMPLE 11B

Ethyl 1-methyl-5-phenyl-1H-pyrazole-3-carboxylate $^1$H NMR (CD$_3$OD) δ 1.4 (t, 3H), 3.9 (s, 3H), 4.3 (q, 2H), 6.8 (s, 1H), 7.4–7.5 (m, 5H).
APCIMS 231 [M+1]$^+$ The title compounds of Example 12A–12B were prepared using procedures analogous to that described in Bajnati, A.; Hubert-Habart, M. *Bull. Soc. Chim. Fr.* 1988, 540.

EXAMPLE 12A n-Butyl 3-methyl-1-(quinolin-5-yl)-1H-pyrazole-4-carboxylate

A mixture of 5-acetyluracil (0.231 g, 1.5 mmol), 5-quinolinylhydrazine dihydrochloride (0.418 g, 1.8 mmol)

and HCl (conc., 0.75 mL, 9 mmol) in n-butanol (15 mL) was heated at reflux for 20 h, cooled to 23° C., and concentrated in vacuo. The residue was dissolved in n-butanol (10 mL). The resulting solution was treated with $H_2SO_4$ (conc., 0.96 mL, 18 mmol), heated at reflux for 20 h, cooled to 23° C. and concentrated in vacuo. The residue was partitioned between EtOAc and NaOH (1 M). The aqueous layer was extracted three times with EtOAc. The combined organic extracts were dried over $Na_2SO_4$ and concentrated in vacuo. The brown solid residue was purified by flash chromatography (Flash 40S, hexanes-acetone 8:2) to afford 0.279 g (60%) of the desired product as a white solid.

$^1$H NMR (400 MHz, $CDCl_3$) δ 0.96(t, J=7, 3H), 1.45 (sextuplet, J=7.2, 2H), 1.72(quintet, J=6.8, 2H). 2.60(s, 3H), 4.28 (quartet, J=6.6, 2H), 7.24(s, 1H), 7.47 (ddd, J=0.8, 4.4, 8.8, 1H), 7.58(d, J=7.2, 1H), 7.76 (t, J=8, 1H), 8.21 (m, 1H), 8.30(d, J=8, 1H), 8.98(dd, J=1.4, 3, 1H).

APCIMS 310 [M+1]$^+$

The title compound of Example 12B was prepared using a procedure analogous to that used for Example 12A.

EXAMPLE 12B n-Butyl 1-(isoquinolin-5-yl)-3-methyl-1H-pyrazole-4-carboxylate

43% yield $^1$H NMR (400 MHz, $CDCl_3$) δ 0.94 (t, J=7.4, 3H), 1.44 (sextuplet, J=7.6, 2H), 1.70(quintuplet, J=6.8, 2H), 2.58(s, 3H), 4.26(t, J=6.6, 2H), 7.66(t, J=7.7, 1H), 7.75(m, 2H), 8.05(d, J=8, 1H), 8.21(s, 1H), 8.57(d, J=6, 1H), 9.33(s, 1H),

APCIMS 310 [M+1]$^+$

EXAMPLE 13A

5-Methyl-1-(2-methoxyphenyl)-1H-pyrazole-4-carboxylic acid

To a solution of ethyl 5-methyl-1-(2-methoxyphenyl)-1H-pyrazole-4-carboxylate in 15 ml methanol and 17 ml water was added 20 ml of 1 N sodium hydroxide and the resulting mixture was refluxed overnight under nitrogen. The methanol was removed in vacuo and the aqueous phase was acidified with dilute aqueous hydrochloric acid solution and extracted with 2×70 ml ethyl acetate. The combined ethyl acetate extracts were washed with 70 ml water and 70 ml brine, dried over sodium sulfate and concentrated in vacuo to a white solid (2.14 g, 85% yield).

$^1$H NMR ($CDCl_3$) δ 2.37 (s, 3H); 3.79 (s, 3H); 7.04 (q, 2H); 7.3 (d, 1H); 7.44 (m, 1H); 8.09 (s, 1H).

The title compounds of Examples 13B–13Z were prepared using procedures analogous to that used for Example 13A.

EXAMPLE 13B

3-Methyl-1-(4-methoxyphenyl)-1H-pyrazole-4-carboxylic acid

57% yield.

$^1$H NMR (DMSO-$d_6$) δ 2.39 (s, 3H); 3.77 (s, 3H); 7.01 (d, 2H); 7.76 (d, 2H): 8,72 (s, 1H).

EXAMPLE 13C

5-Methyl-1-(4-methoxyphenyl)-1H-pyrazole-4-carboxylic acid

91% yield.

$^1$H NMR (DMSO-$d_6$) δ 2.43 (s, 3H); 3.81 (s, 3H); 7.08 (d, 2H); 7.41 (d, 2H); 7.9 (s, 1H); 12.4 (s, 1H).

EXAMPLE 13D

5-Methyl-1-(4-sulfamoylphenyl)-1H-pyrazole-4-carboxylic acid

51% yield.

$^1$H NMR (DMSO-$d_6$) δ 2.46 (s, 3H); 7.48 (s, 2H); 7.72 (d, 2H); 7.92 (d, 2H); 7.98 (s, 1H).

EXAMPLE 13E

5-Methyl-1-(4-trifluoromethoxyphenyl)-1H-pyrazole-4-carboxylic acid

91% yield.

$^1$H NMR (DMSO-$d_6$) δ 2.45 (s, 3H); 7.53 (t, 1H); 7.65 (m, 2H); 7.95 (s, 1H); 12.5 (s, 1H).

EXAMPLE 13F

5-Methyl-1-(4-methylsulfonyl)-1H-pyrazole-4-carboxylic acid

82% yield.

$^1$H NMR (DMSO-$d_6$) δ 2.55 (s, 3H); 3.26 (s, 3H); 7.81 (d, 2H); 7.83 (s, 1H); 8.02 (d, 2H); 12.5 (s, 1H).

EXAMPLE 13G

5-Methyl-1-(2-pyridyl)-1H-pyrazole-4-carboxylic acid

91% yield.

$^1$H NMR (DMSO-$d_6$) δ 2.78 (s, 3H); 7.45 (q, 1H); 7.77 (d, 1H); 7.95–8.05 (m, 2H); 8.53 (d, 1H); 12.55 (s, 1H).

EXAMPLE 13H

5-Methyl-1-(5-quinolinyl)-1H-pyrazole-4-carboxylic acid

75% yield.

$^1$H NMR (DMSO-$d_6$) δ 2.27 (s, 3H); 7.56 (m, 1H); 7.62 (m, 1H); 7.77 (d, 1H); 7.91 (t, 1H); 8.07 (s, 1H); 8.21 (d, 1H); 8.99 (m, 1H).

EXAMPLE 13I

5-Methyl-1-(4-pyridyl)-1H-pyrazole-4-carboxylic acid

3% yield.

$^1$H NMR (DMSO-$d_6$) δ 2.62 (s, 3H); 7.61 (q, 2H); 7.95 (s, 1H); 8.68 (q, 2H).

EXAMPLE 13J

5-Methyl-1-(3-methoxyphenyl)-1H-pyrazole-4-carboxylic acid

98% yield.

$^1$H NMR (DMSO-$d_6$) δ 2.46 (s, 3H); 3.76 (s, 3H); 7.04 (m, 3H); 7.41 (m, 1H); 7.91 (s, 1H); 12.4 (s, 1H).

EXAMPLE 13K

5-Methyl-1-(1-phthalazinyl)-1H-pyrazole-4-carboxylic acid

84% yield.
$^1$H NMR (DMSO-$d_6$) δ 2.57 (s, 3H); 7.88 (d, 1H); 8.07–8.18 (m, 3H); 8.34 (d, 1H); 9.86 (s, 1H).

EXAMPLE 13L

5-Methyl-1-(4-quinolinyl)-1H-pyrazole-4-carboxylic acid

66% yield.
$^1$H NMR (DMSO-$d_6$) δ 2.31 (s, 3H); 7.42 (d, ih); 7.62 (dd, 1H); 7.7 (d, 1H); 7.83 (t, 1H); 8.10 (d and s, 2H); 9.06 (d, 1H); 12.5 (bs, 1H).

EXAMPLE 13M

5-Methyl-1-(6-quinolinyl)-1H-pyrazole-4-carboxylic acid

84% yield.
$^1$H NMR (DMSO-$d_6$) δ 2.63 (s, 3H); 7.66 (m, 1H); 7.98 (d, 1H); 8.07 (s, 1H); 8.22 (m, 2H); 8.48 (d, 1H); 9.02 (d, 1H).

EXAMPLE 13N

4-Methyl-1-phenyl-1H-pyrazole-3-carboxylic acid $^1$H NMR (CDCl$_3$) δ 2.4 (s, 3H), 7.4 (t, 1H), 7.5 (t, 2H), 7.7 (d, 2H), 7.8 (s, 1H).
APCIMS 203 [M+1]$^+$

EXAMPLE 13O

3-Methyl-1-phenyl-1H-pyrazole-4-carboxylic acid $^1$H NMR (CD$_3$OD) δ 2.5 (s, 3H), 7.4 (t, 1H), 7.5 (t, 2H), 7.8 (d, 2H), 8.6 (s, 1H).
APCIMS 203 [M+1]$^+$

EXAMPLE 13P

5-Cyclopropyl-1-phenyl-1H-pyrazole-4-carboxylic acid

94% yield.
APCIMS 227 [M−1]$^-$
$^1$H NMR (DMSO-$d_6$) δ 1.99–2.06(m, 1H), 7.88(s, 1H).

EXAMPLE 13Q

5-Cyclopropyl-1-(2.6-dichlorophenyl)-1H-pyrazole-4-carboxylic acid

99% yield.
APCIMS 295 [M−1]$^-$
$^1$H NMR (DMSO-$d_6$) δ 1.73–1.80 (m, 1H), 7.98 (s, 1H).

EXAMPLE 13R 1-(2-Bromophenyl)-5-cyclopropyl-1H-pyrazole-4-carboxylic acid

93% yield
$^1$H NMR (400 MHz, DMSO-$d_6$) δ 0.66 (bs, 4H), 1.82(m, 1H), 7.50(m, 3H), 7.80(dd, J=1.2, 7.6, 1H), 7.89 (s, 1H), 12.33(s, 1H).
APCIMS 307 [M+1]$^+$, 309 [M+3]$^+$

EXAMPLE 13S

5-Methyl-1-(naphthalen-1-yl)-1H-pyrazole-4-carboxylic acid

79% yield
APCIMS 251 [M−1]$^-$ $^1$H NMR (DMSO-$d_6$) δ 2.22 (s, 3H), 7.09–7.11 (d, 1H).

EXAMPLE 13T

5-Methyl-1-(quinolin-8-yl)-1H-pyrazole-4-carboxylic acid

65% yield.
APCIMS 252 [M−1]$^-$
$^1$H NMR (DMSO-$d_6$) δ 2.13 (s, 3H), 8.84–8.85 (d, 1H).

EXAMPLE 13U

5-Methyl-1-(isoquinolin-5-yl)-1H-pyrazole-4-carboxylic acid

45% yield.
APCIMS 252 [M−1]$^-$
$^1$H NMR (DMSO-$d_6$) δ 2.24 (s, 3H), 8.05 (s, 1H).

EXAMPLE 13V

5-Cyclopropyl-1-(quinolin-8-yl)-1H-pyrazole-4-carboxylic acid

66% yield.
APCIMS 278 [M−1]$^-$
$^1$H NMR (DMSO-$d_6$) δ 1.69–1.76(m, 1H), 7.97(s, 1H).

EXAMPLE 13W

5-Cyclopropyl-1-(quinolin-5-yl)-1H-pyrazole-4-carboxylic acid

56% yield.
APCIMS 278 [M−1]$^-$
$^1$H NMR (DMSO-$d_6$) δ 8.94 (dd, J=1.6, 4.0, 1H), 8.15 (dd, J=0.8, 8.4, 1H), 7.87 (s, 1H), 7.85–7.83 (m, 1H), 7.71 (dd, J=1.2, 7.2, 1H), 7.59–7.51 (m, 2H), 1.79 (m, 1H), 0.69 (m, 2H), 0.51–0.47 (m, 2H).

EXAMPLE 13X

5-Cyclopropyl-1-(2-trifluoromethylphenyl)-1H-pyrazole-4-carboxylic acid

72% yield.
APCIMS 295 [M−1]$^-$
$^1$H NMR (DMSO-$d_6$) δ 1.71–1.78(m, 1H), 7.89(s, 1H).

EXAMPLE 13Y

5-Ethyl-1-(quinolin-5-yl)-1H-pyrazole-4-carboxylic acid

98% yield.
APCIMS 266 [M−1]$^-$
$^1$H NMR (DMSO-$d_6$) δ 0.75–0.79 (t, 3H), 8.94–8.94 (d, 1H).

EXAMPLE 14A

2-Methyl-5-phenyl-2H-pyrazole-3-carboxylic acid.

2-Methyl-5-phenyl-2H-pyrazole-3-carboxylic acid ethyl ester (0.32 g, 1.39 mmol) was dissolved in 4.5 mL of tetrahydrofuran, 1.5 mL of methanol and 1.5 mL of water, and treated with lithium hydroxide hydrate (0.12 g, 2.78 mmol). After stirring at room temperature overnight, the mixture was acidified (pH=1) with hydrochloric acid, and extracted with ethyl acetate (3×10 mL) and the combined organic phases washed with 10 mL of brine. The organic extracts were dried over sodium sulfate, filtered and concentrated in vacuo to afford a quantitative yield of the title compound.

$^1$H NMR (CD$_3$OD) δ 4.2 (s, 3H), 7.2 (s, 1H), 7.3 (t, 1H), 7.4 (t, 2H), 7.8 (d, 2H).

APCIMS 203 [M+1]$^+$

The title compounds of Examples 14B–14D were prepared using a procedure analogous to that used for Example 14A.

EXAMPLE 14B

1-Methyl-5-phenyl-1H-pyrazole-3-carboxylic acid $^1$H NMR (CD$_3$OD) δ 3.9 (s, 3H), 6.8 (s, 1H), 7.4–7.5 (m, 5H).

APCIMS 203 [M+1]$^+$

EXAMPLE 14C

3-Methyl-1-(quinolin-5-yl)-1H-pyrazole-4-carboxylic acid

86% yield $^1$H NMR (400 MHz, DMSO-d$_6$) δ 2.45(s, 3H), 7.60(ddd, J=1.2, 4.0, 8.8, 1H), 7.73(d, J=7.6., 1H). 7.84(t, J=8, 1H), 8.12 (d, J=8.4, 1H), 8.26(d, J=8.8, 1H), 8.59(s, 1H), 8.97(dd, J=1.2, 2.8, 1H), 8.98(dd, J=1.4, 3, 1H).

APCIMS 252 [M–1]$^-$

EXAMPLE 14D 1-(Isoquinolin-5-yl)-3-methyl-1H-pyrazole-4-carboxylic acid

97% yield $^1$H NMR (400 MHz, DMSO-d$_6$) δ 2.46 (s, 3H), 7.60 (m, 2H), 7.92 (d, J=7.2, 1H), 8.25(d, J=8, 1H), 8.56(d, J=6, 1H), 8.64(s, 1H), 9.44(s, 1H), 12.50 (bs, 1H).

APCIMS 252 [M–1]$^-$

The title compounds of Examples 15A–15II were prepared using procedures analogous to that used for Example 6A.

EXAMPLE 15A

[3-Methyl-1-(4-methoxyphenyl)-1H-pyrazole-4-carbonyl]guanidine hydrochloride

34% yield.

$^1$H NMR (DMSO-d$_6$) δ 2.42 (s, 3H); 3.76 (s, 3H); 7.08 (d, 2H); 7.63 (d, 2H); 8.32 (bs, 2H); 8.43 (bs, 2H); 9.45 (s, 1H).

EXAMPLE 15B

[5-Methyl-1-(4-methoxyphenyl)-1H-pyrazole-4-carbonyl]guanidine hydrochloride

24% yield.

$^1$H NMR (DMSO-d$_6$) δ 2.49 (s, 3H); 3.82 (s, 3H); 7.08 (d, 2H); 7.44 (d, 2H); 8.35 (bs, 2H); 8.63 (bs, 2H); 8.64 (s, 1H).

EXAMPLE 15C

[5-Methyl-1-(4-sulfamoylphenyl)-1H-pyrazole-4-carbonyl]guanidine hydrochloride

19% yield.

$^1$H NMR (DMSO-d$_6$) δ 2.46 (s, 3H); 7.51 (s, 2H); 7.77 (d, 2H); 7.95 (d, 2H); 8.31 (bs, 2H); 8.47 (bs, 2H); 8.58 (s, 1H).

EXAMPLE 15D

[5-Methyl-1-(4-trifluoromethoxyphenyl)-1H-pyrazole-4-carbonyl]guanidine hydrochloride 20% yield.

$^1$H NMR (DMSO-d$_6$) δ 2.49 (s, 3H); 7.58 (d, 2H); 7.7 (d, 2H); 8.36 (bs, 2H); 8.61 (bs, 2H); 8.69 (s, 1H); 11.75 (s, 1H).

EXAMPLE 15E

[5-Methyl-1-(2-methoxyphenyl)-1H-pyrazole-4-carbonyl]guanidine hydrochloride

27% yield.

$^1$H NMR (DMSO-d$_6$) δ 2.27 (s, 3H); 3.76 (s, 3H); 7.1 (t, 1H); 7.27 (d, 1H); 7.34 (d, 1H); 7.54t, 1H); 8.34 (bs, 2H); 8.62 (bs, 3H).

EXAMPLE 15F

5-Methyl-1-(4-methylsulfonyl)-1H-pyrazole-4-carbonyl]guanidine hydrochloride

51% yield.

$^1$H NMR (DMSO-d$_6$) δ 2.61 (s, 3H); 3.29 (s, 3H); 7.85 (d, 2H); 8.09 (d+s, 3H); 8.4–8.7 (bd, 4H); 11.9 (s, 1H).

EXAMPLE 15G

[5-Methyl-1-(2-pyridyl)-1H-pyrazole-4-carbonyl]guanidine hydrochloride

60% yield.

$^1$H NMR (DMSO-d$_6$) δ 2.8 (s, 3H); 7.51 (s, 1H); 7.83 (d, 1H); 8.07 (t, 1H); 7.5–8.2 (bs, 2H); 8.44 (s, 1H); 8.56 (s, 1H); 8.71 (s, 1H); 8.8 (s, 1H); 11.9 (s, 1H).

EXAMPLE 15H

[5-Methyl-1-(5-quinolinyl)-1H-pyrazole-4-carbonyl]guanidine hydrochloride

53% yield.

$^1$H NMR (DMSO-d$_6$) δ 2.31 (s, 3H); 7.59 (m, 1H); 7.68 (d, 1H); 7.79 (d, 1H); 7.93 (t, 1H); 8.27 (d, 1H); 8.55 (bs, 2H); 8.81 (bs, 2H); 8.98 (s, 1H); 9.00 (d, 1H).

EXAMPLE 15I

[5-Methyl-1-(4-pyridyl)-1H-pyrazole-4-carbonyl]guanidine hydrochloride

9% yield.

$^1$H NMR (DMSO-d$_6$) δ 2.68 (s, 3H); 7.87 (d, 2H); 8.41 (bs, 2H); 8.67 (bs, 2H); 8.86 (s and d, 3H).

EXAMPLE 15J

[5-Methyl-1-(3-methoxyphenyl)-1H-pyrazole-4-carbonyl]guanidine hydrochloride

57% yield.

$^1$H NMR (DMSO-d$_6$) δ 2.5 (s, 3H); 3.77 (s, 3H); 7.07 (m, 3H); 7.43 (m, 1H); 8.36 (bs, 2H); 8.66 (bs, 2H); 8.69 (s, 1H).

EXAMPLE 15K

[5-Methyl-1-(1-phthalazinyl)-1H-pyrazole-4-carbonyl]guanidine hydrochloride

18% yield.
$^1$H NMR (DMSO-d$_6$) δ 2.57 (s, 3H); 7.87 (d, 1H); 8.09 (q, 1H); 8.16 (q, 1H); 8.36 (d, 1H); 8.49 (bs, 1H); 8.76 (bs, 2H); 9.90 (s, 1H).

EXAMPLE 15L

[5-Methyl-1-(4-quinolinyl)-1H-pyrazole-4-carbonyl]guanidine hydrochloride

45% yield.
$^1$H NMR (DMSO-d$_6$) δ 2.39 (s, 3H); 7.5 (d, 1H); 7.70 (t, 1H); 7.86 (d, 1H); 7.92 (t, 1H); 8.23 (d, 1H); 8.5 (bs, 2H); 8.77 (bs, 2H); 9.01 (s, 1H); 9.18 (s, 1H); 12.2 (s, 1H).

EXAMPLE 15M

[5-Methyl-1-(6-quinolinyl)-1H-pyrazole-4-carbonyl]guanidine hydrochloride

92% yield. $^1$H NMR (DMSO-d$_6$) δ 2.69 (s, 3H); 7.87 (m, 1H); 8.11 (d, 1H); 8.33 (d, 1H); 8.42 (s, 1H); 8.46 (bs, 2H); 8.73 (bs, 2H); 8.79 (d, 1H); 8.88 (s, 1H); 9.16 (d, 1H); 12.1 (s, 1H).

EXAMPLE 15N (5-Methyl-1-phenyl-1H-pyrazole-4-carbonyl)guanidine hydrochloride 62% yield.
$^1$H NMR (DMSO-d$_6$) δ 2.49 (s, 3H); 7.52 (m, 5H); 8.34 (s, 2H); 8.63 (s, 1H); 8.67 (s, 2H); 11.79 (s, 1H).

EXAMPLE 15O

[1-(2-Bromophenyl)-5-cyclopropyl-1H-pyrazole-4-carbonyl]guanidine hydrochloride

66% yield
$^1$H NMR (400 MHz, DMSO-d$_6$) δ 0.59 (bs, 2H), 0.74 (d, J=7.6, 2H), 1.92 (m, 1H), 7.55(m, 3H), 7.85(d, J=7.6, 1H), 8.41 (bs, 2H), 8.66(s, 1H), 8.70 (bs, 1H), 11.83(s, 1H).
APCIMS 348 [M+1]$^+$, 350 [M+3]$^+$

EXAMPLE 15P (4-Methyl-1-phenyl-1H-pyrazole-3-carbonyl)guanidine hydrochloride $^1$H NMR (CD$_3$OD) δ 2.3 (s, 3H), 7.3 (t, 1H), 7.4 (t, 2H), 7.8 (d, 2H), 8.0 (s, 1H).
APCIMS 244 [M+1]$^+$

EXAMPLE 15Q (5-Methyl-1-phenyl-1H-pyrazole-3-carbonyl)guanidine hydrochloride $^1$H NMR (CD$_3$OD) δ 2.4 (s, 3H), 7.4 (t, 1H), 7.5 (t, 2H), 7.8 (d, 2H), 8.2 (s, 1H).
APCIMS 244 [M+1]$^+$

EXAMPLE 15R

[1-(4-Bromophenyl)-4-methyl-1H-pyrazole-3-carbonyl]guanidine hydrochloride $^1$H NMR (CD$_3$OD) δ 2.4 (s, 3H), 7.7 (d, 2H), 7.8 (d, 2H), 8.2 (s, 1H).
APCIMS 322 [M+1]$^+$, 324 [M+3]$^+$.

EXAMPLE 15S

[1-(4-Bromophenyl)-5-methyl-1H-pyrazole-3-carbonyl]guanidine hydrochloride $^1$H NMR (CD$_3$OD) δ 2.3 (s, 3H), 6.7 (s, 1H), 7.4 (d, 2H), 7.7 (d, 2H).
APCIMS 322 [M+1]$^+$, 324 [M+3]$^+$

EXAMPLE 15T (1-Phenyl-1H-pyrazole-3-carbonyl)guanidine hydrochloride $^1$H NMR (CD$_3$OD) δ 6.9 (d, 1H, J=3 Hz), 7.3 (t, 1H), 7.5 (t, 2H), 7.8 (d, 2H), 8.2 (d, 1H, J=3Hz).
APCIMS 230 [M+1]$^+$

EXAMPLE 15U (3-Methyl-1-phenyl-1H-pyrazole-4-carbonyl)guanidine hydrochloride $^1$H NMR (DMSO-d$_6$) δ 2.4 (s, 3H), 7.4 (t, 1H), 7.6 (t, 2H), 7.8 (d, 2H), 8.4 (bs, 2H), 8.5 (bs, 2H), 9.6 (s, 1H), 12.0 (s, 1H).
APCIMS 244 [M+1]$^+$

EXAMPLE 15V (2-Methyl-5-phenyl-2H-pyrazole-3-carbonyl)guanidine hydrochloride $^1$H NMR (DMSO-d$_6$) δ 4.1 (s, 3H), 7.3 (s, 1H), 7.4 (t, 1H), 7.4 (t, 2H), 7.7 (d, 2H), 8.5 (bs 2H), 8.6 (bs, 2H), 11.4 (bs, 1H).
APCIMS 244 [M+1]$^+$

EXAMPLE 15W (1-Methyl-5-phenyl-1H-pyrazole-3-carbonyl)guanidine hydrochloride $^1$H NMR (DMSO-d$_6$) δ 4.0 (s, 3H), 7.1 (s, 1H), 7.5–7.6 (m, 5H), 8.5 (bs, 2H), 8.6 (bs, 2H), 12.1 (bs, 1H).
APCIMS 244 [M+1]$^+$

EXAMPLE 15X

[2-Methyl-5-(naphthalen-1-yl)-2H-pyrazole-3-carbonyl]guanidine hydrochloride $^1$H NMR (DMSO-d$_6$) δ 4.2 (s, 3H), 7.6 (m, 3H), 7.67 (d, 1H), 7.9 (s, 1H), 8.0 (m, 2H), 8.5 (m, 3H), 8.6 (bs, 2H).
APCIMS 292 [M−1]$^−$

EXAMPLE 15Y

[5-(tert-Butyl)-2-methyl-2H-pyrazole-3-carbonyl]guanidine hydrochloride $^1$H NMR (DMSO-d$_6$) δ 1.2 (s, 9H), 4.0 (s, 3H), 7.4 (s, 1H), 8.4 (bs, 2H), 8.6 (bs, 2H), 11.8 (bs, 1H).
APCIMS 224 [M+1]$^+$

EXAMPLE 15Z (1,5-Diphenyl-1H-pyrazole-3-carbonyl)guanidine hydrochloride $^1$H NMR (DMSO-d$_6$) δ 7.2 (m, 2H), 7.3 (m, 4H), 7.4 (m, 2H), 7.5 (m, 3H), 8.5 (bs, 4H).
APCIMS 306 [M+1]$^+$

EXAMPLE 15AA (14-Dimethyl-5-phenyl-1H-pyrazole-3-carbonyl) guanidine hydrochloride $^1$H NMR (DMSO-$d_6$) δ 2.1 (s, 3H), 3.8 (s, 3H), 7.4–7.6 (m, 5H), 8.5 (bs, 2H), 8.6 (bs, 2H), 11.1 (bs, 1H).

APCIMS 258 [M+1]$^+$

EXAMPLE 15BB

[3-Methyl-1-(naphthalen-1-yl)-1H-pyrazole-4-carbonyl]guanidine hydrochloride $^1$H NMR (DMSO-$d_6$) δ 2.5 (s, 3H), 7.6 (m, 4H), 7.75 (d, 1H, J=8 Hz), 8.1 (m, 2H), 8.3 (bs, 2H), 8.4 (bs, 2H), 9.15 (s, 1H), 11.8 (s, 1H).

APCIMS 294 [M+1]$^+$

EXAMPLE 15CC (2-Methyl-5-phenyl-2H-pyrazole-3-carbonyl) guanidine hydrochloride $^1$H NMR (DMSO-$d_6$) δ 4.1 (s, 3H), 7.3 (s, 1H), 7.4 (t, 1H), 7.4 (t, 2H), 7.7 (d, 2H), 8.5 (bs, 2H), 8.6 (bs, 2H), 11.4 (bs, 1H).

APCIMS 244 [M+1]$^+$

EXAMPLE 15DD (1-Methyl-5-phenyl-1H-pyrazole-3-carbonyl) guanidine hydrochloride $^1$H NMR (DMSO-$d_6$) δ 4.0 (s, 3H), 7.1 (s, 1H), 7.5–7.6 (m, 5H), 8.5 (bs, 2H), 8.6 (bs, 2H), 12.1 (bs, 1H).

APCIMS 244 [M+1]$^+$

EXAMPLE 15EE

[5-(tert-Butyl)-2-methyl-2H-pyrazole-3-carbonyl] guanidine hydrochloride $^1$H NMR (DMSO-$d_6$) δ 1.2 (s, 9H), 4.0 (s, 3H), 7.4 (s, 1H), 8.4 (bs, 2H), 8.6 (bs, 2H), 11.8 (bs, 1H).

APCIMS 224 [M+1]$^+$

EXAMPLE 15FF (1,5-Diphenyl-1H-pyrazole-3-carbonyl)guanidine hydrochloride $^1$H NMR (DMSO-$d_6$) δ 7.2 (m, 2H), 7.3 (m, 4H), 7.4 (m, 2H), 7.5 (m, 3H), 8.5 (bs, 4H).

APCIMS 306 [M+1]$^+$

EXAMPLE 15GG (1,4-Dimethyl-5-phenyl-1H-pyrazole-3-carbonyl) guanidine hydrochloride $^1$H NMR (DMSO-$d_6$) δ 2.1 (s, 3H), 3.8 (s, 3H), 7.4–7.6 (m, 5H), 8.5 (bs, 2H), 8.6 (bs, 2H), 11.1 (bs, 1H).

APCIMS 258 [M+1]$^+$

EXAMPLE 15HH

[3-Methyl-1-(quinolin-5-yl)-1H-pyrazole-4-carbonyl]guanidine hydrochloride

23% yield $^1$H NMR (400 MHz, CD$_3$OD) δ 2.62 (s, 3H), 8.07 (m, 2H), 8.22 (t, J=7.8, 1H), 8.36 (d, J=7.6, 1H), 9.12 (s, 1H), 9.20 (d, J=8.8, 1H), 9.27 (d, J=5.2, 1H).

APCIMS 296 [M+1]$^+$

EXAMPLE 15II

[1-(Isoquinolin-5-yl)-3-methyl-1H-pyrazole-4-carbonyl]guanidine hydrochloride

93% yield $^1$H NMR (400 MHz, DMSO-$d_6$) δ 2.49 (s, 3H),. 7.03 (s, 1H), 8.02 (m, 1H), 8.18 (m, 2H), 8.58 (m, 6H), 9.50 (s, 1H), 9.82 (s 1H), 12.38 (s, 1H).

APCIMS 295 [M+1]$^+$

EXAMPLE 16A

[5-Cyclopropyl-1-(quinolin-5-yl)-1H-pyrazole-4-carbonyl]guanidine dihydrochloride A mixture of 5-cyclopropyl-1-(quinolin-5-yl)-1H-pyrazole-4-carboxylic acid (4.08 g, 14.6 mmol) and 25 ml SOCl$_2$ was heated to reflux for 1 hour. The excess SOCl$_2$ was removed in vacuo via codistillation with toluene. The solid residue was added portionwise over 45 minutes to a vigorously stirred 40° C. solution of guanidine hydrochloride (5.02 g, 52.6 mmol) in 59 ml of 2 N NaOH and 29 ml THF. The resulting mixture was heated at reflux for 1 hour and then cooled to 23° C. The organic solvent and 40 ml of the H$_2$O were removed in vacuo. The tan solid that precipitated was filtered and washed with 2×5 ml portions of cold H$_2$O. This solid was air-dried for 1 hour and then dried for 24 h under high vacuum at 40° C. to afford 3.5 g of the free base of the title compound. This solid was dissolved in 25 ml of hot methanol and treated with 1.85 ml of conc. HCl. This pale yellow solution was stirred for 15 min at room temperature and concentrated in vacuo to a light amber gum. The residual H$_2$O was removed in vacuo via codistillation with 3×25 ml portions of anhydrous ethanol. The resulting pale yellow solid was recrystallized from hot ethanol to afford 3.58 g of the title compound (62% yield).

APCIMS 319 [M−1]$^−$ $^1$H NMR (DMSO-$d_6$) δ 9.16 (m, 1H), 8.86 (s, 1H), 8.85 (bs, 2H), 8.50 (bs, 2H), 8.37 (d, J=8.4, 1H), 8.08–7.97 (m, 3H), 7.78 (dd, J=4.4, 8.4, 1H), 1.99–1.93 (m, 1H), 0.64–0.62 (m, 2H), 0.42 (m, 2H).

The title compounds of Examples 16B–16AA were prepared using procedures analogous to that used for Example 16A.

EXAMPLE 16B

[1-(3,4-Dichlorophenyl)-5-methyl-1H-pyrazole-4-carbonyl]guanidine hydrochloride

23% yield.

APCIMS 301 [M−1]$^−$ $^1$H NMR (DMSO-$d_6$) δ 2.59 (s, 3H), 7.93 (s, 1H)

EXAMPLE 16C (1-Benzyl-5-methyl-1H-pyrazole-4-carbonyl) guanidine hydrochloride 24% yield.

APCIMS 256 [M−1]$^−$ $^1$H NMR (DMSO-$d_6$) δ 2.48 (s, 3H), 8.84 (s, 1H)

EXAMPLE 16D

[5-Methyl-1-(p-tolyl)-1H-pyrazole-4-carbonyl]guanidine hydrochloride

29% yield.
APCIMS 256 [M−1]⁻
$^1$H NMR (DMSO-$d_6$) δ 2.49 (s, 3H), 8.64 (s, 1H)

EXAMPLE 16E (5-Isopropyl-1-phenyl-1H-pyrazole-4-carbonyl)guanidine hydrochloride 42% yield.
APCIMS 270 [M−1]⁻
$^1$H NMR (DMSO-$d_6$) δ 1.22 (d, 6H), 8.63 (s, 1H)

EXAMPLE 16F (1,5-Diphenyl-1H-pyrazole-4-carbonyl)guanidine hydrochloride

17% yield.
APCIMS 304 [M−1]⁻
$^1$H NMR (DMSO-$d_6$) δ 7.17–7.35 (m, 10H), 8.81 (s, 1H)

EXAMPLE 16G (5-Ethyl-1-phenyl-1H-pyrazole-4-carbonyl)guanidine hydrochloride 7% yield.
APCIMS 256 [M−1]⁻
$^1$H NMR (DMSO-$d_6$) δ 1.01–1.06 (t, 3H), 8.64 (s, 1H)

EXAMPLE 16H

[1-Phenyl-5-(n-propyl)-1H-pyrazole-4-carbonyl]guanidine hydrochloride

4% yield.
APCIMS 270 [M−1]⁻
$^1$H NMR (DMSO-$d_6$) δ 0.68–0.71 (t, 3H), 7.08 (s, 1H)

EXAMPLE 16I

[1-(3,5-Dichlorophenyl)-5-methyl-1H-pyrazole-4-carbonyl]guanidine hydrochloride

6% yield.
APCIMS 311 [M−1]⁻
$^1$H NMR (DMSO-$d_6$) δ 2.57 (s, 3H), 8.7 (s, 1H)

EXAMPLE 16J

[1-(2-Chlorophenyl)-5-methyl-1H-pyrazole-4-carbonyl]guanidine hydrochloride

22% yield.
APCIMS 276 [M−1]⁻
$^1$H NMR (DMSO-$d_6$) δ 2.30 (s, 3H), 8.68 (s, 1H)

EXAMPLE 16K

[5-Methyl-1-(3-trifluoromethylphenyl)-1H-pyrazole-4-carbonyl]guanidine hydrochloride 53%% yield.
APCIMS 310 [M−1]⁻
$^1$H NMR (DMSO-$d_6$) δ 2.45 (s, 1H), 8.76 (s, 1H)

EXAMPLE 16L

[1-(3-Chlorophenyl)-5-methyl-1H-pyrazole-4-carbonyl]guanidine hydrochloride

6% yield.
APCIMS 276 [M−1]⁻
$^1$H NMR (DMSO-$d_6$) δ 2.54 (s, H), 8.67 (s, 1H)

EXAMPLE 16M

[5-Methyl-1-(naphthalen-1-yl)-1H-pyrazole-4-carbonyl]guanidine hydrochloride

58% yield.
APCIMS 292 [M−1]⁻
$^1$H NMR (DMSO-$d_6$) δ 2.26 (s, 3H), 8.65 (s, 1H)

EXAMPLE 16N

[1-(4-Chlorophenyl)-5-methyl-1H-pyrazole-4-carbonyl]guanidine hydrochloride

60% yield.
APCIMS 276 [M−1]⁻
$^1$H NMR (DMSO-$d_6$) δ 2.52 (s, 3H), 8.71 (s, 1H)

EXAMPLE 16O

[5-Methyl-1-(2-trifluoromethylphenyl)-1H-pyrazole-4-carbonyl]guanidine hydrochloride 82% yield.
APCIMS 310 [M−1]⁻
$^1$H NMR (DMSO-$d_6$) δ 2.28 (s, 3H), 8.65 (s, 1H)

EXAMPLE 16P (3,5-Dimethyl-1-phenyl-1H-pyrazole-4-carbonyl)guanidine hydrochloride 1% yield.
APCIMS 256 [M−1]⁻
$^1$H NMR (DMSO-$d_6$) δ 2.38 (s, 3H), 2.42 (s, 3H)

EXAMPLE 16Q (1-Cyclohexyl-5-methyl-1H-pyrazole-4-carbonyl)guanidine hydrochloride 59% yield.
APCIMS 248 [M−1]⁻
$^1$H NMR (DMSO-$d_6$) δ 2.50 (s, 3H), 8.41 (s, 1H)

EXAMPLE 16R

[5-Methyl-1-(quinolin-8-yl)-1H-pyrazole-4-carbonyl]guanidine hydrochloride

60% yield.
APCIMS 293 [M−1]⁻
$^1$H NMR (DMSO-$d_6$) δ 2.22 (s, 3H), 8.75 (s, 1H)

EXAMPLE 16S

[1-(2,6-Dichlorophenyl)-5-methyl-1H-pyrazole-4-carbonyl]guanidine hydrochloride

33% yield.
APCIMS 311 [M−1]⁻
$^1$H NMR (DMSO-$d_6$) δ 2.27 (s, 3H), 8.76 (s, 1H)

EXAMPLE 16T

[5-Cyclopropyl-1-(2-trifluoromethylphenyl)-1H-pyrazole-4-carbonyl]guanidine hydrochloride 70% yield.
APCIMS 336 [M−1]−
$^1$H NMR (DMSO-d$_6$) δ 1.83–1.90 (m, 1H), 8.57 (s, 1H)

EXAMPLE 16U

[1-(Isoquinolin-5-yl)-5-methyl-1H-pyrazole-4-carbonyl]guanidine hydrochloride

51% yield.
APCIMS 293 [M−1]−
$^1$H NMR (DMSO-d$_6$) δ 2.33 (s, 3H), 8.98 (s, 1H)

EXAMPLE 16V

[1-(2,3-Dichlorophenyl)-5-methyl-1H-pyrazole-4-carbonyl]guanidine hydrochloride

39% yield.
APCIMS 311 [M−1]−
$^1$H NMR (DMSO-d$_6$) δ 2.32 (s, 3H), 8.78 (s, 1H)

EXAMPLE 16W

[5-Cyclopropyl-1-phenyl-1H-pyrazole-4-carbonyl]guanidine hydrochloride

22% yield.
APCIMS 268 [M−1]−
$^1$H NMR (DMSO-d$_6$) δ 2.11–2.17 (m, 1H), 8.56 (s, 1H)

EXAMPLE 16X

[1-(3-Chlorophenyl)-5-methyl-1H-pyrazole-4-carbonyl]guanidine hydrochloride

A mixture of 5-methyl-1-(3-chlorophenyl)pyrazole-4-carboxylic acid (234 mg, 1.0 mmol) and 5 ml SOCl$_2$ was heated to reflux for 45 min. Excess SOCl$_2$ was removed in vacuo via codistillation with toluene. The residue was dissolved in 2mL of anhydrous THF and added dropwise over 30 minutes to a vigorously stirred 40° C. solution of guanidine hydrochloride (344 mg, 3.6 mol) in 3.25 mL 2 N NaOH and 1.9 mL THF. The resulting mixture was heated to reflux for 4 hours and then cooled. The organic solvent was removed in vacuo. The residue was diluted with 10 mL 1 N NaOH and extracted with 5×5 mL EtOAc. The combined organic layers were dried (Na$_2$SO$_4$) filtered and concentrated in vacuo to a white solid. This material was dissolved in 1 mL MeOH and 18.4 μL 12 N HCl was added with stirring. The solvents were removed in vacuo with toluene azeotropes and the resulting solid was stirred in 1 mL ether/acetone (1:1) and filtered to remove residual H$_2$O. Drying under high vacuum at 40° C. afforded the desired product (20 mg, 6%).

APCIMS 276 [M−1]−;
$^1$H NMR (DMSO-d$_6$) δ 2.54 (s, 3H) 8.68 (s, 1H).

EXAMPLE 16Y

[5-Cyclopropyl-1-(2.6-dichlorophenyl)-1H-pyrazole-4-carbonyl]guanidine hydrochloride 61% yield.
APCIMS 337 [M−1]−
$^1$H NMR (DMSO-d$_6$) δ 1.82–1.89 (m, 1H), 8.65 (s, 1H)

EXAMPLE 16Z

[5-Cyclopropyl-1-(quinolin-8-yl)-1H-pyrazole-4-carbonyl]guanidine hydrochloride

APCIMS 319 [M−1]−
$^1$H NMR DMSO-d$_6$) δ 1.77–1.84 (m, 1H), 8.87(s, 1H).
Yield of HCl salt 3.5%

EXAMPLE 16AA

[5-Ethyl-1-(quinolin-5-yl)-1H-pyrazole-4-carbonyl]guanidine hydrochloride

14% yield.
APCIMS 307 [M−1]−
$^1$H NMR (DMSO-d$_6$) δ 0.86–0.89 (t, 3H), 8.93 (s, 1H).

The title compound of Example 17 was prepared using a procedure analogous to that described in Klinsberg, E. *Synthesis* 1972, 475, and Example 3A.

EXAMPLE 17

2-(Naphthalen-2-yl)-5-methyl-2H-1,2,3-triazole-4-carboxylic acid

52% yield
$^1$H NMR (400 MHz, DMSO-d$_6$) δ 2.52(s, 3H), 7.55(m, 2H), 7.96(d, J=8, 1H), 8.12(m, 3H), 8.53(s, 1H).
APCIMS 252 [M−1]−

The title compound of Example 18 was prepared using a procedure analogous to that used for Example 16A.

EXAMPLE 18

[2-(Naphthalen-2-yl)-5-methyl-2H-1,2,3-triazole-4-carbonyl]guanidine hydrochloride 94% yield
$^1$H NMR (400 MHz, DMSO-d$_6$) δ 2.54(s, 3H), 7.11(m, 1H), 7.56(m, 3H), 8.10(m, 4H), 8.29(m, 2H), 8.63(m, 2H).
APCIMS 295 [M+1]+

The title compounds of Examples 19A–19OOO were prepared using procedures analogous to that described in Menozi, G.; Mosti, L.; Schenone, P. *J. Heterocycl. Chem.*, 1987, 24, 1669.

EXAMPLE 19A

Ethyl 5-cyclopropyl-1-(2,3-dimethoxyphenyl)-1H-pyrazole-4-carboxylate

89% yield.
APCIMS 317 [M+1]+
$^1$H NMR (400 MHz, CDCl$_3$) δ 0.66–0.88 (m, 4H), 1.36 (t, J=7.2, 3H), 1.93 (m, 1H), 3.60 (s, 3H), 3.92 (s, 3H), 4.30 (q, J=7.2, 2H0, 6.93 (d, J=8, 1H), 7.02 (d, J=8.4, 1H), 7.13 (t, J=8, 1H), 8.01 (s, 1H).

EXAMPLE 19B

Ethyl 5-cyclopropyl-1-(naphthalen-1-yl)-1H-pyrazole-4-carboxylate

72% yield.
APCIMS 307 [M+1]+
$^1$H NMR (400 MHz, CDCl$_3$) δ 0.6–0.8 (m, 4H), 1.39 (t, J=7.2, 3H), 1.80 (m, 1H), 4.33 (q, J=7.2, 2H), 7.30 (d, J=7.6, 1H), 7.52 (m, 4H), 7.92 (d, J=8, 1H), 7.98 (d, J=7.6, 1H), 8.12 (s, 1H).

EXAMPLE 19C

Ethyl 5-cyclopropyl-1-(naphthalen-2-yl)-1H-pyrazole-4-carboxylate

96% yield.
APCIMS 307 [M+1]+
$^1$H NMR (400 MHz, CDCl$_3$) δ 0.64 (m, 2H), 0.91 (m, 2H), 1.39 (m, 3H), 2.07 (m 1H), 4.33 (m, 2H), 7.25 (m, 1H), 7.56 (m, 2H), 7.66 (m, 1H), 8.06 (m, 4H).

EXAMPLE 19D

Ethyl 5-cyclopropyl-1-(o-biphenyl)-1H-pyrazole-4-carboxylate

57% yield.
APCIMS 333 [M+1]+
$^1$H NMR (400 MHz, CDCl$_3$) δ 0.46 (m, 4H), 0.99 (m, 1H), 1.28 (m, 3H), 4.19 (m, 2H), 7.03 (m, 2H), 7.22 (m, 3H), 7.41–7.53 (m, 4H), 7.97 (s, 1H).

EXAMPLE 19E

Ethyl 5-cyclopropyl-1-(2-nitrophenyl)-1H-pyrazole-4-carboxylate

51% yield.
APCIMS 302 [M+1]+
$^1$H NMR (400 MHz, CDCl$_3$) δ 0.68 (m, 2H), 0.86 (m, 2H), 1.36 (m, 3H), 1.82 (m, 1H), 4.32 (m, 2H), 7.55–7.76 (m, 3H), 8.03 (m, 3H).

EXAMPLE 19F

Ethyl 5-cyclopropyl-1-(2-ethylphenyl-)-1H-pyrazole-4-carboxylate

53% yield.
APCIMS 285 [M+1]+
$^1$H NMR (400 MHz, CDCl$_3$) δ 0.75 (m, 2H), 0.85 (m, 2H), 1.07 (m, 3H), 1.35 (m, 3H), 1.78 (m, 1H), 2.36 (q, J=7.4, 2H), 4.27 (m, 2H), 7.23 (m, 2H), 7.29–7.42 (m, 2H), 7.98 (s, 1H).

EXAMPLE 19G

Ethyl 5-cyclopropyl-1-(2-methylphenyl-)-1H-pyrazole-4-carboxylate

73% yield.
APCIMS 291 [M+1]+
$^1$H NMR (400 MHz, CDCl$_3$) δ 0.75–0.81 (m, 4H), 1.34 (dt, J=7, 0.8, 3H), 1.83 (m, 1H), 2.05 (s, 3H), 4.28 (dq, J=7.2, 0.4, 2H), 7.30–7.38 (m, 4H), 7.99 (s, 1H).

EXAMPLE 19H

Ethyl 5-cyclopropyl-1-(2-chlorophenyl-)-1H-pyrazole-4-carboxylate

75% yield.
APCIMS 291 [M+1]+
$^1$H NMR (400 MHz, CDCl$_3$) δ 0.6–0.9 (bs, 4H), 1.34 (dt, J=7.2, 3.6, 3H), 1.85 (m, 1H), 4.28 (q, J=7.2, 2H), 7.37–7.44 (m, 3H), 7.52 (m, 1H), 8.03 (s, 1H).

EXAMPLE 19I

Ethyl 5-cyclopropyl-1-(2-trifluoromethylphenyl-)-1H-pyrazole-4-carboxylate

69% yield.
APCIMS 341 [M+1]+
$^1$H NMR (400 MHz, CDCl$_3$) δ 0.62 (d, J=8.8, 2H), 0.78–0.85 (m, 2H), 1.35 (t, J=7.2, 3H), 1.85 (m, 1H), 4.20 (dq, J=14.4, 7.2, 2H), 7.35–7.6 (m, 4H), 8.03 (s, 1H).

EXAMPLE 19J

Ethyl 5-cyclopropyl-1-(2-fluorophenyl-)-1H-pyrazole-4-carboxylate

81% yield.
APCIMS 275 [M+1]+
$^1$H NMR (400 MHz, CDCl$_3$) δ 0.63 (m, 2H), 0.83 (m, 2H), 1.36 (t, J=7.2, 3H), 1.92 (m, 1H), 4.20 (q, J=7.2, 2H), 7.21–7.29 (m, 2H), 7.43–7.48 (m, 2H), 8.04 (s, 1H).

EXAMPLE 19K

Ethyl 5-cyclopropyl-1-(indazol-7-yl)-1H-pyrazole-4-carboxylate

59% yield.
APCIMS 297 [M+1]+
$^1$H NMR (400 MHz, CDCl$_3$) δ 0.56–0.60 (m, 2H), 1.00–1.23 (m, 2H), 1.37 (m, 3H), 2.07 (m, 1H), 4.33 (dq, J=6.8, 1.6, 2H), 7.22 (m, 1H), 7.60 (d, J=6.8, 1H), 7.75 (d, J=7.6, 1H), 8.12 (s, 1H), 10.97 (bs, 1H).

EXAMPLE 19L

Methyl 5-ethyl-1-(benzothiazol-2-yl)-1H-pyrazole-4-carboxylate

69% yield.
APCIMS 288 [M+1]+
$^1$H NMR (400 MHz, CDCl$_3$) δ 1.34 (t, J=6.8, 3H), 3.69 (q, J=6.8, 2H), 3.85 (s, 3H), 7.36 (t, J=7.6, 1H), 7.46 (t, J=7.2, 1H), 7.83 (d, J=8.0, 1H), 7.91 (d, J=8.0, 1H), 8.01 (s, 1H).

EXAMPLE 19M

Ethyl 5-cyclopropyl-1-(2,4-dichloro-6-trifluoromethylphenyl)-1H-pyrazole-4-carboxylate 43% yield.
APCIMS 393 [M+1]+
$^1$H NMR (400 MHz, CDCl$_3$) δ 0.78–0.85 (m, 2H), 0.85–0.91 (m, 2H), 1.37 (t, J=7.2, 3H), 1.70 (m, 1H), 4.30 (q, J=6.8, 2H), 7.3–7.7 (m, 2H), 8.08 (s, 1H).

EXAMPLE 19N

Ethyl 5-cyclopropyl-1-(2-chloro-4-{methylsulfonyl}phenyl)-1H-pyrazole-4-carboxylate 70% yield.
APCIMS 369 [M+1]+
$^1$H NMR (400 MHz, CDCl$_3$) δ 0.68 (d, J=4.8, 2H), 0.82 (d, J=7.6, 2H), 1.37 (t, J=7.2, 3H), 1.84 (m, 1H), 4.30 (q, J=7.2, 2H), 7.61 (d, J=8.4, 1H), 7.96 (m, 1H), 8.04 (s, 1H), 8.12 (s, 1H).

EXAMPLE 19O

Ethyl 5-cyclopropyl-1-(2-chloro-4-{methylsulfonylmethylenesulfonyl}phenyl)-1H-pyrazole-4-carboxylate 61% yield.
APCIMS 447 [M+1]+

¹H NMR (400 MHz, CDCl₃) δ 0.65 (s, 2H), 0.84 (d, J=7.2, 2H), 1.35 (t, J=7.6, 3H), 1.84 (m, 1H), 3.29, (s, 3H), 4.30 (q, J=6.8, 2H), 4.62 (s, 2H), 7.64 (d, J=7.6, 1H), 8.01 (dd, J=8.4, 2.0, 1H), 8.06 (s, 1H), 8.16 (s, 1H).

EXAMPLE 19P

Ethyl 5-cyclopropyl-1-(2,5-dichlorophenyl)-1H-pyrazole-4-carboxylate

72% yield.

APCIMS 325 [M+1]⁺

¹H NMR (400 MHz, CDCl₃) δ 0.73 (s, 2H), 0.84 (d, J=6.8, 2H), 1.34 (t, J=7.2, 3H), 1.85 (m, 1H), 4.32 (q, J=7.2, 2H), 7.39–7.47 (m, 3H), 8.02 (s, 1H).

EXAMPLE 19Q

Ethyl 5-cyclopropyl-1-(2,4-dichlorophenyl)-1H-pyrazole-4-carboxylate

72% yield.

APCIMS 325 [M+1]⁺

¹H NMR (400 MHz, CDCl₃) δ 0.73 (s, 2H), 0.84 (d, J=6.8, 2H), 1.34 (t, J=7.2, 3H), 1.85 (m, 1H), 4.32 (q, J=7.2, 2H), 7.39–7.47 (m, 3H), 8.02 (s, 1H).

EXAMPLE 19R

Ethyl 5-cyclopropyl-1-(2,3-dichlorophenyl)-1H-pyrazole-4-carboxylate

74% yield.

APCIMS 325 [M+1]⁺

¹H NMR (400 MHz, CDCl₃) δ 0.67 (s, 2H), 0.78 (s, 2H), 1.34 (t, J=7.2, 3H), 1.83 (m, 1H), 4.32 (m, 2H), 7.30–7.35 (m, 2H), 7.59 (m, 1H), 8.02 (s, 1H).

EXAMPLE 19S

Ethyl 5-cyclopropyl-1-(2-chloro-5-methylsulfonylphenyl)-1H-pyrazole-4-carboxylate 38% yield.

APCIMS 369 [M+1]⁺

¹H NMR (400 MHz, CDCl₃) δ 0.70 (s, 2H), 0.82 (d, J=7.2, 2H), 1.35 (t, J=7.2, 3H), 1.83 (m, 1H), 3.08 (s, 3H), 4.33 (q, J=7.2, 2H), 7.75 (dd, J=6.4, 2.4, 1H), 7.98–8.04 (m, 2H), 8.05 (s, 1H).

EXAMPLE 19T

Methyl 5-ethyl-1-(benzimidazol-5-yl)-1H-pyrazole-4-carboxylate

56% yield.

APCIMS 271 [M+1]⁺

¹H NMR (400 MHz, DMSO-d₆) δ 0.98–1.16 (m, 3H), 2.81–3.07 (m, 2H), 3.76 (s, 3H), 7.23 (d, J=8.4, 1H), 7.68 (bs, 2H), 7.96 (s, 1H), 8.38 (bs, 1H), 12.75 (bs, 1H).

EXAMPLE 19U

Ethyl 5-cyclopropyl-1-(benzimidazol-5-yl)-1H-pyrazole-4-carboxylate

75% yield.

APCIMS 297 [M+1]⁺

¹H NMR (400 MHz, CDCl₃) δ 0.61 (dd, J=5.4, 1.4, 2H), 0.85–0.87 (m, 2H), 1.37 (m, 3H), 1.98 (m, 1H), 4.31 (q, J=7.2, 2H), 7.44 (m, 1H), 7.76 (d, J=8.8. 1H), 7.85 (s, 1H), 8.01 (s, 1H), 8.37 (bs, 1H), 11.82 (bs, 1H).

EXAMPLE 19V

Methyl 5-ethyl-1-(3-chloroindazol-5-yl)-1H-pyrazole-4-carboxylate

63% yield.

APCIMS 305 [M+1]⁺

¹H NMR (400 MHz, CDCl₃) δ 1.16(t, J=7.6, 3H), 2.96(q, J=7.6, 2H), 3.88(s, 3H), 7.43–7.46(m, 1H), 7.53(d, J=8.8, 1H), 7.74(s, 1H), 8.06(s, 1H).

EXAMPLE 19W

Methyl 5-ethyl-1-(2-methylbenzimidazol-5-yl)-1H-pyrazole-4-carboxylate

65% yield.

APCIMS 284 [M+1]⁺

¹H NMR (400 MHz, CDCl₃) δ 1.11(t, J=7.6, 3H), 2.62(s, 3H), 2.93(q, J=7.6, 2H), 7.18(dd, J=8.4, 2.0, 1H), 7.54–7.56 (m, 2H), 8.01(s, 1H).

EXAMPLE 19X

Ethyl 5-cyclopropyl-1-(2-chloro-5-hydroxysulfonylphenyl)-1H-pyrazole-4-carboxylate 82% yield.

APCIMS 369 [M−1]⁻

¹H NMR (CDCl₃) δ 0.89–1.11 (m, 4H), 1.39 (t, J=7.2, 3H), 1.83 (q, J=7.0, 1H), 4.35 (q, J=7.0, 2H), 6.92 (bs, 1H), 7.58 (d, J=8.4, 1H), 7.91–7.95 (m, 2H), 8.44 (s, 1H).

EXAMPLE 19Y

Ethyl 5-cyclopropyl-1-(2-chloro-4-hydroxysulfonylphenyl)-1H-pyrazole-4-carboxylate 96% yield.

APCIMS 369 [M−1]⁻

¹H NMR (CDCl₃) δ 0.85–0.91 (m, 4H), 1.37 (dt, J=7.0, 5.2, 3H), 1.75–1.87 (m, 1H), 4.33 (q, J=7.0, 2H), 7.42 (d, J=8.0, 1H), 7.80 (d, J=8.0, 1H), 8.02 (s, 1H), 8.16 (s, 1H).

EXAMPLE 19Z

Ethyl 5-isopropyl-1-(5-quinolinyl)-1H-pyrazole-4-carboxylate

88% yield.

APCIMS 310 [M+1]⁺

¹H NMR (400, MHz, CDCl₃) δ 8.95 (dd, J=4, 1.6, 1H), 8.26 (d, J=8, 1H), 8.12 (s, 1H), 7.79 (t, J=8, 1H), 7.53 (m, 2H), 7.39 (dd, J=9, 4, 1H), 4.32 (q, J=7, 2H), 3.01 (m, 1H), 1.38 (t, J=7, 3H), 1.21 (m, 6H).

EXAMPLE 19AA

Ethyl 5-n-propyl-1-(5-quinolinyl)-1H-pyrazole-4-carboxylate

97% yield.

APCIMS 310 [M+1]⁺

¹H NMR (400 MHz, CDCl₃) δ 8.95 (d, J=4, 1H), 8.25 (d, J=9, 1H), 8.12 (s, 1H), 7.79 (t, J=8, 1H), 7.56 (m, 2H), 7.38 (dd, J=8, 4, 1H), 4.32 (q, J=7, 2H), 2.71 (bs, 2H), 1.36 (m, 5H), 0.70 (t, J=7, 3H).

EXAMPLE 19BB

Ethyl 5-cyclopropyl-1-(2,1,3-benzothiazol-4-yl)-1H-pyrazole-4-carboxylate

67% yield.
APCIMS 315 [M+1]$^+$
$^1$H NMR (400 MHz, CDCl$_3$) δ 8.11 (m, 2H), 7.70 (m, 2H), 4.31 (q, J=7, 2H), 1.97 (m, 1H), 1.36 (t, J=7, 3H), 0.53–0.85 (m, 4H).

EXAMPLE 19CC

Ethyl 5-cyclopropyl-1-(2-aminosulfonylphenyl)-1H-pyrazole-4-carboxylate

72% yield.
APCIMS 336 [M+1]$^+$
$^1$H NMR (400 MHz, CDCl$_3$) δ 8.17 (d, J=7, 1H), 8.04 (s, 1H), 7.69 (t, J=7, 1H), 7.63 (t, J=7, 1H), 7.42 (d, J=7, 1H), 5.81 (s, 2H), 4.29 (q, J=7, 2H), 1.80 (m, 1H), 1.34 (t, J=7, 3H), 0.4–1.0 (bs, 4H).

EXAMPLE 19DD

Ethyl 5-cyclopropyl-1-(2-methylthiophenyl)-1H-pyrazole-4-carboxylate

76% yield.
APCIMS 303 [M+1]$^+$
$^1$H NMR (400 MHz, CDCl$_3$) δ 8.02 (s, 1H), 7.43 (m, 1H), 7.30 (d, J=8, 1H), 7.23 (m, 2H), 4.27 (q, J=7, 2H), 2.36 (s, 3H), 1.86 (m, 1H), 1.34 (t, J=7, 3H), 0.75 (m, 4H).

EXAMPLE 19EE

Methyl 5-methoxymethyl-1-(5-quinolinyl)-1H-pyrazole-4-carboxylate

90% yield.
APCIMS 298 [M+1]$^+$
$^1$H NMR (300 MHz, CDCl$_3$) δ 8.99 (d, J=4, 1H), 8.30 (d, J=9, 1H), 8.20 (s, 1H), 7.83 (t, J=8, 1H), 7.71 (m, 2H), 7.43 (dd, J=9,5, 1H), 4.56 (s, 2H), 3.93 (s, 3H), 3.21 (s, 3H).

EXAMPLE 19FF

Ethyl 5-cyclopropyl-1-(isoquinolin-5-yl)-1H-pyrazole-4-carboxylate

69% yield.
APCIMS 308 [M+1]$^+$
$^1$H NMR (CDCl$_3$) δ 1.68–1.75(m, 1H), 8.07(s, 1H).

EXAMPLE 19GG

Ethyl 5-benzyloxymethyl-1-(quinolin-5-yl)-1H-pyrazole-4-carboxylate 93.5% yield.
APCIMS 388 [M+1]$^+$
$^1$H NMR (CDCl$_3$) δ 1.32–1.36(s, 3H), 8.15(s, 1H).

EXAMPLE 19HH

Methyl 5-ethyl-1-(benzotriazol-5-yl)-1H-pyrazole-4-carboxylate

95% yield
APCIMS 272 [M+1]$^+$
$^1$H NMR (CDCl$_3$) δ 1.12–1.16(t, 3H), 8.07(s, 1H).

EXAMPLE 19II

Methyl 5-ethyl-1-(indazol-6-yl)-1H-pyrazole-4-carboxylate

87% yield
APCIMS 270 [M+1]$^+$
$^1$H NMR (CDCl$_3$) δ 1.06–1.10(t, 3H); 8.07(s, 1H)

EXAMPLE 19JJ

Methyl 5-ethyl-1-(benzothiazol-6-yl)-1H-pyrazole-4-carboxylate

74% yield
APCIMS 288 [M+1]$^+$
$^1$H NMR (CDCl$_3$) δ 1.11–1.15(t, 3H), 8.20(s, 1H)

EXAMPLE 19LL

Ethyl 5-cyclobutyl-1-(quinolin-5-yl)-1H-pyrazole-4-carboxylate

93% yield
APCIMS 322 [M+1]$^+$
$^1$H NMR (CDCl$_3$) δ 3.44–3.53(m, 1H), 8.08(s, 1H)

EXAMPLE 19MM

Ethyl 5-cyclopropyl-1-(6-chloroquinolin-5-yl)-1H-pyrazole-4-carboxylate

23% yield
APCIMS 342 [M+1]$^+$
$^1$H NMR (CDCl$_3$) δ 1.70–1.80(m, 1H), 8.04(s, 1H)

EXAMPLE 19NN

Methyl 5-ethyl-1-(indazol-5-yl)-1H-pyrazole-4-carboxylate 71.5% yield
APCIMS 271 [M+1]$^+$
$^1$H NMR (CDCl$_3$) δ 1.06–1.10(t, 3H), 8.02(s, 1H)

EXAMPLE 19OO

Methyl 5-ethyl-1-(1,4-benzodioxan-6-yl)-1H-pyrazole-4-carboxylate

85% yield
APCIMS 289 [M+1]$^+$
$^1$H NMR (CDCl$_3$) δ 1.12–1.16(t, 3H), 7.96(s, 1H)

EXAMPLE 19PP

Ethyl 5-isobutyl-1-(quinolin-5-yl)-1H-pyrazole-4-carboxylate

98% yield
APCIMS 324 [M+1]$^+$
$^1$H NMR (CDCl$_3$) δ 2.68–2.70(m, 1H), 8.14(s, 1H)

EXAMPLE 19QQ

Methyl 5-ethyl-1-(1,3-benzodioxol-5-yl)-1H-pyrazole-4-carboxylate 76.6% yield
APCIMS 275 [M+1]$^+$
$^1$H NMR (CDCl$_3$) δ 1.10–1.14(t, 3H), 7.94(s, 1H)

EXAMPLE 19RR

Ethyl 5-cyclopropyl-1-(8-Bromoquinolin-5-yl)-1H-pyrazole-4-carboxylate

49% yield
APCIMS 388 [M+2]$^+$
$^1$H NMR (CDCl$_3$) δ 1.64–1.72(m, 1H), 8.04(s, 1H)

EXAMPLE 19SS

Ethyl 5-Cyclopropyl-1-(6-trifluoromethylquinolin-7-yl)-1H-pyrazole-4-carboxylate 65% yield
APCIMS 376 [M+1]$^+$
$^1$H NMR (CDCl$_3$) δ 1.81–1.88(m, 1H), 8.12(s, 1H)

EXAMPLE 19TT

Ethyl 5-methyl-1-(6-quinolinyl)-1H-pyrazole-4-carboxylate

40% yield.
$^1$H NMR (DMSO-d$_6$) d 1.26 (t, 3H); 2.57 (s, 3H); 4.22 (q, 2H); 7.6 (dd, 1H); 7.89 (dd, 1H); 8.04 (s, 1H); 8.12–8.19 (m, 2H); 8.43 (d, 1H); 8.95 (dd, 1H).

EXAMPLE 19UU

Ethyl 5-cyclopropyl-1-(6-quinolinyl)-1H-pyrazole-4-carboxylate 73.2% yield.
$^1$H NMR (DMSO-d$_6$) d 0.43 (dd, 2H); 0.83 (m, 2H); 1.29 (t, 3H); 2.18 (m, 1H); 4.24 (q, 2H); 7.61 (dd, 1H); 7.98–8.04 (dd +s, 2H); 8.12 (d, 1H); 8.26 (s, 1H); 8.46 (d, 1H); 8.96 (t, 1H);

EXAMPLE 19VV

Ethyl 5-methyl-1-(6-methoxy-5-quinolinyl)-1H-pyrazole-4-carboxylate

25% yield.
$^1$H NMR (DMSO-d$_6$) d 1.27 (t, 3H); 2.16 (s, 3H); 3.9 (s, 3H); 4.23 (q, 2H); 7.34 (dd, 1H); 7.46 (m, 1H); 7.87 (d, 1H); 8.07 (s, 1H); 8.24 (d, 1H); 8.8 (dd, 1H).

EXAMPLE 19WW

Ethyl 5-cyclopropyl-1-(6-methyl-5-quinolinyl)-1H-pyrazole-4-carboxylate 55.2% yield.
$^1$H NMR (DMSO-d$_6$) d 0.48–0.78 (m, 4H); 1.27 (t, 3H); 1.66 (m, 1H); 2.13, (s, 3H); 4.21 (q, 2H); 7.35 (dd, 1H); 7.5 (m, 1H); 7.8 (d, 1H); 8.11 (m, 2H); 8.89 (t, 1H).

EXAMPLE 19XX

Ethyl 5-ethyl-1-(2-methyl-6-guinolinyl)-1H-pyrazole-4-carboxylate 36.1% yield.
$^1$H NMR (DMSO-d$_6$) d 1.05 (t, 3H); 1.3 (t, 3H); 2.64 (s, 3H); 2.9 (q, 2H); 4.2 (2q, 2H); 7.45 (d, 1H); 7.56 (d, 1H); 7.82 (m, 3H); 8.6 (d, 1H).

EXAMPLE 19YY

Ethyl 5-ethyl-1-(6-methyl-5-quinolinyl)-1H-pyrazole-4-carboxylate 70.8% yield.
$^1$H NMR (DMSO-d$_6$) d 0.83 (t, 3H); 1.33 (t, 3H); 2.15 (s, 3H); 2.50 (2q, 2H); 4.31 (q, 2H); 7.33 (d, 1H); 7.53 (q, 1H); 7.87 (d, 1H); 8.19 (d+s, 2H); 8.95 (d, 1H).

EXAMPLE 19ZZ

Ethyl 5-ethyl-1-(6-guinolinyl)-1H-pyrazole-4-carboxylate 99.1% yield.
$^1$H NMR (DMSO-d$_6$) d 1.04 (t, 3H); 1.26 (t, 3H); 2.94 (q, 2H); 4.23 (q, 2H); 7.61 (q, 1H); 7.82 (dd, 1H); 8.03 (s, 1H); 8.15 (d, 2H); 8.47 (d, 1H); 8.97 (d, 1H).

EXAMPLE 19AAA

Methyl 1-(2-quinoxalinyl)-5-ethyl-1H-pyrazole-4-carboxylate

77% yield
$^1$H NMR (400 MHz, DMSO-d$_6$) δ 9.41 (s, 1H), 8.17 (s, 1H), 8.13 (dd, J=1.2, 8, 1H), 8.01 (dd, J=1, 8, 1H), 7.87 (m, 2H), 3.78 (s, 3H), 3.40 (q, J=7, 2H), 1.30 (t, J=7, 3H).
APCIMS 283 [M+1]$^+$

EXAMPLE 19BBB

Methyl 1-(2-benzimidazyl)-5-ethyl-1H-pyrazole-4-carboxylate

61% yield.
$^1$H NMR (400 MHz, DMSO-d$_6$) δ 13.14(s, 1H), 8.19(s, 1H), 7.63(d, J=8, 1H), 7.45(d, J=8, 1H), 7.2(m, 2H) 3.77(s, 1H), 3.52(q, J=7, 2H), 1.22(t, J=7, 3H).
APCIMS 271 [M+1]$^+$

EXAMPLE 19CCC

Ethyl 1-(2-trifluoromethyl-4-Chlorophenyl)-5-cyclopropyl-1H-pyrazole-4-carboxylate 54% yield.
$^1$H NMR (400 MHz, DMSO-d$_6$) δ 8.07 (d, J=2.4, 1H), 7.96 (d, J=3, 1H), 7.93 (d, J=2, 1H), 7.76 (d, J=8, 1H), 4.19 (q, J=7, 2H), 1.76 (m, 1s), 1.24 (t, J=7, 3H), 0.73 (d, J=8, 2H), 0.62 (d, J=4, 2H).
APCIMS 359 [M+1]$^+$

EXAMPLE 19DDD

Ethyl 1-(2-fluoro-6-trifluoromethylphenyl)-5-cyclopropyl-1H-pyrazole-4-carboxylate 70% yield.
$^1$H NMR (300 MHz, DMSO-d$_6$) δ 8.08 (s, 1H), 7.97–7.87 (m, 3H), 4.24 (q, J=7, 2H), 1.74 (m, 1H), 1.30 (t, J=7, 3H), 0.86–0.68 (m, 4H).
APCIMS 343 [M+1]$^+$

EXAMPLE 19EEE

Ethyl 1-(2-trifluoromethyl-4-fluorophenyl)-5-cyclopropyl-1H-pyrazole-4-carboxlate 72% yield.
$^1$H NMR (400 MHz, DMSO-d$_6$) δ 7.97 (s, 1H), 7.93 (dd, J=8, 3, 1H), 7.84–7.73 (m, 2H), 4.21 (q, J=7, 2H), 1.77 (m, 1H), 1.26 (t, J=7, 3H), 0.75–0.65 (m, 4H).
APCIMS 343 [M+1]$^+$

EXAMPLE 19FFF

Methyl 1-(2-guinolinyl)-5-ethyl-1H-pyrazole-4-carboxylate

82% yield $^1$H NMR (300 MHz, DMSO-d$_6$) δ 8.63 (d, J=9, 1H), 8.15 (s, 1H), 8.11–8.00 (m, 3H), 7.86 (m, 1H), 7.69 (t, J=9, 1H), 3.82 (s, 3H), 3.50 (q, J=7, 2H), 1.33 (t, J=7, 3H).

APCIMS 282 [M+1]$^+$

EXAMPLE 19GGG

Ethyl 1-(2-chloro-5-hydroxycarbonylphenyl)-5-cyclopropyl-1H-pyrazole-4-carboxylate 89% yield $^1$H NMR (300 MHz, DMSO-d6)) δ 8.11 (dd, J=2.1, 8, 1H), 8.06 (d, J=1.8, 1H), 8.040 (s, 1H), 7.88 (d, J=8, 1H), 4.25 (q, J=7, 2H), 1.87 (m, 1H), 1.30 (t, J=7, 3H), 0.800–0.74 (m, 2H), 0.70–0.64 (m, 2H).

APCIMS 335 [M+1]$^+$

EXAMPLE 19HHH

Ethyl 1-(4-benzimidazolyl)-5-cyclopropyl-1H-pyrazole-4-carboxylate

60% yield $^1$H NMR (300 MHz, DMSO-d$_6$) δ 8.28 (s, 1H), 8.01 (bs, 1H), 7.72 (bs, 1H), 7.38–7.33 (m, 2H), 4.26 (q, J=7, 2H), 2.02 (m, 1H), 1.31 (t, J=7, 3H), 0.56–0.48 (m, 4H).

APCIMS 297 [M+1]$^+$

EXAMPLE 19III

Ethyl 1-(2-chloro-5-iodophenyl)-5-cyclopropyl -1H-pyrazole-4-carboxylate

79% yield $^1$H NMR (300 MHz, CDCl$_3$) δ 8.06 (s, 1H), 7.93 (d, J=1.5, 1H), 7.76 (dd, J=1.5, 8, 1H), 7.15 (d, J=8, 1H), 4.33 (q, J=7.2, 2H), 1.88 (m, 1H), 1.39 (t, J=7.5, 3H), 0.91–0.76 (m, 4H).

APCIMS 417 [M+1]$^+$

EXAMPLE 19JJJ

Ethyl 1-phenyl-4-cyclopropyl-1H-pyrazole-3-carboxylate

76% yield

APCIMS 269 [M-1]$^-$ $^1$H NMR (300 MHz, DMSO-d$_6$) δ 8.92 (s, 1H), 7.87–7.84 (m, 2H), 7.49 (t, J=8, 2H), 7.33 (t, J=7.5, 1H), 4.28 (q, J=7, 2H), 2.54 (m, 1H), 1.32 (t, J=7, 3H), 1.00–0.91 (m, 4H).

EXAMPLE 19KKK

Ethyl 1-(2-chloro-5-methoxyphenyl)-5-cyclopropyl-1H-pyrazole-4-carboxylate

70% yield

APCIMS 321 [M+1]$^+$ $^1$H NMR (300 MHz, CDCl$_3$) δ 8.07 (s, 1H), 7.44 (d, J=9, 1H), 7.01 (m, 1H), 6.69 (d, J=3, 1H), 4.34 (q, J=7, 2H), 1.94 (m, 1H), 1.40 (t, J=7, 3H), 0.82 (bs, 4H).

EXAMPLE 19LLL

Ethyl 1-(1-isoquinolyl)-5-cyclopropyl-1H-pyrazole-4-carboxylate

15% yield

APCIMS 308 [M+1]$^+$ $^1$H NMR (400 MHz, DMSO-d$_6$) δ 8.51 (d, J=6, 1H), 8.13 (d, J=8, 1H), 8.08 (d, 6, 1H), 8.07 (s, 1H), 7.85 (t, J=9, 1H), 7.67 (t, J=8, 1H), 7.44 (d, J=8, 1H), 4.23 (q, J=7, 2H), 1.96 (m, 1H), 1.27 (t, J=7, 3H), 0.62–0.56 (m, 2H), 0.47–0.41 (m, 2H).

EXAMPLE 19MMM

Methyl 5-butyl-1-(5-quinolinyl)-1H-pyrazole-4-carboxylate

93% yield.

APCIMS 310 [M+1]$^+$ $^1$H NMR (300 MHz, CDCl$_3$) δ 9.01 (m, 1H), 8.31 (d, J=8, 1H), 8.16 (s, 1H), 7.85 (t, J=8, 1H), 7.61 (m, 2H), 7.44 (dd, J=9, 4, 1H), 3.91 (s, 3H), 2.79 (bs, 2H), 1.37 (quintet, J=8, 2H), 1.15 (quintet, 2H), 0.69 (t, J=7, 3H).

EXAMPLE 19NNN

Ethyl 5-isopropyl-1-(6-quinolinyl)-1H-pyrazole-4-carboxylate 81.1% yield.

$^1$H NMR (DMSO-d$_6$) d 1.27 (d+t, 9H); 3.17 (m, 1H); 4.23 (q, 2H); 7.63 (q, 1H); 7.75 (dd, 1H); 8.01 (s, 1H); 8.11 (d, 1H); 8.15 (d, 1H); 8.48 (dd, 1H); 8.98 (q, 1H).

EXAMPLE 19OOO

Ethyl 5-propyl-1-(6-quinolinyl)-1H-pyrazole-4-carboxylate 91.5% yield.

$^1$H NMR (DMSO-d$_6$) d 0.69 (t, 3H); 1.26 (t, 3H); 1.42 (q, 2H); 2.93 (t, 2H); 4.22 (q, 2H); 7.61 (q, 1H); 7.82 (dd, 1H); 8.04 (s, 1H); 8.16 (d+s, 2H); 8.47 (d, 1H); 8.98 (q, 1H).

The title compounds of Examples 20A–20G were prepared using procedures analogous to that described in Bajnati, A.; Hubert-Habart, M. *Bull. Soc. Chim. Fr.* 1988, 540, and Example 12A.

EXAMPLE 20A n-Butyl 1-(2,3-dimethoxyphenyl)-3-methyl-1H-pyrazole-4-carboxylate 33% yield $^1$H NMR (400 MHz, CDCl$_3$) δ 0.93(m, 3H), 1.43(m, 2H), 1.68(t, J=6.8, 2H), 2.58(s, 3H), 3.68(s, 3H), 3.89(s, 3H), 4.23(m, 2H), 6.87(m, 1H), 7.11(m, 1H), 7.23(s, 1H), 7.28(m, 1H), 8.45(s, 1H).

APCIMS 319 [M+1]$^+$

EXAMPLE 20B n-Butyl 1-(naphthalen-2-yl)-3-methyl-1H-pyrazole-4-carboxylate

24% yield $^1$H NMR (400 MHz, CDCl$_3$) δ 0.96(m, 3H), 1.46(m, 2H), 1.72(m, 2H), 2.57(s, 3H), 4.26(m, 2H), 7.49(m, 2H), 7.78–7.94(m, 4H), 8.10(s, 1H), 8.44(s, 1H).

APCIMS 309[M+1]$^+$

EXAMPLE 20C n-Butyl 1-(o-biphenyl)-3-methyl-1H-pyrazole-4-carboxylate

75% yield $^1$H NMR (400 MHz, CDCl$_3$) δ 0.88(t, J=7.6, 3H), 1.33(m, 2H), 1.56(m, 2H), 2.47(s, 3H), 4.10(m, 2H), 7.10(m, 2H), 7.26(m, 3H), 7.42(m, 4H), 7.57(m, 1H).

APCIMS 335 [M+1]$^+$

EXAMPLE 20D n-Butyl 1-phenyl-3-ethyl-1H-pyrazole-4-carboxylate

36% yield $^1$H NMR (400 MHz, CDCl$_3$) δ 0.95(t, J=7.8, 3H), 1.29(t, J=7.6, 3H), 1.43(m, 2H), 1.68(m, 2H), 2.95(q, J=7.6, 2H), 4.24(t, J=6.4, 2H), 7.27(m, 1H), 7.42 (m, 2H), 7.65(m, 2H), 8.31(s, 1H).

APCIMS 273 [M+1]$^+$

EXAMPLE 20E n-Butyl 1-(2,1,3-benzothiadiazol-4-yl)-3-methyl-1H-pyrazole-4-carboxylate 25% yield $^1$H NMR (400 MHz, CDCl$_3$) δ 0.97(t, J=7.2, 3H), 1.46(m, 2H), 1.74(m, 2H), 2.58(s, 3H), 4.28(t, J=6.8, 2H), 7.68(t, J=8.6, 1H), 7.92(d, J=8.8, 1H), 8.21 (d, J=7.2, 1H), 9.53(s, 1H).

APCIMS 217 [M+1]$^+$

EXAMPLE 20F n-Butyl 1-(indazol-7-yl)-3-methyl-1H-pyrazole-4-carboxylate

35% yield $^1$H NMR (400 MHz, DMSO-d$_6$) δ 0.90(t, J=7.4, 3H), 1.40(m, 2H), 1.64(m, 2H), 2.83(s, 3H), 4.19(t, J=6.4, 2H), 7.17(t, J=7.6, 1H), 7.72(d, J=7.6, 1H), 8.18(s, 1H), 9.03(s, 1H), 13.13(bs, 1H).

APCIMS 299 [M+1]$^+$

EXAMPLE 20G n-Butyl 1-benzyl-3-methyl-1H-pyrazole-4-carboxylate

68% yield $^1$H NMR (400 MHz, CDCl$_3$) δ 0.93(t, J=7.2, 3H), 1.40(m, 2H), 1.66(m, 2H), 2.45(s, 3H), 4.19(t, J=6.6, 2H), 5.2(s, 2H), 7.20–7.24(m, 2H), 7.32–7.36(m, 3H), 7.77(s, 1H).

APCIMS 273 [M+1]$^+$

EXAMPLE 21

Ethyl 5-cyclopropyl-1-(2-pyrrol-1-ylphenyl-)-1H-pyrazole-4-carboxylate

A mixture of ethyl 5-cyclopropyl-1-(2-nitrophenyl-)-1H-pyrazole-4-carboxylate (2.5 g, 8.3 mmol) and Pd/C (10%, 0.550 g, 20% w/w) in ethyl acetate (60 mL) was shaken under a H$_2$ atmosphere (50 psig) for 3 h. The resulting mixture was filtered through Celite® and concentrated in vacuo to afford 2.52 g of a reddish oil.

A portion of the residue (458.5 mg, 1.69 mmol) and 2,5-dimethoxytetrahydrofuran (0.328 mL, 2.53 mmol) in glacial acetic acid (6 mL) was heated to 110° C. under a N$_2$ atmosphere for 1 h. The reaction mixture was cooled to 23° C. and concentrated in vacuo. The residue was dissolved in ethyl acetate, washed twice with NaHCO$_3$ (sat aq sol) and brine, dried over MgSO$_4$, and filtered. The filtrate was passed over a short column of silica gel. The eluate was concentrated in vacuo to yield 0.4965 g (91%) of the title compound as a dark oil.

APCIMS 322 [M+1]$^+$ $^1$H NMR (400 MHz, CDCl$_3$) δ 0.35–0.80 (m, 4H), 1.01 (m, 1H), 1.36 (t, J=9.4, 3H), 4.30 (q, J=8.8, 2H), 7.42–7.61 (m, 4H), 8.08 (s, 1H).

EXAMPLE 22A

Ethyl 5-cyclopropyl-1-(2-chloro-5-{dimethylaminosulfonyl}phenyl)-1H-pyrazole-4-carboxylate A mixture of ethyl 5-cyclopropyl-1-(2-chloro-5-{hydroxysulfonyl}phenyl)-1H-pyrazole-4-carboxylate (1.48 g, 4.0 mmol) and PCl$_5$ (1.79 g, 8.6 mmol) in POCl$_3$ (6 mL) under a nitrogen atmosphere was heated at 95° C. for 30 min, cooled to 23° C. and poured slowly over ice. The resulting mixture was extracted with EtOAc. The organic layer was washed three times with cold water, brine, dried over MgSO$_4$, filtered and concentrated in vacuo to afford 1.48 g (95% yield) of ethyl 5-cyclopropyl-1-(2-chloro-5-{chlorosulfonyl}phenyl)-1H-pyrazole-4-carboxylate as a yellow oil.

A solution of ethyl 5-cyclopropyl-1-(2-chloro-5-{chlorosulfonyl}phenyl)-1H-pyrazole-4-carboxylate (0.315 g, 0.812 mmol) in CH$_2$Cl$_2$ (3 mL) was treated at 23° C. with dimethylamine (2 M in THF, 3 mL, 6 mmol). The resulting mixture was stirred for 15 min and concentrated in vacuo. The residue was partitioned between EtOAc and HCl (0.1 M aq). The organic layer was washed with brine, dried over MgSO$_4$, filtered and concentrated in vacuo. The residue was purified by Flash 40S™ chromatography (65:35 hexanes-EtOAc) to afford 0.276 g (86% yield) of desired product as a colorless oil.

APCIMS 397 [M+1]$^+$ $^1$H NMR (400 MHz, CDCl$_3$) δ 0.68 (d, J=5.6, 2H), 0.81 (d, J=8.4, 2H), 1.35 (t, J=7.2, 3H), 1.83 (m, 1H), 2.74, (s, 6H), 4.30 (q, J=7.2, 2H), 7.70–7.25 (m, 1H), 7.80–7.83 (m, 2H), 8.04 (s, 1H).

The title compounds of Examples 22B–22E were prepared using procedures analogous to that used for Example 22A.

EXAMPLE 22B

Ethyl 5-cyclopropyl-1-(2-chloro-5-{aminosulfonyl}phenyl)-1H-pyrazole-4-carboxylate 58% yield.

APCIMS 368 [M−1]$^−$ $^1$H NMR (400 MHz, CDCl$_3$) δ 0.73 (s, 2H), 0.84 (d, J=5.6, 2H), 1.37 (t, J=7.2, 3H), 1.85 (m, 1H), 4.31 (q, J=7.2, 2H), 7.69 (d, J=7.2, 1H), 7.96 (m, 2H), 8.06 (s, 1H).

EXAMPLE 22C

Ethyl 5-cyclopropyl-1-(2-chloro-5-{methylaminosulfonyl}phenyl)-1H-pyrazole-4-carboxylate 97% yield.

APCIMS 368 [M+1]$^+$ $^1$H NMR (400 MHz, CDCl$_3$) δ 0.72 (s, 2H), 0.86 (d, J=8, 2H), 1.37 (t, J=7.2, 3H), 1.85 (m, 1H), 2.70 (s, 3H), 4.32 (q, J=7.2, 2H), 7.71 (d, J=9.2, 1H), 7.90–7.93 (m, 2H), 8.06 (s, 1H).

EXAMPLE 22D

Ethyl 5-cyclopropyl-1-(2-chloro-4-{dimethylaminosulfonyl}phenyl)-1H-pyrazole-4-carboxylate 100% yield.

APCIMS 397 [M+1]⁺

¹H NMR (400 MHz, CDCl₃) δ 0.67 (bs, 2H), 0.82 (d, J=6.4, 2H), 1.35 (t, J=7.2, 3H), 1.85 (m, 1H), 2.76, (s, 6H), 4.32 (q, J=7.2, 2H), 7.57 (d, J=8.4, 1H), 7.78 (dd, J=8.4, 2.0, 1H), 7.94 (s, 1H), 8.05 (s, 1H).

EXAMPLE 22E

Ethyl 5-cyclopropyl-1-(2-chloro-4-{methylaminosulfonyl}phenyl)-1H-pyrazole-4-carboxylate 93% yield.

APCIMS 384 [M+1]⁺

¹H NMR (400 MHz, DMSO-$d_6$) δ 0.58–0.61 (m, 2H), 0.73–0.78 (m, 2H), 1.35 (t, J=6.8, 3H), 1.85 (m, 1H), 2.47, (s, 6H), 4.21 (q, J=7.2, 2H), 7.77 (dd, J=9.6, 4.8, 1H), 7.88 (s, 1H), 8.03 (d, J=3.5, 1H).

The title compounds of Examples 23A–23B were prepared using procedures analogous to that described in Kikugawa, Y. *Synthesis*, 1981, 124.

EXAMPLE 23A

Methyl 1-(1-methylbenzimidaz-2-yl)-5-ethyl-1H-pyrazole-4-carboxylate

61% yield

¹H NMR (300 MHz, DMSO-$d_6$) δ 8.23 (s, 1H), 7.78–7.69 (m, 2H), 7.45–7.32 (m, 2H), 8.83 (s, 3H), 3.72 (s, 3H), 3.04 (q, J=7, 2H), 1.14 (t, J=7, 3H).

APCIMS 285 [M+1]⁺

EXAMPLE 23B

Methyl 5-ethyl-1-(1-methylbenzimidazol-6-yl)-1H-pyrazole-4-carboxylate

35% yield.

APCIMS 284 [M+1]⁺

¹H NMR (300 MHz, CDCl₃) δ 1.03(t, J=7.35, 3H), 2.87(q, J=7.35, 2H), 3.80 (s, 3H), 3.88(s, 3H), 7.26–7.30(m, 1H), 7.78–7.81(m, 2H), 8.02(s, 1H), 8.36(s, 1H).

EXAMPLE 24

Ethyl 5-cyclopropyl-1-(2-methylsulfonylphenyl)-1H-pyrazole-4-carboxylate

A solution of ethyl 5-cyclcopropyl-1-(2-methylthiophenyl)-1H-pyrazole-4-carboxylate (0.456 g, 1.51 mmol) in methanol (6 mL) at 0° C. was treated with a solution of oxone (1.40 g, 2.27 mmol) in water (6 mL). The resulting slurry was was stirred at 23° C. for 8 h. The mixture was treated with additional oxone (0.46 g, 0.76 mmol), stirred for 14 h and partitioned between CH₂Cl₂ and water. The organic layer was washed with water, dried over MgSO₄ and concentrated in vacuo to afford 0.504 g (100%) of the title compound.

APCIMS 335 [M+1]⁺

¹H NMR (400 MHz, CDCl₃) δ 8.23 (dd, J=8, 2, 1H), 8.03 (s, 1H), 7.77 (t, J=8, 1H), 7.71 (t, J=8, 1H), 4.43 (d, J=7, 1H), 4.30 (q, J=7, 2H), 3.27 (s, 3H), 1.81 (m, 1H), 1.36 (t, J=7, 3H), 0.4–1.0 (bs, 4H).

EXAMPLE 25

Ethyl 5-cyclopropyl-1-(2-methylaminosulfonylphenyl)-1H-pyrazole-4-carboxylate and (Example 25A) Ethyl 5-cyclopropyl-1-(2-dimethylaminosulfonylphenyl)-1H-pyrazole-4-carboxylate (Example 25B)

A solution of ethyl 5-cyclcopropyl-1-(2-aminosulfonylphenyl)-1H-pyrazole-4-carboxylate (0.503 g, 1.50 mmol) in dry DMSO (5 mL) at 23° C. was treated with NaH (60% in mineral oil, 0.090 g, 2.25 mmol) and stirred for 1.5 h. The resulting mixture was treated with dimethylsulfate (0.213 mL, 2.25 mmol), stirred for 20 h and partitioned between EtOAc and water. The organic layer was dried over MgSO₄, filtered and concentrated in vacuo. The residue was purified by Flash 40M™ chromatography (hexanes-EtOAc 60:40 to 50:50) to provide 0.141 g (27%) of Example 25A and and 0.231 g (42%) of Example 25B.

EXAMPLE 25A

Ethyl 5-cyclopropyl-1-(2-methylaminosulfonylphenyl)-1H-pyrazole-4-carboxylate

APCIMS 350 [M+1]⁺

¹H NMR (400 MHz, CDCl₃) δ 8.13 (dd, J=8, 1.4, 1H), 8.04 (s, 1H), 7.71 (t, J=8, 1.6, 1H), 7.65 (t, J=8, 1.6, 1H), 7.44 (dd, 8, 1.2, 1H), 5.93 (q, J=5, 1H), 4.31 (q, J=7, 2H), 2.65 (d, J=5, 3H), 1.82 (m, 1H), 1.36 (t, J=7, 3H), 0.4–1.1 (m, 4H).

EXAMPLE 25B

Ethyl 5-cyclopropyl-1-(2-dimethylaminosulfonylphenyl)-1H-pyrazole-4-carboxylate

APCIMS 364 [M+1]⁺

¹H NMR (400 MHz, CDCl₃) δ 8.07 (dd, J=7, 2, 1H), 8.00 (s, 1H), 7.68 (m, 2H), 7.35 (dd, J=7, 2, 1H), 4.29 (q, J=7, 2H), 2.67 (s, 6H), 1.88 (m, 1H), 1.36 (t, J=7, 3H), 0.64–0.93 (m, 4H).

EXAMPLE 26A

Ethyl 1-(2-chloro-5-methylaminocarbonylphenyl)-5-cyclopropyl-1H-pyrazole-4-carboxylate A solution of ethyl 1-(2-chloro-5-hydroxycarbonylphenyl)-5-cyclopropyl-1H-pyrazole-4-carboxylate (1.32 g, 3.73 mmol) in thionyl chloride (7.5 mL) was heated at reflux for 2 h under a nitrogen atmosphere. The resulting solution was concentrated in vacuo. A solution of the residue in anhydrous CH₂Cl₂ (10 mL) under a nitrogen atmosphere was treated with methylamine (2 M solution in THF, 9.33 mL, 18.7 mmol) followed by a catalytic amount of 4-dimethylaminopyridine. The resulting mixture was stirred for 6 h and partitioned between ethyl acetate and HCl (1 M aq). The organic layer was washed with brine, NaHCO₃ (sat aq sol), and brine, dried over MgSO₄, filtered and concentrated in vacuo. The residue was purified by flash 40M™ chromatography (75:25 ethyl acetate/hexanes) to afford 1.00 g (77% yield) of the title compound.

¹H NMR (300 MHz, CDCl₃) δ 8.08 (s, 1H), 7.88 (dd, J=2, 8, 1H), 7.81 (d, J=2, 1H), 7.63 (d, J=9, 1H), 6.40 (bs, 1H), 4.33 (q, J=7, 2H), 3.02 (d, J=4, 3H), 1.89 (m, 1H), 1.40 (t, J=7, 3H), 0.92–0.75 (m, 4H).

APCIMS 348 [M+1]⁺

The title compounds of Examples 26B–26C were prepared using procedures analogous to that used for Example 26A.

EXAMPLE 26B

Ethyl 1-(2-chloro-5-dimethylaminocarbonylphenyl)-5-cyclopropyl-1H-pyrazole-4-carboxylate 45% yield ¹H NMR (300 MHz, CDCl₃) δ 8.07 (s, 1H), 7.59 (d, J=6, 1H), 7.52 (dd, J=2, 6, 1H), 7.48 (d, J=2, 1H), 4.33 (q, J=7, 2H), 3.12 (bs, 3H), 3.05 (bs, 3H), 1.88 (m, 1H), 1.39 (t, J=7, 3H), 0.94–0.80 (m, 4H).

APCIMS 362 [M+1]⁺

EXAMPLE 26C

Ethyl 1-(2-chloro-5-aminocarbonylphenyl)-5-cyclopropyl-1H-pyrazole-4-carboxylate 27% yield ¹H NMR (300 MHz, CDCl₃) δ 8.17 (s, 1H), 8.10–8.07 (m, 2H), 8.05 (s, 1H), 7.85 (d, J=9, 1H), 7.67 (s, 1H), 4.25 (q, J=7, 2H), 1.88 (m, 1H), 1.30 (t, J=7, 3H), 0.81–0.74 (m, 2H), 0.70–0.63 (m, 2H).

APCIMS 334 [M+1]⁺

The title compound of Example 27 was prepared using a procedure analogous to that used for Example 13A.

EXAMPLE 27

5-Ethyl-1-(benzothiazol-6-yl)-1H-pyrazole-4-carboxylic acid

78% yield.

APCIMS 272 [M−1]⁻

¹H NMR (DMSO-d₆) δ 0.96–1.02 (t, 3H); 7.81 (s, 1H)

The title compounds of Examples 28A–28RRR were prepared using a procedure analogous to that used for Example 14A.

EXAMPLE 28A

5-Cyclopropyl-1-(2,3-dimethoxyphenyl)-1H-pyrazole-4-carboxylic acid

83% yield

¹H NMR (400 MHz, DMSO-d₆) δ 0.68(d, J=8.4, 4H), 1.83(m, 1H), 3.54 (s, 3H), 3.85(s, 3H), 6.94(d, J=7.6, 1H), 7.19(m, 2H), 7.87(s, 1H), 12.26(s, 1H).

APCIMS 287 [M−1]⁻

EXAMPLE 28B

3-Methyl-1-(2,3-dimethoxyphenyl)-1H-pyrazole-4-carboxylic acid

81% yield

¹H NMR (400 MHz, DMSO-d₆) δ 2.38(s, 3H), 3.64(s, 3H), 3.84(s, 3H), 7.14(m, 3H), 8.41(s, 1H), 12.41(s, 1H).

APCIMS 261 [M−1]⁻

EXAMPLE 28C

5-Cyclopropyl-1-(naphthalen-1-yl)-1H-pyrazole-4-carboxylic acid

87% yield

¹H NMR (400 MHz, DMSO-d₆) δ 0.56(d, J=7.2, 4H), 1.82(m, 1H), 7.12 (d, J=7.6, 1H), 7.58(m, 4H), 8.10(m, 3H), 12.38(s, 1H).

APCIMS 279 [M+1]⁺

EXAMPLE 28D

5-Cyclopropyl-1-(naphthalen-2-yl)-1H-pyrazole-4-carboxylic acid

91% yield

¹H NMR (400 MHz, DMSO-d₆) δ 0.48(m, 2H), 0.80(m, 2H), 2.15(m, 1H), 7.58(m, 2H), 7.71(m, 1H), 8.01(m, 4H), 8.16(s, 1H), 12.35(s, 1H).

APCIMS 277 [M−1]⁻

EXAMPLE 28E

3-Methyl-1-(naphthalen-2-yl)-1H-pyrazole-4-carboxylic acid

91% yield

¹H NMR (400 MHz, DMSO-d₆) δ 2.50(s, 3H), 7.57(m, 2H), 8.06(m, 4H), 8.43(s, 1H), 9.04(s, 1H).

APCIMS 251 [M−1]⁻

EXAMPLE 28F

3-Methyl-1-(2-biphenyl)-1H-pyrazole-4-carboxylic acid

87% yield

¹H NMR (400 MHz, DMSO-d₆) δ 2.28(s, 3H), 7.05(m, 2H), 7.27(m, 3H), 7.45–7.54(m, 4H), 7.72(s, 1H).

APCIMS 277 [M−1]⁻

EXAMPLE 28G

5-Cyclopropyl-1-(o-biphenyl)-1H-pyrazole-4-carboxylic acid

75% yield

¹H NMR (400 MHz, DMSO-d₆) δ 0.44(m, 4H), 1.04(m, 1H), 6.98(m, 2H), 7.25(m, 3H), 7.44–7.62(m, 4H), 7.85(s, 1H), 12.14(s, 1H).

APCIMS 303 [M−1]⁻

EXAMPLE 28H

3-Ethyl-1-phenyl-1H-pyrazole-4-carboxylic acid

88% yield

¹H NMR (400 MHz, DMSO-d₆) δ 1.18(t, J=6.3, 3H), 2.82(q, J=7.2, 2H), 7.28(t, J=7.2, 1H), 7.44(m, 2H), 7.84(m, 2H), 8.84(s, 1H), 12.43(s, 1H).

APCIMS 215 [M−1]⁻

EXAMPLE 28I

5-Cyclopropyl-1-(2-nitrophenyl)-1H-pyrazole-4-carboxylic acid

89% yield $^1$H NMR (400 MHz, DMSO-d$_6$) δ 0.58(m, 2H), 0.77(m, 2H), 1.94(m, 1H), 7.79(m, 1H), 7.91(m, 2H), 8.13(d, J=7.6, 1H), 12.48(s, 1H).

APCIMS 273[M−1]$^-$

EXAMPLE 28J

5-Cyclopropyl-1-(2-pyrrol-1-ylphenyl)-1H-pyrazole-4-carboxylic acid

95% yield $^1$H NMR (400 MHz, DMSO-d$_6$) δ 0.41–0.62(m, 4H), 1.04(m, 1H), 6.13(m, 2H), 6.52(m, 2H), 7.50–7.71(m, 4H), 7.98(s, 1H).

APCIMS 292[M−1]$^-$

EXAMPLE 28K

5-Cyclopropyl-1-(2-ethylphenyl)-1H-pyrazole-4-carboxylic acid

73% yield $^1$H NMR (400 MHz, CDCl$_3$) δ 0.78(dd, J=8.4, 1.6, 2H), 0.88(m, 2H), 1.09 (dt, J=7.6, 1.2, 3H), 1.84(m, 1H), 2.37(q, J=7.6, 2H), 7.24(m, 2H), 7.40(m, 2H), 8.07(s, 1H).

APCIMS 255 [M−1]$^-$

EXAMPLE 28L

5-Cyclopropyl-1-(2-methylphenyl)-1H-pyrazole-4-carboxylic acid $^1$H NMR (400 MHz, CDCl$_3$) δ 0.8–0.89(m, 4H), 1.87(m, 1H), 2.09(s, 3H), 7.2–7.5(m, 4H), 8.10(s, 1H).

APCIMS 241 [M−1]$^-$

EXAMPLE 28M

5-Cyclopropyl-1-(2-chlorophenyl)-1H-pyrazole-4-carboxylic acid

55% yield.

APCIMS 261 [M+1]$^+$ $^1$H NMR (400 MHz, CDCl$_3$) δ 0.84(bs, 4H), 1.95(m, 1H), 7.41–7.52(m, 3H), 7.58(dd, J=9.4, 2.2, 1H), 8.15(s, 1H).

EXAMPLE 28N

5-Cyclopropyl-1-(2-trifluoromethoxyphenyl)-1H-pyrazole-4-carboxylic acid

100% yield.

APCIMS 311 [M−1]$^-$ $^1$H NMR (400 MHz, DMSO-d$_6$) δ 0.56(d, J=5.6, 2H), 0.71(dd, J=8.4, 4.4, 2H), 1.78(m, 1H), 7.5–7.7(m, 4H), 7.93(s, 1H), 12.38(s, 1H).

EXAMPLE 28O

5-Cyclopropyl-1-(2-fluorophenyl)-1H-pyrazole-4-carboxylic acid

84% yield.

APCIMS 245 [M−1]$^-$ $^1$H NMR (400 MHz, DMSO-d$_6$) δ 0.56(m, 2H), 0.72(m, 2H), 1.85(m, 1H), 7.35(m, 1H), 7.45(m, 1H), 7.58(m, 2H), 7.92(s, 1H).

EXAMPLE 28P

3-Methyl-1-(2,1,3-benzothiadiazol-4-yl)-1H-pyrazole-4-carboxylic acid

79% yield.

APCIMS 259 [M−1]$^-$ $^1$H NMR (400 MHz, DMSO-d$_6$) δ 2.47(s, 3H), 7.82(m, 1H), 8.05(dd, J=8.4, 2.8, 1H), 8.15(dd, J=7.6, 2.8, 1H), 9.41(s, 1H), 12.63(s, 1H).

EXAMPLE 28Q

5-Cyclopropyl-1-(indazol-7-yl)-1H-pyrazole-4-carboxylic acid

78% yield.

APCIMS 267 [M−1]$^-$ $^1$H NMR (400 MHz, DMSO-d$_6$) δ 0.47–0.51(m, 2H), 0.61–0.66(m, 2H), 1.96 (m, 1H), 7.20(t, J=7.6, 1H), 7.45(d, J=7.6, 1H), 7.87(d, J=8.0, 1H), 7.99(s, 1H), 8.19(s, 1H).

EXAMPLE 28R

3-Methyl-1-(indazol-7-yl)-1H-pyrazole-4-carboxylic acid

79% yield.

APCIMS 241 [M−1]$^-$ $^1$H NMR (400 MHz, DMSO-d$_6$) δ 2.51(s, 3H), 7.17(t, J=8.0, 1H), 7.73(d, J=8.0, 1H), 7.81(d, J=7.6, 1H), 8.22(s, 1H), 9.03(bs, 1H).

EXAMPLE 28S

5-Ethyl-1-(benzothiazol-2-yl)-1H-pyrazole-4-carboxylic acid

84% yield.

APCIMS 272 [M−1]$^-$ $^1$H NMR (400 MHz, DMSO-d$_6$) δ 1.25(t, J=6.8, 3H), 3.61(q, J=6.8, 2H), 7.41–7.53(m, 2H), 7.92(d, J=8.4, 1H), 8.08(s, 1H).

EXAMPLE 28T

5-Cyclopropyl-1-(2-chloro-4-{methylsulfonyl}phenyl)-1H-pyrazole-4-carboxylic acid 98% yield.

APCIMS 339 [M−1]$^-$ $^1$H NMR (400 MHz, DMSO-d$_6$) δ 0.68–0.70(m, 2H), 0.76–0.79(m, 2H), 1.87 (m, 1H), 3.34(s, 3H), 7.95–8.10(m, 3H), 8.29(s, 1H).

EXAMPLE 28U

5-Cyclopropyl-1-(2-chloro-4-{methylsulfonylmethylenesulfonyl}phenyl)-1H-pyrazole-4-carboxylic acid 78% yield.

APCIMS 417 [M−1]$^-$ $^1$H NMR (400 MHz, DMSO-d$_6$) δ 0.63 (m, 2H), 0.73–0.79 (m, 2H), 1.88 (m, 1H), 3.27(s, 3H), 7.99–8.16 (m, 3H), 8.30 (s, 1H).

EXAMPLE 28V

5-Cyclopropyl-1-(2-chloro-5-{dimethylaminosulfonyl}phenyl)-1H-pyrazole-4-carboxylic acid 82% yield.

APCIMS 368 [M−1]⁻

$^1$H NMR (400 MHz, DMSO-d$_6$) δ 0.61 (d, J=2.0, 2H), 0.72 (d, J=7.6, 2H), 1.86 (m, 1H), 2.63 (s, 6H), 7.92–8.01 (m, 3H), 12.44 (s, 1H).

EXAMPLE 28W

5-Cyclopropyl-1-(2-chloro-5-{aminosulfonyl}phenyl)-1H-pyrazole-4-carboxylic acid 82% yield.

APCIMS 368 [M−1]⁻

$^1$H NMR (400 MHz, DMSO-d$_6$) δ 0.65 (s, 2H), 0.75 (d, J=8.0, 2H), 1.84 (m, 1H), 7.61 (s, 1H), 7.92–7.98 (m, 2H), 12.47 (s, 1H).

EXAMPLE 28X

5-Cyclopropyl-1-(2-chloro-5-{methylaminosulfonyl}phenyl)-1H-pyrazole-4-carboxylic acid 75% yield.

APCIMS 354 [M−1]⁻

$^1$H NMR (400 MHz, DMSO-d$_6$) δ 0.62 (s, 2H), 0.73 (d, J=8.0, 2H), 1.86 (m, 1H), 2.43 (d, J=2.8, 3H), 7.67 (d, J-4.8, 1H), 7.92–7.98 (m, 3H), 12.47 (s, 1H).

EXAMPLE 28Y

5-Cyclopropyl-1-(2,5-dichlorophenyl)-1H-pyrazole-4-carboxylic acid

97% yield.

APCIMS 295 [M−1]⁻

$^1$H NMR (400 MHz, DMSO-d$_6$) δ 0.62–0.64 (m, 2H), 0.70–0.74 (m, 2H), 1.82 (m, 1H), 7.65 (dd, J=8.8, 2.4, 1H), 7.72 (d, J=8.4, 1H), 7.85 (d, J=2.4, 1H), 7.93 (s, 1H).

EXAMPLE 28Z

5-Cyclopropyl-1-(2,4-dichlorophenyl)-1H-pyrazole-4-carboxylic acid

94% yield.

APCIMS 295 [M−1]⁻

$^1$H NMR (400 MHz, DMSO-d$_6$) δ 0.64–0.65 (m, 2H), 0.71–0.74 (m, 2H), 1.83 (m, H), 7.60–7.68 (m, 3H), 7.92 (s, 1H), 12.41 (s, 1H).

EXAMPLE 28AA

5-Cyclopropyl-1-(2,3-dichlorophenyl)-1H-pyrazole-4-carboxylic acid

91% yield.

APCIMS 295 [M−1]⁻

$^1$H NMR (400 MHz, DMSO-d$_6$) δ 0.65 (s, 2H), 0.73 (s, 2H), 1.83 (m, 1H), 7.53 (t, J=8.0, 1H), 7.63 (dd, J=8.0, 1.6, 1H), 7.86 (dd, J=8.0, 1.2, 1H), 7.96 (s, 1H), 12.41 (s, 1H).

EXAMPLE 28BB

5-Cyclopropyl-1-(2-chloro-5-methylsulfonylphenyl)-1H-pyrazole-4-carboxylic acid

77% yield.

APCIMS 339 [M−1]⁻

$^1$H NMR (400 MHz, DMSO-d$_6$) δ 0.61–0.63 (m, 2H), 0.71 (d, J=6.8, 2H), 1.83 (m, 1H), 3.29 (s, 3H), 7.97–8.09 (m, 3H), 8.18 (s, 1H), 12.44 (s, 1H).

EXAMPLE 28CC

5-Ethyl-1-(benzimidazol-5-yl)-1H-pyrazole-4-carboxylic acid

82% yield.

APCIMS 255 [M−1]⁻

$^1$H NMR (400 MHz, DMSO-d$_6$) δ 0.97 (t, J=7.2, 3H), 2.84 (q, J=7.2, 2H), 7.21 (d, J=8.4, 1H), 7.65–7.69 (m, 2H), 7.88 (s, 1H), 8.33 (s, 1H).

EXAMPLE 28DD

5-Cyclopropyl-1-(2-chloro-4-{dimethylaminosulfonyl}phenyl)-1H-pyrazole-4-carboxylic acid 92% yield.

APCIMS 368 [M−1]⁻

$^1$H NMR (400 MHz, DMSO-d$_6$) δ 0.60–0.63 (m, 2H), 0.80–0.82 (m, 2H), 1.80 (m, 1H), 2.68(s, 6H), 7.70 (s, 1H), 7.78–7.97 (m, 2H), 7.97 (s, 1H).

EXAMPLE 28EE

5-Cyclopropyl-1-(2-chloro-4-{methylaminosulfonyl}phenyl)-1H-pyrazole-4-carboxylic acid 84% yield.

APCIMS 354 [M−1]⁻

$^1$H NMR (400 MHz, DMSO-d$_6$) δ 0.63 (d, J=4.8, 2H), 0.73 (d, J=8.4, 2H), 1.84 (m, 1H), 2.47(s, 3H), 7.76 (t, J=4.6, 1H), 7.88 (s, 1H), 8.00 (d, J=15.2, 1H), 12.42 (s, 1H).

EXAMPLE 28FF

5-Cyclopropyl-1-(benzimidazol-5-yl)-1H-pyrazole-4-carboxylic acid

59% yield.

APCIMS 267 [M−1]⁻

$^1$H NMR (400 MHz, DMSO-d$_6$) δ 0.50–0.54 (m, 2H), 0.71–0.76 (m, 2H), 2.05 (m, 1H), 7.33 (dd, J=9.4, 1.8, 1H), 7.66 (d, J=8.4, 1H), 7.73 (s, 1H), 7.89 (s, 1H), 8.32 (s, 1H), 12.25 (s, 1H) 12.69 (bs, 1H).

EXAMPLE 28GG

3-Methyl-1-benzyl-1H-pyrazole-4-carboxylic acid

96% yield.

APCIMS 215 [M−1]⁻

$^1$H NMR (400 MHz, DMSO-d$_6$) δ 2.29 (s, 3H), 5.26 (s, 2H), 7.25–7.38 (m, 5H), 8.27 (s, 1H), 12.18 (bs, 1H).

EXAMPLE 28HH

5-Ethyl-1-(3-chloroindazol-5-yl)-1H-pyrazole-4-carboxylic acid

85% yield.

APCIMS 289 [M−1]⁻

$^1$H NMR (400 MHz, DMSO-d$_6$) δ 0.97 (t, J=7.2, 3H), 2.83 (q, J=7.2, 2H), 7.48 (dd, J=8.8, 1.6, 1H), 7.69–7.75 (m, 2H), 7.92 (s, 1H), 12.41 (s, 1H), 13.60 (s, 1H).

EXAMPLE 28II

5-Ethyl-1-(1-methyl benzimidazol-6-yl)-1H-pyrazole-4-carboxylic acid

76% yield.

APCIMS 269 [M−1]−

$^1$H NMR (400 MHz, DMSO-$d_6$) δ 0.97 (t, J=7.6, 3H), 2.86 (q, J=7.2, 2H), 3.90 (s, 3H), 7.38 (dd, J=8.6, 2.2, 1H), 7.81–7.93 (m, 3H), 8.75 (s, 1H).

EXAMPLE 28JJ

5-Ethyl-1-(2-methyl benzimidazol-5-yl)-1H-pyrazole-4-carboxylic acid

72% yield.

APCIMS 269 [M−1]−

$^1$H NMR (400 MHz, DMSO-$d_6$) δ 0.97 (t, J=7.4, 3H), 2.49 (s, 3H), 2.81 (q, J=7.4, 2H), 7.38 (d, J=8.8, 1H), 7.50–7.55 (m, 2H), 7.88 (s, 1H), 12.36 (s, 1H), 12.61 (bs, 1H).

EXAMPLE 28KK

5-Isopropyl-1-(quinolin-5-yl)-1H-pyrazole-4-carboxylic acid

90% yield $^1$H NMR (400 MHz, DMSO-$d_6$) δ 12.51(s, 1H), 8.99(t, J=1.6, 1H), 8.24(d, J=8, 1H), 8.06(s, 1H), 7.91(t, J=8, 1H), 7.76(d, J=7, 1H), 7.58(dd, J=8, 4, 1H), 7.47(d, J=8, 1H), 2.93(quintet, J=7, 1H), 1.15(m, 6H).

APCIMS 282 [M+1]+

EXAMPLE 28LL 1-(Quinolin-5-yl)-5-n-propyl-1H-pyrazole-4-carboxylic acid

91% yield $^1$H NMR (400 MHz, CDCl$_3$) δ 9.03 (d, J=4, 1H), 8.35 (d, J=8, 1H), 8.25 (s, 1H), 7.86 (t, J=8, 1H), 7.66 (d, J=8, 1H), 7.61 (d, J=7, 1H), 7.47 (dd, J=8, 4, 1H), 2.81 (bs, 2H), 1.45 (sixtuplet, J=8, 2H), 0.75 (t, J=8, 3H).

APCIMS 282 [M+1]+

EXAMPLE 28MM

5-Cyclopropyl-1-(2-dimethylaminosulfonylphenyl)-1H-pyrazole-4-carboxylic acid

88% yield $^1$H NMR (300 MHz, DMSO-$d_6$) δ 8.01 (m, 1H), 7.91 (s, 1H), 7.84 (m, 2H), 7.60 (m, 1H), 2.64 (s, 6H), 1.81 (m, 1H), 0.59–0.77 (m, 4H).

APCIMS 336 [M+1]+

EXAMPLE 28NN

5-Cyclopropyl-1-(2-methylsulfonylphenyl)-1H-pyrazole-4-carboxylic acid

79% yield $^1$H NMR (300 MHz, DMSO-$d_6$) δ 8.15 (m, 1H), 7.83–7.99 (m, 3H), 7.75 (m, 1H), 3.34 (s, 3H), 1.86 (m, 1H), 0.5–0.9 (m, 4H).

APCIMS 307 [M+1]+

EXAMPLE 28OO

5-Cyclopropyl-1-(2-methylaminosulfonylphenyl)-1H-pyrazole-4-carboxylic acid

70% yield $^1$H NMR (300 MHz, DMSO-$d_6$) δ 8.02 (m, 1H), 7.94 (s, 1H), 7.73–7.86 (m, 2H), 7.69 (m, 1H), 6.88 (q, J=5, 1H), 2.50 (s, 3H), 1.89 (m, 1H), 0.5–0.9 (m, 4H).

APCIMS 322 [M+1]+

EXAMPLE 28PP

5-Cyclopropyl-1-(2,1,3-benzothiadiazol-4-yl)-1H-pyrazole-4-carboxylic acid

91% yield $^1$H NMR (400 MHz, CDCl$_3$) δ 8.21 (s, 1H), 8.14 (dd, J=7, 3, 1H), 7.73 (m, 2H), 2.01 (m, 1H), 0.68 (m, 2H), 0.61 (m, 2H).

APCIMS 287 [M+1]+

EXAMPLE 28QQ

5-Methyl-1-(2,4-difluorophenyl)-1H-pyrazole-4-carboxylic acid

86% yield $^1$H NMR (400 MHz, CDCl$_3$) δ 8.10 (s, 1H), 7.43 (m, 1H), 7.03 (m, 2H), 2.45 (s, 3H).

APCIMS 239 [M+1]+

EXAMPLE 28RR

5-Cyclopropyl-1-(2-aminosulfonylphenyl)-1H-pyrazole-4-carboxylic acid

93% yield $^1$H NMR (400 MHz, DMSO-$d_6$) δ 12.34(s, 1H), 8.03(m, 1H), 7.93(s, 1H), 7.73(m, 2H), 7.63(m, 1H), 7.18(s, 2H), 1.85(m, 1H), 0.3–0.9(m, 4H).

APCIMS 308 [M+1]+

EXAMPLE 28SS

5-Cyclopropyl-1-(2-methylthiophenyl)-1H-pyrazole-4-carboxylic acid

97% yield $^1$H NMR (400 MHz, DMSO-$d_6$) δ 12.27(s, 1H), 7.87(s, 1H), 7.51(t, J=8, 1H), 7.41(d, J=8, 1H), 7.34(d, J=8, 1H), 7.27(t, J=7, 1H), 2.36(s, 3H), 1.83(m, 1H), 0.65(m, 4H).

APCIMS 275 [M+1]+

EXAMPLE 28TT

5-Methyl-1-(6-guinolinyl)-1H-pyrazole-4-carboxylic acid 84.4% yield.

$^1$H NMR (DMSO-$d_6$) d 2.62 (s, 3H); 7.66 (dd, 1H); 7.95 (dd, 1H); 8.06 (s, 1H); 8.18–8.24 (m, 2H); 8.51 (d, 1H); 9.01 (t, 1H).

EXAMPLE 28UU

5-Cyclopropyl-1-(6-quinolinyl)-1H-pyrazole-4-carboxylic acid 75.5% yield.

$^1$H NMR (DMSO-d$_6$) d 0.49 (m, 2H); 0.86 (m, 2H); 2.2 (m, 1H); 7.64 (dd, 1H); 8.01 (m, 1H); 8.03 (s, 1H); 8.16 (dd, 1H); 8.28 (d, 1H); 8.49 (d, 1H); 9.0 (dd, 1H).

EXAMPLE 28VV

5-Cyclopropyl-1-(4-quinolinyl)-1H-pyrazole-4-carboxylic acid 78.2% yield.

$^1$H NMR (DMSO-d$_6$) d 0.56 (m, 2H); 0.64 (m, 2H); 1.91 (m, 1H); 7.49 (dd, 1H); 7.68 (m, 1H); 7.8 (d, 1H); 7.88 (m, 1H); 8.13 (s, 1H); 8.19 (d, 1H); 9.11 (d, 1H).

EXAMPLE 28WW

5-Methyl-1-(6-methoxy-5-quinolinyl)-1H-pyrazole-4-carboxylic acid 80.1% yield.

$^1$H NMR (DMSO-d$_6$) d 2.2 (s, 3H); 3.96 (s, 3H); 7.38 (dd, 1H); 7.52 (m, 1H); 7.92 (d, 1H); 8.08 (s, 1H); 8.3 (d, 1H); 8.86 (dd, 1H).

EXAMPLE 28XX

5-Cyclopropyl-1-(6-methoxy-5-quinolinyl)-1H-pyrazole-4-carboxylic acid 41.6% yield.

$^1$H NMR (DMSO-d$_6$) d 0.45 (m, 2H); 0.65 (m, 2H); 1.72 (m, 1H); 3.91 (s, 3H); 7.33 (d, 1H); 7.47 (m, 1H); 7.85 (d, 1H); 7.99 (s, 1H); 8.23 (d, 1H); 8.8 (dd, 1H); 12.3 (s, 1H).

EXAMPLE 28YY

5-Cyclopropyl-1-(6-methyl-5-quinolinyl)-1H-pyrazole-4-carboxylic acid 82.5% yield $^1$H NMR (DMSO-d$_6$) d 0.52–0.77 (m, 4H); 1.7 (m, 1H); 2.19 (s, 3H); 7.4 (dd, 1H); 7.57 (m, 1H); 7.85 (d, 1H); 8.15 (m, 2H); 8.93 (t, 1H).

EXAMPLE 28ZZ

5-Ethyl-1-[2-methyl-6-quinolinyl)-1H-pyrazole-4-carboxylic acid

30% yield.

$^1$H NMR (DMSO-d$_6$) d 1.06 (t, 3H); 2.71 (s, 3H); 2.95 (q, 2H); 7.55 (d, 1H); 7.82 (d, 1H); 8.02–8.13 (m, 3H); 8.38 (d, 1H).

EXAMPLE 28AAA

5-Ethyl-1-(6-methyl-5-quinolinyl)-1H-pyrazole-4-carboxylic acid 81.5% yield.

$^1$H NMR (DMSO-d$_6$) d 0.83 (t, 3H); 2.5–2.6 (2q, 2H); 2.15 (s, 3H); 7.33 (q, 1H); 7.54 (q, 1H); 7.86 (dd, 1H); 8.14 (s, 1H); 8.19 (d, 1H); 8.94 (d, 1H).

EXAMPLE 28BBB

5-Ethyl-1-(6-quinolinyl)-1H-pyrazole-4-carboxylic acid 71.9% yield.

$^1$H NMR (DMSO-d$_6$) d 1.04 (t, 3H); 2.96 (q, 2H); 7.63 (q, 1H); 7.85 (dd, 1H); 8.01 (s, 1H); 8.17 (s+d, 2H); 8.49 (d, 1H); 8.99 (q, 1H).

EXAMPLE 28CCC 1-(2-Quinoxalinyl)-5-ethyl-1H-pyrazole-4-carboxylic acid

82% yield $^1$H NMR (400 MHz, DMSO-d$_6$) δ 9.42 (s, 1H), 8.14–8.11 (m, 2H), 8.00 (d, J=8 1H), 7.91–7.83 (m, 2H), 3.44 (q, J=7, 2H), 1.29 (t, J=7, 3H).

APCIMS 267 [M−1]$^-$

EXAMPLE 28DDD 1-(2-Benzimidazyl)-5-ethyl-1H-pyrazole-4-carboxylic acid

66% yield $^1$H NMR (400 MHz, DMSO-d$_6$) δ 13.1(s, 1H), 12.74(bs, 1H), 8.12(s, 1H), 7.63(d, J=6, 1H), 7.44(d, J=6, 1H), 7.20(bs, 2H), 3.52(q, J=7, 2H), 1.21(t, J=7, 3H).

APCIMS 257 [M+1]$^+$

EXAMPLE 28EEE 1-(2-Fluoromethyl-4-chlorophenyl)-5-cyclopropyl-1H-pyrazole-4-carboxylic acid 92% yield $^1$H NMR (400 MHz, DMSO-d$_6$) δ 12.43 (bs, 1H), 8.07 (s, 1H), 7.96–7.93 (m, 2H), 7.76 (d, J=8, 1H), 1.76 (m, 1H), 0.68–0.74 (m, 4H).

APCIMS 331 [M+1]$^+$

EXAMPLE 28FFF 1-(2-Fluoro-6-trifluoromethylphenyl)-5-cyclopropyl-1H-pyrazole-4-carboxlic acid 55% yield $^1$H NMR (400 MHz, DMSO-d$_6$) δ 12.50 (s, 1H), 7.98 (s, 1H), 7.92–7.82 (m, 3H), 1.68 (m, 1H), 0.79–0.67 (m, 4H).

APCIMS 315 [M+1]$^+$

EXAMPLE 28GGG 1-(2-Trifluoromethyl-4-fluorophenyl)-5 cyclopropyl-1H-pyrazole-4-carboxylic acid 86% yield $^1$H NMR (300 MHz, DMSO-d$_6$) δ 7.97–7.93(m, 2H), 7.91–7.74(m, 2H), 1.79 (m, 1H), 0.75(d, J=9, 4H).

APCIMS 315 [M+1]$^+$

EXAMPLE 28HHH

1(1-Methylbenzimidaz-2-yl)-5-ethyl-1H-pyrazole-4-carboxylic acid

39% yield $^1$H NMR (300 MHz, DMSO-$d_6$) δ 8.17 (s, 1H), 7.77–7.70 (m, 2H), 7.47–7.32 (m, 2H), 3.72 (s, 3H), 3.04 (q, J=7, 2H), 1.13 (t, J=7, 3H).

APCIMS 269 (M−1)$^-$

EXAMPLE 28III 1-(2-Quinolinyl)-5-ethyl-1H-pyrazole-4-carboxylic acid

93% yield $^1$H NMR (300 MHz, DMSO-$d_6$) δ 12.62(s, 1H), 8.57(d, J=7, 1H), 8.05(s, 1H), 8.02–7.94(m, 3H), 7.81(t, J=5, 1H), 7.64(t, J=5, 1H), 3.47(q, J=5, 2H), 1.30–1.27(m, 3H).

APCIMS 268 [M+1]$^+$

EXAMPLE 28JJJ 1-(2-Chloro-5-methylaminocarbonylphenyl)-5-cyclopropyl-1H-pyrazole-4-carboxylic acid 87% yield $^1$H NMR (300 MHz, DMSO-$d_6$) δ 8.67 (m, 1H), 8.06 (d, J=2, 1H), 8.04 (s, 1H), 8.00 (s, 1H), 7.85 (d, J=9, 1H), 2.79 (d, J=5, 3H), 1.88 (m, 1H), 0.75–0.66 (m, 4H).

APCIMS 320 [M+1]$^+$

EXAMPLE 28KKK 1-(4-Benzimidazolyl)-5-cyclopropyl-1H-pyrazole-4-carboxylic acid 83% yield $^1$H NMR (400 MHz, DMSO-$d_6$) δ 8.24–8.20 (m, 1H), 7.98–7.89 (m, 1H), 7.77–7.64 (m, 1H), 7.33–7.21 (m, 2H), 1.96 (m, 1H), 0.64–0.47(m, 4H).

EXAMPLE 28LLL 1-(2-chloro-5-iodophenyl)-5-cyclopropyl -1H-pyrazole-4-carboxylic acid 86% yield $^1$H NMR (300 MHz, DMSO-$d_6$) δ 8.15 (s, 1H), 7.96–7.89 (m, 2H), 7.42 (dd, J=1.2, 8, 1H), 1.85 (m, 1H), 0.77–0.67 (m, 4H).

APCIMS 389 [M+1]$^+$

EXAMPLE 28MMM 1-(2-Chloro-5-aminocarbonylphenyl)-5-cyclopropyl-1H-pyrazole-4-carboxylic acid 31% yield $^1$H NMR (300 MHz, DMSO-$d_6$) δ 8.17 (s, 1H), 8.09–8.07 (m, 2H), 8.00 (s, 1H), 7.84 (d, J=9, 1H), 7.66 (s, 1H), 1.85 (m, 1H), 0.76 (d, J=8, 2H), 0.68 (d, J=5, 2H).

APCIMS 306 [M+1]$^+$

EXAMPLE 28NNN 1-(2-Chloro-5-dimethylaminocarbonylphenyl)-5-cyclopropyl-1H-pyrazole-4-carboxylic acid 45% yield $^1$H NMR (300 MHz, DMSO-$d_6$) δ 7.98 (s, 1H), 7.79 (d, J=9, 1H), 7.72 (d, J=2, 1H), 7.63 (dd, J=2, 8, 1H), 2.99 (s, 3H), 2.93 (s, 3H), 1.89 (m, 1H), 0.77–0.73 (m, 2H), 0.67–0.65 (m, 2H).

APCIMS 334 [M+1]$^+$

EXAMPLE 28OOO

1-Phenyl-4-cyclopropyl-1H-pyrazole-3-carboxylic acid

100% yield

APCIMS 229 [M+1]$^+$ $^1$H NMR (300 MHz, DMSO-$d_6$) δ 8.85 (s, 1H), 7.85–7.82 (m, 2H), 7.51–7.45 (m, 2H), 7.32 (t, J=7, 1H), 2.57 (m, 1H), 0.99–0.90 (m, 4H).

EXAMPLE 28PPP 1-(1-lsoquinolyl-5-cyclopropyl-1H-pyrazole-4-carboxylic acid

75% yield $^1$H NMR (400 MHz, DMSO-$d_6$) δ 12.45(s, 1H), 8.49(d, J=6, 1H), 8.11(d, J=8, 1H), 8.38(d, J=6, 1H), 8.01(s, 1H), 7.84(t, J=8, 1H), 7.66(t, J=8, 1H), 7.42 (d, J=9, 1H), 1.98(m, 1H), 0.57(d, J=6, 2H), 0.428(d, J=3.6, 2H).

EXAMPLE 28QQQ

5-Isopropyl-1-(6-quinolinyl)-1H-pyrazole-4-carboxylic acid 89.8% yield.

$^1$H NMR (DMSO-$d_6$) d 1.29 (d, 6H); 3.2 (m, 1H); 7.64 (q, 1H); 7.77 (dd, 1H); 7.99 (s, 1H); 8.12 (s, 1H); 8.16 (dd, 1H); 8.5 (d, 1H); 8.99 (d, 1H); 12.4 (bs, 1H).

EXAMPLE 28RRR 5-propyl-1-(6-quinolinyl)-1H-pyrazole-4-carboxylic acid 86.4% yield.

$^1$H NMR (DMSO-$d_6$) d 0.68 (t, 3H); 1.42 (q, 2H); 2.97 (t, 2H); 7.62 (q, 1H); 7.84 (t, 1H); 8.01 (s, 1H); 8.16 (d, 2H); 8.48 (d, 1H); 8.98 (d, 1H); 12.45 (bs, 1H).

The title compounds of Examples 29A–29D were prepared using procedures analogous to that used for Example 8A.

EXAMPLE 29A

[5-Cyclopropyl-1-(2,4-dichloro-6-[trifluoromethyl] phenyl)-1H-pyrazole-4-carbonyl]guanidine hydrochloride 14% yield.

APCIMS 406 [M+]$^+$ $^1$H NMR (400 MHz, DMSO-$d_6$) δ 0.83–0.86 (m, 4H); 1.79 (m, 1H); 8.21 (s, 1H); 8.44 (bs, 3H); 8.71 (bs, 2H); 11.76 (s, 1H).

EXAMPLE 29B

[5-Methoxymethyl-1-(5-guinolinyl)-1H-pyrazole-4-carbonyl]guanidine dihydrochloride 13% yield

APCIMS 325 [M+1]$^+$

¹H NMR (300 MHz, DMSO-d₆) δ 9.12 (bs, 1H), 9.03 (m, 1H), 8.81 (bs, 2H), 8.55 (bs, 2H), 8.36 (m, 1H), 7.06–8.06 (m, 4H), 4.61 (s, 2H), 3.01 (s, 3H).

EXAMPLE 29C

[1-(5-Methoxy-2-chlorophenyl)-5-cyclopropyl-1H-pyrazole-4-carbonyl]guanidine hydrochloride 17% yield

APCIMS 334 [M+1]⁺

¹H NMR (300 MHz, DMSO-d₆) δ 8.72 (bs, 2H), 8.67 (s, 1H), 8.43 (bs, 2H), 7.63 (d, J=9, 1H), 7.29 (d, J=3, 1H), 7.21 (dd, J=3, 9, 1H), 3.82 (s, 3H), 1.99 (m, 1H), 0.79 (d, J=9, 2H), 0.63 (d, J=4, 2H).

EXAMPLE 29D

[1-(5-quinolinyl)-5-butyl-1H-pyrazole-4-carbonyl]guanidine dihydrochloride

38% yield.

APCIMS 337 [M+1]⁺

¹H NMR (400 MHz, DMSO-d₆) δ 0.53(ts, J=7.0, 3H), 1.01(t, J=6.8, 2H), 1.26(s, 2H), 2.75(s, 2H), 7.72–7.79(m, 2H), 7.92(d, J=7.2, 1H), 8.03(t, J=7.8, 1H), 8.36(d, J=8.4, 1H), 8.48(bs, 2H), 8.81(bs, 2H), 9.00(s, 1H), 9.12(s, 1H), 12.169(s, 1H).

EXAMPLE 30A

[1-(Quinolin-5-yl)-5-cyclopropyl-1H-pyrazole-4-carbonyl]guanidine hydrochloride monohydrate A solution of guanidine hydrochloride (3.11 g, 32.6 mmol) in warm anhydrous ethanol (8 mL) under a nitrogen atmosphere was treated in one portion with sodium methoxide (1.76 g, 32.6 mmol). The resulting slurry was concentrated in vacuo. The residue was treated with anhydrous toluene (10 mL) and concentrated to dryness in vacuo (twice). Each time the vacuum was released to a nitrogen atmosphere. The residue was treated in one portion with ethyl 1-(quinolin-5-yl)-5-cyclopropyl-1H-pyrazole-4-carboxylate (1.00 g, 3.26 mmol) in anhydrous ethanol (8 mL). The resulting mixture was concentrated in vacuo (rotatory evaporator, 80° C. water bath). The residue was treated with anhydrous toluene (10 mL) and the resulting mixture was concentrated in vacuo (three times). The resulting solid was triturated with water (85 mL) and filtered. The solid was air-dried to provide 0.880 g (76% yield) of [1-(quinolin-5-yl)-5-cyclopropyl-1H-pyrazole-4-carbonyl]guanidine dihydrate.

APCIMS 321 [M+1]⁺

¹H NMR (400 MHz, DMSO-d₆) δ 0.51–0.53(m, 4H), 1.88–1.95(m, 1H), 7.52–7.60(m, 2H), 7.73(d, J=8, 1H), 7.86(t, J=9, 1H), 7.94(s, 1H), 8.16(d, J=9, 1H), 8.95(t, J=1.8, 1H).

A suspension of [1-(quinolin-5-yl)-5-cyclopropyl-1H-pyrazole-4-carbonyl]guanidine dihydrate (1.28 g, 3.59 mmol) in tetrahydrofuran (38:4 mL) with vigorous stirring was treated with concentrated hydrochloric acid (0.30 mL, 3.6 mmol). The mixture became homogeneous within one minute and then a solid began to precipitate. The resulting mixture was stirred vigorously for 1 h and filtered. The solid was air-dried to provide 1.11 g (82% yield) of the title compound.

APCIMS 321 [M+1]⁺

¹H NMR (400 MHz, DMSO-d₆) δ 0.42 (m, 2H), 0.59–0.61 (m, 2H), 1.88–1.95 (m, 1H), 7.57 (dd, J=9, 4, 1H), 7.67 (d, J=4, 1H), 7.82 (d, J=7, 1H), 7.90 (t, J=8, 1H), 8.22 (d, J=8, 1H), 8.38 (bs, 1H), 8.69 (bs, 2H), 8.72 (s, 1H), 8.98 (dd, J=4, 1.4, 1H).

The title compounds of Examples 30B–30M were prepared using procedures analogous to that used for Example 30A.

EXAMPLE 30B

[1-(Isoquinolin-5-yl)-5-cyclopropyl-1H-pyrazole-4-carbonyl]guanidine hydrochloride 14% yield

APCIMS 321 [M+1]⁺

¹H NMR (CDCl₃) δ 1.9–2.0(s, 1H), 8.80(s, 1H)

EXAMPLE 30C

[1-(Quinolin-5-yl)-5-benzyloxymethyl-1H-pyrazole-4-carbonyl]guanidine hydrochloride 41% yield

APCIMS 401 [M+1]⁺

¹H NMR (CDCl₃) δ 4.16(s, 2H), 8.87(s, 1H)

EXAMPLE 30D

[1-(Benzotriazole-5-yl)-5-ethyl-1H-pyrazole-4-carbonyl]guanidine hydrochloride monohydrate 49% yield

APCIMS 299 [M+1]⁺

¹H NMR (CDCl₃) δ 0.99–1.03(t, 3H), 8.61(s, 1H)

EXAMPLE 30E

[1-(Indazol-6-yl)-5-ethyl-1H-pyrazole-4-carbonyl]guanidine hydrochloride monohydrate 27% yield

APCIMS 298 [M+1]⁺

¹H NMR (CDCl₃) δ 1.01–1.05(t, 3H), 8.64(s, 1H)

EXAMPLE 30F

[1-(Quinolin-5-yl)-5-cyclobutyl-1H-pyrazole-4-carbonyl]guanidine hydrochloride

24% yield

APCIMS 335 [M+1]⁺

¹H NMR (CDCl₃ δ 3.61–3.70(m, 1H), 8.75(s, 1H)

EXAMPLE 30G

[1-(6-Chloroquinolin-5-yl)-5-cyclopropyl-1H-pyrazole-4-carbonyl]guanidine dihydrochloride 8% yield

APCIMS 354 [M+1]⁺

¹H NMR (CDCl₃) δ 1.78–1.83(m, 1H), 8.79(s, 1H)

EXAMPLE 30H

[1-(Indazol-5-yl)-5-ethyl-1H-pyrazole-4-carbonyl]guanidine hydrochloride 39.3% yield

APCIMS 298 [M+1]⁺

¹H NMR (CDCl₃) δ 0.99–1.05 (t, 3H), 8.70 (s, 1H)

EXAMPLE 30I

[1-(1,4-Benzodioxan-6-yl)-5-ethyl-1H-pyrazole-4-carbonyl]guanidine hydrochloride monohydate 27% yield
APCIMS 316 [M+1]$^+$
$^1$H NMR (CDCl$_3$) δ 1.01–1.08 (t, 3H), 8.64 (s, 1H)

EXAMPLE 30J

[1-(Quinolin-5-yl)-5-isobutyl-1H-pyrazole-4-carbonyl]guanidine hydrochloride 13.7%
APCIMS 337 [M+1]$^+$
$^1$H NMR (CDCl$_3$) δ 1.53–1.60(m, 1H), 8.97(s, 1H)

EXAMPLE 30K

[1-(1,3-Benzodioxol-5-yl)-5-ethyl-1H-pyrazole-4-carbonyl]guanidine hydrochloride monohydrate 9.4% yield
APCIMS 302 [M+1]$^+$
$^1$H NMR (CDCl$_3$) δ 0.99–1.02 (t, 3H), 8.63 (s, 1H)

EXAMPLE 30L

[1-(8-Bromoquinolin-5-yl)-5-cyclopropyl-1H-pyrazole-4-carbonyl]guanidine hydrochloride monohydrate 23% yield
APCIMS 401 [M+2]$^+$
$^1$H NMR (CDCl$_3$) δ 1.88–1.95(m, 1H), 8.71(s, 1H)

EXAMPLE 30M

[1-(6-Trifluoromethylquinolin-8-yl)-5-cyclopropyl-1H-pyrazole-4-carbonyl]guanidine hydrochloride monohydrate 18% yield
APCIMS 389 [M+1]$^+$
$^1$H NMR (CDCl$_3$) δ 1.80–1.87 (m, 1H), 8.80 (s, 1H)

The title compounds of Examples 31A–31O were prepared using procedures analogous to that used for Example 6A.

EXAMPLE 31A

[3-Methyl-1-(2-biphenyl)-1H-pyrazole-4-carbonyl]guanidine hydrochloride

61% yield.
APCIMS 320 [M+1]$^+$
$^1$H NMR (400 MHz, DMSO-d$_6$) δ 2.29 (s, 3H); 7.05 (m, 2H); 7.26 (m, 3H); 7.54 (m, 4H); 7.64 (s, 1H); 8.35 (bs, 2H); 8.51 (bs, 2H), 8.85 (s, 1H), 9.06 (s, 1H).

EXAMPLE 31B

[5-Cyclopropyl-1-(2,1,3-benzothiadiazol-4-yl)-1H-pyrazole-4-carbonyl]guanidine hydrochloride 66% yield.
APCIMS 328 [M+1]$^+$
$^1$H NMR (400 MHz, DMSO-d$_6$) δ 0.42 (m, 2H); 0.58 (m, 2H); 1.99 (m, 1H); 7.81 (m, 2H); 8.30 (d, J=8.4, 1H); 8.40 (bs, 2H); 8.69 (s, 1H), 8.70 (bs, 2H), 11.83 (s, 1H).

EXAMPLE 31C

[5-Methyl-1-(2,4-difluorophenyl)-1H-pyrazole-4-carbonyl]guanidine hydrochloride

77% yield.
APCIMS 280 [M+1]$^+$
$^1$H NMR (400 MHz, DMSO-d$_6$) δ 2.37 (s, 3H); 7.33 (m, 1H); 7.63–7.74 (m, 2H); 8.48 (bs, 2H); 8.74 (bs, 2H); 8.83 (s, 1H); 12.09 (s, 1H).

EXAMPLE 31D

[5-Cyclopropyl-1-(2-aminosulfonylphenyl)-1H-pyrazole-4-carbonyl]guanidine hydrochloride 25% yield.
APCIMS 349 [M+1]$^+$
$^1$H NMR (400 MHz, DMSO-d$_6$) δ 0.49–0.81 (m, 4H); 1.97 (m, 1H); 7.29 (bs, 2H); 7.66 (d, J=7.2, 1H); 7.77 (m, 2H), 8.07 (d, J=8, 1H); 8.43 (bs, 2H), 8.68 (s, 1H), 8.71 (bs, 2H), 11.81 (s, 1H).

EXAMPLE 31E

[5-Cyclopropyl-1-(2-methylthiophenyl)-1H-pyrazole-4-carbonyl]guanidine hydrochloride 35% yield.
APCIMS 316 [M+1]$^+$
$^1$H NMR (400 MHz, DMSO-d$_6$) δ 0.60 (m, 2H); 0.74 (m, 2H); 1.96 (m, 1H); 7.31–7.98 (m, 4H); 8.40 (bs, 2H), 8.62 (s, 1H); 8.68 (bs, 2H).

EXAMPLE 31F

[1-(2-Pyrrol-1-ylphenyl)-5-cyclopropyl-1H-pyrazole-4-carbonyl]guanidine hydrochloride 12% yield.
APCIMS 335 [M+1]$^+$
$^1$H NMR (400 MHz, DMSO-d$_6$) δ 0.32–0.53 (m, 4H), 1.04 (m, 1H), 6.09 (s, 2H), 6.49 (s, 2H), 7.49–7.69 (m, 4H), 9.05 (bs, 5H), 10.80 (s, 1h).

EXAMPLE 31G

[5-Methyl -1-(6-quinolinyl)-1H-pyrazole-4-carbonyl]guanidine hydrochloride 92.4% yield.
$^1$H NMR (DMSO-d$_6$) d 2.64 (s, 3H); 7.86 (m, 1H); 8.11 (d, 1H); 8.33 (d, 1H); 8.41 (bs+s, 3H); 8.74 (bs, 2H); 8.79 (d, 1H); 8.88 (s, 1H); 9.16 (d, 1H).

EXAMPLE 31H

[5-Cyclopropyl-1-(6-quinolinyl)-1H-pyrazole-4-carbonyl]guanidine hydrochloride 98.8% yield.
$^1$H-NMR (DMSO-d$_6$) d 0.36 (m, 2H); 0.84 (m, 2H); 2.3 (m, 1H); 7.63 (s, 1H); 7.95 (q, 1H); 8.28 (dd, 1H); 8.43 (d, 1H); 8.56 (bs, 2H); 8.79 (bs, 2H); 8.97 (d, 1H); 9.08 (s, 1H); 9.21 (d, 1H).

EXAMPLE 31I

[5-Cyclopropyl-1-(4-quinolinyl)-1H-pyrazole-4-carbonyl]guanidine hydrochloride 72.4% yield.

$^1$H NMR (DMSO-d$_6$) d 0.41 (m, 2H); 0.65 (m, 2H); 1.99 (m, 1H); 7.52 (d, 1H); 7.69 (m, 1H); 7.89 (m, 2H); 8.21 (d, 1H); 8.46 (bs, 2H); 8.76 (bs, 2H); 8.85 (d, 1H); 9.13 (t, 1H); 12.1 (s, 1H).

EXAMPLE 31J

[5-Methyl-1-(6-methoxy-5-quinolinyl)-1H-pyrazole-4-carbonyl]guanidine hydrochloride 55.9% yield.

$^1$H NMR (DMSO-d$_6$) d 2.24 (s, 3H); 3.96 (s, 3H); 7.57–7.67 (m, 2H); 8.0 (dd, 1H); 8.37 (d, 1H); 8.43 (bs, 2H); 8.73 (bs, 2H); 8.88 (s, 1H); 8.94 (d, 1H); 12.0 (s, 1H).

EXAMPLE 31K

[5-Cyclopropyl-1-(6-methoxy-5-guinolinyl)-1H-pyrazole-4-carbonyl]guanidine hydrochloride 24.1% yield.

$^1$H NMR (DMSO-d$_6$) d 0.34 (m, 1H); 0.52 (m, 1H); 0.62 (m, 2H); 1.79 (m, 1H); 3.94 (s, 3H); 7.51 (d, 1H); 7.6 (m, IH); 7.95 (d, 1H); 8.32 (d, 1H); 8.37 (bs, 2H); 8.68 (bs, 2H); 8.71 (s, 1H); 8.89 (d, 1H).

EXAMPLE 31L

[5-Cyclopropyl-1-(6-methyl-5-quinolinyl)-1H-pyrazole-4-carbonyl]guanidine hydrochloride 70.7% yield.

$^1$H NMR (DMSO-d$_6$) d 0.49–0.72 (m, 4H); 1.81 (m, IH); 2.51 (s, 3H); 7.75 (m, 2H); 7.99 (dd, 1H); 8.33 (d, 1H); 8.51 (bs, 2H); 8.81 (bs, 2H); 8.92 (s, 1H); 9.1 (t, 1H).

EXAMPLE 31M

[5-Ethyl-1-(2-methyl-6-quinolinyl)-1H-pyrazole-4-carbonyl]guanidine hydrochloride 47.6% yield.

$^1$H NMR (DMSO-d$_6$) d 1.11 (t, 3H); 2.89 (s, 3H); 3.0 (q, 2H); 7.86 (d, 1H); 8.06 (d, 1H); 8.34–8.43 (m, 4H); 8.74–8.88 (m, 4H).

EXAMPLE 31N

[5-Ethyl-1-(6-methyl-5-quinolinyl)-1H-pyrazole-4-carbonyl]guanidine hydrochloride 53.9% yield.

$^1$H NMR (DMSO-d$_6$) d 0.84 (t, 3H); 2.16 (s, 3H); 2.59 (2q, 2H); 7.61 (d, 1H); 7.72 (q, 1H); 7.99 (d, 1H); 8.32 (d, 1H); 8.5 (bs, 2H); 8.81 (bs, 2H); 9.07 (s+d, 2H).

EXAMPLE 31O

[5-Ethyl-1-(6-quinolinyl)-1H-pyrazole-4-carbonyl]guanidine hydrochloride 63.7% yield.

$^1$H NMR (DMSO-d$_6$) d 1.11 (t, 3H); 3.04 (q, 2H); 7.91 (q, 1H); 8.08 (dd, 1H); 8.38 (s, 1H); 8.42 (d, 1H); 8.5 (bs, 2H); 8.8 (bs, 2H); 8.86 (d, 1H); 8.93 (s, 1H); 9.21 (d, 1H).

EXAMPLE 32A

[5-Cyclopropyl-1-(2-trifluoromethylphenyl)-1H-pyrazole-4-carbonyl]guanidine hydrochloride monohydrate A mixture of 5-cyclopropyl-1-(2-trifluoromethylphenyl)-1H-pyrazole-4-carboxylic acid (1.00 g, 3.37 mmol) and thionyl chloride (0.739 mL, 10.1 mmol) was heated at reflux for 1 h under a nitrogen atmosphere, and concentrated in vacuo. The residue was treated with anhydrous toluene and the mixture was concentrated in vacuo (twice). A solution of the resulting thick oil in anhydrous tetrahydrofuran (2.5 mL) was added dropwise to a vigorously stirred mixture of guanidine hydrochloride (1.16 g, 12.0 mmol), sodium hydroxide (2 N aqueous, 12 mL, 24 mmol) and tetrahydrofuran (6 mL) at 23° C. The resulting mixture was heated at reflux for a 1 h, allowed to cool to room temperature and extracted twice with ethyl acetate. The combined organic extracts were dried over anhydrous sodium sulfate, filtered and concentrated in vacuo to afford 1.1 g of a pale pink solid. A suspension of the solid in water (3.2 mL) was treated with concentrated hydrochloric acid (0.273 mL, 3.28 mmol) and stirred at room temperature for 1 h. The resulting suspension was filtered. The solid was air-dried and recrystallized from water. The resulting crystalline solid was air-dried to afford 0.98 g (74% yield) of the title compound.

APCIMS 338 [M+1]$^+$ $^1$H NMR (400 MHz, DMSO-d$_6$) δ 0.57 (bs, 2H), 0.72–0.74 (m, 2H), 1.82–1.89 (m, 1H), 7.71 (d, J=8, 1H), 7.80 (t, J=8, 1H), 7.86 (t, J=7, 1H), 7.97 (d, J=7, 1H), 8.36 (bs, 2H), 8.60 (s, 1H), 8.62 (bs, 2H).

The title compounds of Examples 32B–32CCC were prepared using procedures analogous to that used for Example 16A and Example 32A.

EXAMPLE 32B

[1-(2,3-Dimethoxyphenyl)-3-methyl-1H-pyrazole-4-carbonyl]guanidine hydrochloride 82% yield

APCIMS 304 [M+1]$^+$ $^1$H NMR (400 MHz, DMSO-d$_6$) δ 2.43 (s, 3H), 3.73 (s, 3H), 3.85 (s, 3H), 7.16 (m, 3H), 8.39 (bs, 2H), 8.64 (bs, 2H), 9.27 (s, 1H), 12.12 (s, 1H).

EXAMPLE 32C

[1-(Naphthalen-1-yl)-5-cyclopropyl-1H-pyrazole-4-carbonyl]guanidine hydrochloride 84% yield

APCIMS 320 [M+1]$^+$ $^1$H NMR (400 MHz, DMSO-d$_6$) δ 0.40–0.70 (m, 4H), 1.90 (m, 1H), 7.13 (d, J=8, 1H), 7.60 (m, 3H), 8.06 (d, J=8, 1H), 8.13 (d, J=8, 1H), 8.39 (bs, 2H), 8.72 (m, 3H).

EXAMPLE 32D

[1-(Naphthalen-2-yl)-5-cyclopropyl-1H-pyrazole-4-carbonyl]guanidine hydrochloride 83% yield

APCIMS 320 [M+1]$^+$ $^1$H NMR (400 MHz, DMSO-d$_6$) δ 0.38 (d, J=4.8, 2H), 0.80 (d, J=8, 2H), 2.24 (m, 1H), 7.57 (m, 2H), 7.72 (d, J=8.4, 1H), 8.03 (m, 3H), 8.18 (s, 1H), 8.38 (bs, 2H), 8.64 (s, 1H), 8.70 (bs, 2H), 11.80 (s, 1H).

EXAMPLE 32E

[1-(Naphthalen-2-yl)-3-methyl-1H-pyrazole-4-carbonyl]guanidine hydrochloride

83% yield
APCIMS 294 [M+1]$^+$
$^1$H NMR (400 MHz, DMSO-d$_6$) δ 3.32 (s, 3H), 7.55 (m, 2H), 7.60–8.10 (m, 4H), 8.30 (s, 1H), 8.40 (bs, 2H), 8.52 (bs, 2H), 9.80 (s, 1H), 12.12 (s, 1H).

EXAMPLE 32F

[1-(o-Biphenyl)-5-cyclopropyl-1H-pyrazole-4-carbonyl]guanidine hydrochloride

72% yield.
APCIMS 346 [M+1]$^+$
$^1$H NMR (400 MHz, DMSO-d$_6$) δ 0.25–0.70 (m, 4H), 1.12 (m, 1H), 7.00 (m, 2H), 7.27 (m, 3H), 7.49–7.87 (m, 4H), 8.30 (bs, 2H), 8.56 (bs, 2H), 8.59 (s, 1H), 11.58 (s, 1H).

EXAMPLE 32G

[1-(5-Quinolinyl)-5-isopropyl-1H-pyrazole-4-carbonyl]guanidine dihydrochloride

74% yield.
APCIMS 323 [M+1]$^+$
$^1$H NMR (400 MHz, DMSO-d$_6$) δ 1.15(d, J=6.8, 6H), 3.00(m, 1H), 7.73(s, 2H), 7.91(d, J=7.2, 1H), 8.04(t, J=8, 1H), 8.38(d, J=8.4, 1H), 8.51(bs, 2H), 8.84 (bs, 2H), 8.96(s, 1H), 9.12(m, 1H), 12.01(s, 1H).

EXAMPLE 32H

[1-(5-Quinolinyl)-5-n-propyl-1H-pyrazole-4-carbonyl]guanidine dihydrochloride

78% yield.
APCIMS 323 [M+1]$^+$
$^1$H NMR (400 MHz, DMSO-d$_6$) δ 0.61 (t, J=7.4, 6H), 1.33 (m, 2H), 2.73 (m, 2H), 7.69–7.78 (m, 3H), 7.91 (d, J=7.6, 1H), 8.03 (t, J=7.2, 1H), 8.35 (d, J=8, 1H), 8.47 (bs, 2H), 8.81 (bs, 2H), 9.00 (s, 1H), 9.11 (m, 1H), 12.15 (s, 1H).

EXAMPLE 32I

[1-Phenyl-3-ethyl-1H-pyrazole-4-carbonyl]guanidine hydrochloride

63% yield.
APCIMS 258 [M+1]$^+$
$^1$H NMR (400 MHz, DMSO-d$_6$) δ 1.22 (m, 3H), 2.88 (m, 2H), 7.38 (m, 1H), 7.55 (m, 2H), 7.75 (m, 2H), 8.37 (bs, 2H), 8.52 (bs, 2H), 9.71 (s, 1H), 12.10 (s, 1H).

EXAMPLE 32J

[1-(2-Nitrophenyl)-5-cyclopropyl-1H-pyrazole-4-carbonyl]guanidine hydrochloride

76% yield.
APCIMS 315 [M+1]$^+$
$^1$H NMR (400 MHz, DMSO-d$_6$) δ 0.52 (bs, 2H), 0.80 (d, J=8.4, 2H), 2.04 (m, 1H), 7.81 (d, J=7.6, 1H), 7.91 (bs, 2H), 8.16 (d, J=8, 1H), 8.47 (bs, 2H), 8.67 (s, 1H), 8.72 (bs, 2H), 11.91 (s, 1H).

EXAMPLE 32K

[1-(2-[Dimethylaminosulfonyl]phenyl)-5-cyclopropyl-1H-pyrazole-4-carbonyl]guanidine hydrochloride 72% yield.
APCIMS 377 [M+1]$^+$
$^1$H NMR (400 MHz, DMSO-d$_6$) δ 0.49 (bs, 2H), 0.67 (d, J=6, 2H), 1.87 (m, 1H), 2.62 (s, 6H), 7.61 (d, J=2, 1H), 7.83 (m, 2H), 7.98 (m, 1H), 8.40 (bs, 2H), 8.64 (s, 1H), 8.68 (bs, 2H), 11.81 (bs, 1H).

EXAMPLE 32L

[1-(2-[Methanesulfonyl]phenyl)-5-cyclopropyl-1H-pyrazole-4-carbonyl]guanidine hydrochloride 68% yield.
APCIMS 348 [M+1]$^+$
$^1$H NMR (400 MHz, DMSO-d$_6$) δ 0.40–0.60 (m, 4H), 1.89 (m, 1H), 3.30 (s, 3H), 7.73 (d, J=6.4, 1H), 7.88 (m, 2H), 8.11 (dd, J=8, 1.6, 1H), 8.36 (bs, 2H), 8.64 (bs, 3H), 11.72 (s, 1H).

EXAMPLE 32M

[1-(2-[Methylaminosulfonyl]phenyl)-5-cyclopropyl-1H-pyrazole-4-carbonyl]guanidine hydrochloride 44% yield.
APCIMS 363 [M+1]$^+$
$^1$H NMR (400 MHz, DMSO-d$_6$) δ 0.48–0.76 (m, 4H), 1.93 (m, 1H), 2.4 (s, 3H), 7.01 (s, 1H), 7.65 (m, 1H), 7.79 (m, 2H), 7.98 (m, 1H), 8.31 (bs, 2H), 8.53 (s, 1H), 8.57 (bs, 2H), 11.58 (s, 1H).

EXAMPLE 32N

[1-(2-Ethylphenyl)-5-cyclopropyl-1H-pyrazole-4-carbonyl]guanidine hydrochloride

48% yield.
APCIMS 298 [M+1]$^+$
$^1$H NMR (400 MHz, DMSO-d$_6$) δ 0.61 (d, J=8.8, 2H), 0.71 (d, J=8.4, 2H), 0.98 (t, J=7.4, 3H), 2.26 (d, J=7.2, 2H), 7.33 (m, 2H), 7.46 (m, 2H), 8.35 (bs, 2H), 8.59 (s, 1H), 8.64 (bs, 2H), 11.70 (s, 1H).

EXAMPLE 32O

[1-(2-Methylphenyl)-5-cyclopropyl-1H-pyrazole-4-carbonyl]guanidine hydrochloride 14% yield.
APCIMS 284 [M+1]$^+$
$^1$H NMR (400 MHz, DMSO-d$_6$) δ 0.57 (bs, 2H), 0.70 (d, J=5.6, 2H), 1.96 (s, 4H), 7.20–7.60 (m, 4H), 8.40 (bs, 2H), 8.65 (s, 1H), 8.71 (bs, 2H), 11.81 (s, 1H).

EXAMPLE 32P

[1-(2-Chlorophenyl)-5-cyclopropyl-1H-pyrazole-4-carbonyl]guanidine hydrochloride 74% yield.
APCIMS 304 [M+1]$^+$
$^1$H NMR (400 MHz, DMSO-d$_6$) δ 0.55 (d, J=3.6, 2H), 0.72 (d, J=7.2, 2H), 1.90 (m, 1H), 7.4–7.8 (m, 4H), 8.36 (bs, 2H), 8.61 (s, 1H), 8.63 (bs, 2H), 11.74 (s, 1H).

EXAMPLE 32Q

[1-(2-Trifluoromethoxyphenyl)-5-cyclopropyl-1H-pyrazole-4-carbonyl]guanidine hydrochloride 87% yield.
APCIMS 354 [M+1]$^+$ ¹H NMR (400 MHz, DMSO-d₆) δ 0.48 (m, 2H), 0.74 (m, 2H), 1.89 (m, 1H), 7.4–7.8 (m, 4H), 8.36 (bs, 2H), 8.62 (bs, 3H), 11.72 (s, 1H).

EXAMPLE 32R

[1-(2-Fluorophenyl)-5-cyclopropyl-1H-pyrazole-4-carbonyl]guanidine hydrochloride 79% yield.
APCIMS 287 [M+1]⁺
¹H NMR (400 MHz, DMSO-d₆) δ 0.49 (d, J=4, 2H), 0.75 (d, J=6.8, 2H), 1.94 (bs, 1H), 7.4–7.6 (m, 4H), 8.34 (bs, 2H), 8.58 (s, 1H), 8.61 (bs, 2H), 11.71 (s, 1H).

EXAMPLE 32S

[1-(2,1,3-Benzothiadiazol-4-yl)-3-methyl-1H-pyrazole-4-carbonyl]guanidine

73% yield.
APCIMS 302 [M+1]⁺
¹H NMR (400 MHz, DMSO-d₆) δ 2.49 (s, 3H), 7.7–7.81 (m, 1H), 7.98 (dd, J=8.4, 0.8, 1H), 8.13 (dd, J=7.6, 0.6, 1H), 9.36 (s, 1H).

EXAMPLE 32T

[1-(Indazol-7-yl)-5-cyclopropyl-1H-pyrazole-4-carbonyl]guanidine hydrochloride

62% yield.
APCIMS 310 [M+1]⁺
¹H NMR (400 MHz, DMSO-d₆) δ 0.44 (dd, J=7.6, 5.2, 2H), 0.67–0.73 (m, 2H), 2.11 (m, 1H), 7.26 (t, J=10, 1H), 7.53 (d, J=8.8, 1H), 7.94 (d, J=9.6, 1H), 8.25 (s, 1H), 8.44 (bs, 2H), 8.79 (bs, 3H), 11.88 (s, 1H).

EXAMPLE 32U

[1-(Indazol-7-yl)-3-methyl-1H-pyrazole-4-carbonyl]guanidine hydrochloride

63% yield.
APCIMS 284 [M+1]⁺
¹H NMR (400 MHz, DMSO-d₆) δ 2.53(s, 3H), 7.23(t, J=7.8, 1H), 7.57(d, J=7.6, 1H), 7.78(d, J=8.0, 1H), 8.23(s, 1H), 8.40(bs, 2H), 8.51(bs, 3H), 9.76(s, 1H), 12.15(bs, 1H).

EXAMPLE 32V

[1-(Benzothiazol-2-yl)-5-ethyl-1H-pyrazole-4-carbonyl]guanidine hydrochloride

85% yield.
APCIMS 315 [M+1]⁺
¹H NMR (400 MHz, DMSO-d₆) δ 1.29(t, J=7.2, 3H), 3.61(q, J=7.6, 2H), 7.44–7.56(m, 2H), 7.96(d, J=8.4, 1H), 8.12(d, J=8.0, 1H), 8.43(bs, 2H), 8.62(bs, 2H), 8.84(s, 1H), 12.01(s, 1H).

EXAMPLE 32W

[1-(2-Chloro-4-methylsulfonylphenyl)-5-cyclopropyl-1H-pyrazole-4-carbonyl]guanidine hydrochloride 89% yield.
APCIMS 382 [M+1]⁺
¹H NMR (400 MHz, DMSO-d₆) δ 0.572(dd, J=5.6, 2.0, 2H), 0.76(dd, J=8.8, 2.0, 2H), 1.91(m, 1H), 3.36(s, 3H), 7.94(d, J =8.4, 1H), 8.05(dd, J=8.4, 2.0 1H), 8.26(s, 1H), 8.36(bs, 2H), 8.63(bs, 2H), 8.67(s, 1H), 11.80(s, 1H).

EXAMPLE 32X

[1-(2-Chloro-4-{methylsulfonylmethylenesulfonyl}phenyl)-5-cyclopropyl-1H-pyrazole-4-carbonyl]guanidine hydrochloride 72% yield.
APCIMS 460 [M+1]⁺
¹H NMR (400 MHz, DMSO-d₆) δ 0.53(m, 2H), 0.77(m, 2H), 1.94(m, 1H), 3.23(s, 3H), 5.91(s, 2H), 7.96–8.00(m, 1H), 8.01–8.12(m, 1H), 8.30(bs, 2H), 8.65 (bs, 2H), 8.66(s, 1H), 11.11.73(d, J=6.4, 1H).

EXAMPLE 32Y

[1-(2-Chloro-5-{dimethylaminosulfonyl}phenyl)-5-cyclopropyl-1H-pyrazole-4-carbonyl]guanidine hydrochloride 85% yield.
APCIMS 411 [M+1]⁺
¹H NMR (400 MHz, DMSO-d₆) δ 0.52(s, 2H), 0.74(m, 2H), 1.93(m, 1H), 2.45(s, 6H), 7.92–8.08(m, 3H), 8.35(bs, 2H), 8.64(bs, 3H), 11.73(s, 1H).

EXAMPLE 32Z

[1-(2-Chloro-5-{aminosulfonyl}phenyl)-5-cyclopropyl-1H-pyrazole-4-carbonyl]guanidine hydrochloride 9% yield.
APCIMS 383 [M+1]⁺
¹H NMR (400 MHz, DMSO-d₆) δ 0.57(d, J=8.6, 2H), 0.78(d, J=8.0, 2H), 1.94(m, 1H), 7.14(t, J=51.0, 2H), 7.63(s, 2H), 7.97(m, 2H), 8.36(bs, 2H), 8.62 (bs, 3H), 8.64(s, 1H), 11.73(s, 1H).

EXAMPLE 32AA

[1-(2-Chloro-5-{methylaminosulfonyl}phenyl)-5-cyclopropyl-1H-pyrazole-4-carbonyl]guanidine hydrochloride 61% yield.
APCIMS 397 [M+1]⁺
¹H NMR (400 MHz, DMSO-d₆) δ 0.53(m, 2H), 0.72–0.76 (m, 2H), 1.92(m, 1H), 2.43(d, J=5.2, 3H), 7.70(d, J=5.2, 1H), 7.93–7.99 (m, 3H), 8.35(bs, 2H), 8.60 (bs, 2H), 8.61(s, 1H), 11.70(s, 1H).

EXAMPLE 32BB

[1-(2,5-Dichlorophenyl)-5-cyclopropyl-1H-pyrazole-4-carbonyl]guanidine hydrochloride 84% yield.
APCIMS 338 [M+1]⁺
¹H NMR (400 MHz, DMSO-d₆) δ 0.58 (s, 2H), 0.77(d, J=7.2, 2H), 1.92(m, 1H), 7.70–7.77(m, 2H), 7.90 (d, J=2.4, 1H), 8.37(bs, 2H), 8.62(bs, 3H), 11.74(s, 1H).

EXAMPLE 32CC

[1-(2,4-Dichlorophenyl)-5-cyclopropyl-1H-pyrazole-4-carbonyl]guanidine hydrochloride 62% yield.
APCIMS 338 [M+1]⁺

¹H NMR (400 MHz, DMSO-d₆) δ 0.54–0.56(m, 2H), 0.73–0.78(m, 2H), 1.90 (m, 1H), 7.61–7.70(m, 2H), 7.93 (s, 1H), 8.35(bs, 2H), 8.60(bs, 3H), 11.72 (s, 1H).

EXAMPLE 32DD

[1-(2,3-Dichlorophenyl)-5-cyclopropyl-1H-pyrazole-4-carbonyl]guanidine hydrochloride 44% yield.

APCIMS 339 [M+1]⁺

¹H NMR (400 MHz, DMSO-d₆) δ 0.56–0.58(m, 2H), 0.76(s, 2H), 1.93(m, 1H), 7.57(dt, J=7.6, 2.0, 1H), 7.67(td, J=8.0, 1.6, 1H), 7.89(td, J=8.0, 1.6, 1H), 8.42(bs, 2H), 8.68(bs, 3H), 11.86(s, 1H).

EXAMPLE 32EE

[1-(2-Chloro-5-methylsulfonylphenyl)-5-cyclopropyl-1H-pyrazole-4-carbonyl]guanidine hydrochloride 86% yield.

APCIMS 382 [M+1]⁺

¹H NMR (400 MHz, DMSO-d₆) δ 0.57(s, 2H), 0.77(d, J=7.2, 2H), 1.94(m, 1H), 3.36 (s, 3H), 8.04(d, J=8.4, 1H), 8.12(d, J=8.4, 1H), 8.23(s, 1H)c 8.36(bs, 2H), 8.61(bs, 2H), 8.64(s, 1H), 11.86(s, 1H).

EXAMPLE 32FF

[1-(Benzimidazol-5-yl)-5-ethyl-1H-pyrazole-4-carbonyl]guanidine dihydrochloride

24% yield.

APCIMS 298 [M+1]⁺

¹H NMR (400 MHz, DMSO-d₆) δ 1.04(t, J=7.2, 3H), 2.88(q, J=7.2, 2H), 7.63(d, J=8.8, 1H), 8.01(bs, 2H), 8.47(bs, 2H), 8.78(bs, 2H), 8.86(s, 1H), 9.55 (bs, 1H), 12.09(s, 1H).

EXAMPLE 32GG

[1-(2-Chloro-4-{dimethylaminosulfonyl}phenyl)-5-cyclopropyl-1H-pyrazole-4-carbonyl]guanidine hydrochloride 68% yield.

APCIMS 411 [M+1]⁺

¹H NMR (400 MHz, DMSO-d₆) δ 0.52(d, J=4.4, 2H), 0.75(d, J=8.4, 2H), 1.93(bs, 1H), 2.67(s, 6H), 7.84–8.00(m, 2H), 8.04(s, 1H), 8.37(bs, 2H), 8.68(bs, 3H), 11.82(s, 1H).

EXAMPLE 32HH

[1-(2-Chloro-4-{methylaminosulfonyl}phenyl)-5-cyclopropyl-1H-pyrazole-4-carbonyl]guanidine hydrochloride 26% yield.

APCIMS 397 [M+1]⁺

¹H NMR (400 MHz, DMSO-d₆) δ 0.55–0.58(m, 2H), 0.75–0.80(m, 2H), 1.93 (m, 1H), 3.47(s, 3H), 7.82(t, J=4.8, 1H), 7.88–8.01 (m, 2H), 8.05(s, 1H), 8.34(bs, 2H), 8.57(bs, 2H), 8.06(s, 1H), 11.66(s, 1H).

EXAMPLE 32II

[1-(Benzimidazol-5-yl)-5-cyclopropyl-1H-pyrazole-4-carbonyl]guanidine dihydrochloride 16% yield.

APCIMS 310 [M+1]⁺

¹H NMR (400 MHz, DMSO-d₆) δ 0.37–0.41(m, 2H), 0.75–0.82(m, 2H), 2.19 (m, 1H), 7.75(d, J=8.8, 1H), 7.91–7.98(m, 2H), 8.05(s, 1H), 8.45(bs, 2H), 8.70 (s, 1H), 8.76(bs, 2H), 9.51(s, 1H), 11.95(s, 1H).

EXAMPLE 32JJ

[1-Benzyl-3-methyl-1H-pyrazole-4-carbonyl]guanidine hydrochloride

67% yield.

APCIMS 258 [M+1]⁺

¹H NMR (400 MHz, DMSO-d₆) δ 2.31(s, 3H), 5.29(s, 2H), 7.23–7.35(m, 5H), 8.47(bs, 2H), 8.53(bs, 2H), 8.55(s, 1H), 11.73(s, 1H.

EXAMPLE 32KK

[1-(3-Chloroindazol-5-yl)-5-ethyl-1H-pyrazole-4-carbonyl]guanidine hydrochloride 66% yield.

APCIMS 332 [M+1]⁺

¹H NMR (400 MHz, DMSO-d₆) δ 1.03(d, J=10.4, 3H), 2.84(d, J=7.6, 2H), 7.49 (d, J=8.4, 1H), 7.72 (d. J=8.8, 1H), 7.79(s, 1H), 8.41(bs, 2H), 8.73(bs, 2H), 8.76(s, 1H), 11.95(s, 1H), 13.69(s, 1H).

EXAMPLE 32LL

[1-(1-Methylbenzimidazol-6-yl)-5-ethyl-1H-pyrazole-4-carbonyl]guanidine dihydrochloride 53% yield.

APCIMS 312 [M+1]⁺

¹H NMR (400 MHz, DMSO-d₆) δ 1.02(m, 3H), 2.84(d, J=7.6, 2H), 4.03(s, 3H), 7.64(d, J=8.8, 1H), 8.00(d, J=8.4, 1H), 8.20(s, 1H), 8.47(bs, 2H), 8.78(bs, 2H), 8.87(s, 1H), 9.50(bs, 1H), 12.12(s, 1H).

EXAMPLE 32MM

[1-(2-Methylbenzimidazol-5-yl)-5-ethyl-1H-pyrazole-4-carbonyl]guanidine dihydrochloride 38% yield.

APCIMS 312 [M+1]⁺

¹H NMR (400 MHz, DMSO-d₆) δ 1.05 (bs, 3H), 2.79(s, 3H), 2.88(q, J=7.6, 2H), 7.60(dd, J=8.8, 1.6, 1H), 7.93(m, 2H), 8.46 (bs, 2H), 8.77 (bs, 2H), 8.85(s, 1H), 12.09(s, 1H).

EXAMPLE 32NN

[1-(Benzothiazol-6-yl)-5-ethyl-1H-pyrazole-4-carbonyl]guanidine hydrochloride monohydrate 9.5% yield

APCIMS 315 [M+1]⁺

¹H NMR (CDCl₃) δ 1.01–1.14(t, 3H), 8.74(s, 1H)

EXAMPLE 32OO

[1-(2-Quinoxalinyl)-5-ethyl-1H-pyrazole-4-carbonyl]guanidine dihydrochloride

44% yield.

APCIMS 310 [M+1]⁺

¹H NMR (400 MHz, DMSO-d₆) δ 11.93(s, 1H), 9.44(s, 1H), 8.86(s, 1H), 8.64(bs, 2H), 8.40(bs, 2H), 8.16(d, J=8,

1H), 8.043(dd, J=2.4, 8, 1H), 7.94–7.87 (m, 2H), 3.43(q, J=6, 2H), 1.338(t, J=7, 3H).

EXAMPLE 32PP

[1-(2-Benzimidazyl)-5-ethyl-1H-pyrazole-4-carbonyl]guanidine dihydrochloride

44% yield.

APCIMS 298 [M+1]$^+$ $^1$H NMR (400 MHz, DMSO-d$_6$) δ 12.15(s, 1H), 8.97(s, 1H), 8.73(bs, 2H), 8.47(bs, 2H), 7.56(dd, J=3, 6, 2H), 7.22(dd, J=3.2, 6, 2H), 3.53(q, J=7, 2H), 1.24 (t, J=7, 3H).

EXAMPLE 32QQ

[1-(2-Trifluoromethyl-4-chlorophenyl)-5-cyclopropyl-1H-pyrazole-4-carbonyl]guanidine hydrochloride 60% yield.

APCIMS 372 [M+1]$^+$ $^1$H NMR (300 MHz, DMSO-d$_6$) δ 8.68(bs, 3H), 8.43(bs, 2H), 8.14(s, 1H), 8.02(d, J=8, 1H), 7.84 (d, J=9, 1H), 1.90(m, 1H), 0.80(d, J=8, 2H), 0.693(d, J=4, 2H).

EXAMPLE 32RR

[1-(2-Fluoro-6-trifluoromethylphenyl)-5-cyclopropyl-1H-pyrazole-4-carbonyl]guanidine hydrochloride 71% yield

APCIMS 356 [M+1]$^+$ $^1$H NMR (300 MHz, DMSO-d$_6$) δ 8.71–8.44 (m, 5H), 8.00–7.90 (m, 3H), 1.82 (m, 1H), 0.89–0.70 (m, 4H).

EXAMPLE 32SS

[1-(2-Trifluoromethyl-4-fluorophenyl)-5 cyclopropyl-1H-pyrazole-4-carbonyl]guanidine hydrochloride 58% yield

APCIMS 356 [M+1]$^+$ $^1$H NMR (300MHz, DMSO-d$_6$) δ 8.67 (bs, 3H), 8.43 (bs, 2H), 7.99 (d, J=8, 1H), 7.90–7.78 (m, 2H), 1.89 (m, 1H), 0.81–0.63 (m, 4H).

EXAMPLE 32TT

[1-(1-Methylbenzimidaz-2-yl)-5-ethyl-1H-pyrazole-4-carbonyl]guanidine dihydrochloride 86% yield

APCIMS 312 [M+1]$^+$ $^1$H NMR (400 MHz, DMSO-d$_6$) δ 12.10(s, 1H), 8.96(s, 1H), 8.71(bs, 2H), 8.44(bs, 2H), 7.69(dd, J=8,16, 2H) 7.40–7.29(m, 2H), 3.68(s, 3H), 3.03(q, J=7, 2H), 1.12(t, J=7, 3H).

EXAMPLE 32UU

[1-(2-Quinolinyl)-5-ethyl-1H-pyrazole-4-carbonyl] guanidine dihydrochloride

65% yield

APCIMS 309 [M+1]$^+$ $^1$H NMR (400 MHz, DMSO-d$_6$) δ 11.86(s, 1H), 8.79(s, 1H), 8.65(bs, 2H), 8.61(d, J=9, 1H), 8.38(bs, 2H), 8.07(d; J=8, 1H), 8.01–7.96(m, 2H), 7.83(m, 1H), 7.66(t, J=7, 1H), 3.44(q, J=7, 2H), 1.31(t, J=7, 3H).

EXAMPLE 32VV

[1-(2-Chloro-5-methylaminocarbonylphenyl)-5-cyclopropyl-1H-pyrazole-4-carbonyl]guanidine hydrochloride 57% yield

APCIMS 359 [M–1]$^-$ $^1$H NMR (400 MHz, DMSO-d$_6$) δ 11.71 (s, 1H), 8.67 (m, 1H), 8.61 (bs, 3H), 8.36 (bs, 2H), 8.04 (d, J=7, 1H) 8.03 (s, 1H), 7.84 (d, J=8, 1H), 2.60 (d, J=4, 3H), 1.94 (m, 1H), 0.75 (d, J=7, 2H), 0.57 (m, 2H).

EXAMPLE 32WW

[1-(4-Bezimidazolyl)-5-cyclopropyl-1H-pyrazole-4-carbonyl]guanidine dihydrochloride 22% yield

APCIMS 310 [M+1]$^+$ $^1$H NMR (300 MHz, DMSO-d$_6$) δ 9.19 (bs, 2H), 8.84 (d, J=2, 1H), 8.80 (s, 1H), 8.45 (bs, 2H), 7.92 (m, 1H), 7.69–7.58 (m, 2H), 2.16 (m, 1H), 0.72 (d, J=9, 2H), 0.44 (d, J=5, 2H).

EXAMPLE 32XX

[1-(2-Chloro-5-iodophenyl)-5-cyclopropyl-1H-pyrazole-4-carbonyl]guanidine hydrochloride 81% yield

APCIMS 430 [M+1]$^+$ $^1$H NMR (300 MHz, DMSO-d$_6$) δ 8.66 (bs, 2H), 8.64 (s, 1H), 8.40 (bs, 2H), 8.18 (d, J=2, 1H), 7.94 (dd, J=2, 8, 1H), 7.45 (d, J=8, 1H), 1.94 (m, 1H), 0.84–0.72 (m, 2H), 0.68–0.58 (m, 2H).

EXAMPLE 32YY

[1-(2-Chloro-5-aminocarbonylphenyl)-5-cyclopropyl-1H-pyrazole-4-carbonyl]guanidine hydrochloride 45% yield

APCIMS 347 [M+1]$^+$ $^1$H NMR (300 MHz, DMSO-d$_6$) δ 8.65 (bs, 2H), 8.62 (s, 1H), 8.37 (bs, 2H), 8.20 (s, 1H), 8.10 (s, 1H), 8.02 (d, J=8, 1H), 7.87 (d, J=9, 1H), 7.68 (s, 1H), 1.96 (m, 1H), 0.80 (d, J=8, 2H), 0.61 (d, J=3, 2H).

EXAMPLE 32ZZ

[1-(2-Chloro-5-dimethylaminocarbonylphenyl)-5-cyclopropyl-1H-pyrazole-4-carbonyl]guanidine hydrochloride 49% yield

APCIMS 375 [M+1]$^+$ $^1$H NMR (300 MHz, DMSO-d$_6$) δ 8.60 (bs, 3H), 8.38 (bs, 2H), 7.82 (d, J=8, 1H), 7.76 (d, J=2, 1H), 7.66 (m, 1H), 2.99 (s, 3H), 2.93 (s, 3H), 1.96 (m, 1H), 0.79 (d, J=9, 2H), 0.60 (d, J=4, 2H).

EXAMPLE 32AAA

[1-Phenyl-4-cyclopropyl-1H-pyrazole-3-carbonyl] guanidine hydrochloride

22% yield

APCIMS 270 [M+1]$^+$

¹H NMR (300 MHz, DMSO-d₆) δ 9.56 (bs, 1H), 8.45 (bs, 4H), 7.74 (d, J=8, 2H), 7.56 (t, J=8, 2H), 7.40 (t, J=7, 1H), 2.62 (m, 1H), 0.99–0.94 (m, 4H).

EXAMPLE 32BBB

[1-(1-Isoquinolyl-5-cyclopropyl-1H-pyrazole-4-carbonyl]guanidine dihydrochloride 69% yield
APCIMS 321 [M+1]⁺
¹H NMR (400 MHz, DMSO-d₆) δ 11.99 (s, 1H), 8.79 (s, 1H), 8.77 (bs, 2H), 8.51 (d, J=6, 1H), 8.49 (bs, 2H), 8.13 (d, J=8, 1H), 8.10 (d, J=6, 1H), 7.85 (dd, J=7, 8, 1H), 7.9–7.6 (bs, 1H), 7.69 (dd, J=7, 8, 1H), 7.46 (d, J=8, 1H), 2.05 (m, 1H), 0.61–0.57 (m, 2H), 0.37–0.33 (m, 2H).

EXAMPLE 32CCC

[1-(2,3-Dimethoxyphenyl)-5-cyclopropyl-1H-pyrazole-4-carbonyl]guanidine hydrochloride 38% yield.
APCIMS 330 [M+1]⁺
¹H NMR (400 MHz, DMSO-d₆) δ 0.57 (d, J=4.8, 2H), 0.72 (d, J=8.4, 2H), 1.91 (m, 1H), 3.57 (s, 3H), 3.86 (s, 3H), 6.97 (d, J=8, 1H), 7.22 (m, 2H), 8.34 (bs, 2H), 8.56 (s, 1H), 8.65 (bs, 2H), 11.67 (s, 1H).

EXAMPLE 33A

N-tert-Butoxycarbonyl-N'-[5-isopropyl-1-(6-quinolinyl)-1H-pyrazole-4-carbonyl]guanidine To a solution of 5-isopropyl-1-(6-quinolinyl)-1H-pyrazole-4-carboxylic acid (336.7 mg, 1.2 mmol) in 5 ml dimethylformamide was added N,N-diisopropylethylamine (0.42 ml, 2.39 mmol), benzotriazol-1-yloxy-tris (dimethylamino)phosphonium hexafluorophosphate (BOP reagent) (582 mg, 1.32 mmol) and tert-butoxycarbonylguanidine (210 mg, 1.32 mmol). The resulting solution was stirred at room temperature for 2 h, then heated to 60° C. for 2 h. The reaction mixture was then cooled to room temperature and concentrated to dryness in vacuo. The solid residue was partitioned between ethyl acetate and water. The ethyl acetate layer was washed with brine, dried (sodium sulfate) and concentrated to dryness in vacuo. The solid residue was triturated with methanol (1.5 ml), filtered, washed with diethyl ether and dried to yield the title compound as a white solid (114.3 mg, 22.5% yield).

¹H NMR (DMSO-d₆) d 1.27 (d, 6H); 1.42 (s, 9H); 3.28 (m, 1H); 7.62 (q, 1H); 7.74 (q, 1H); 8.08–8.15 (m, 4H); 8.47 (d, 1H); 8.98 (d, 1H); 9.21 (bs, 1H); 10.9 (bs, 1H).

The title compound of Example 33B was obtained using a procedure analogous to that used for Example 33A.

EXAMPLE 33B

N-tert-butoxycarbonyl-N'[5-propyl-1-(6-quinolinyl)-1H-pyrazole-4-carbonyl]guanidine 58.9% yield.
¹H NMR (DMSO-d₆) d 0.73 (t, 3H); 1.24 (d, 2H); 1.47 (s, 9H); 3.08 (t, 2H); 7.66 (q, 1H); 7.86 (q, 1H); 8.18 (m, 3H); 8.51 (s+d, 2H); 9.01 (t, 1H); 9.39 (bs, 1H); 11.0 (bs, 1H).

EXAMPLE 34A

[5-Isopropyl-1-(6-guinolinyl)-1H-pyrazole-4-carbonyl]guanidine trifluoroacetate

A solution of N-tert-butoxycarbonyl-N'-[5-isopropyl-1-(6-quinolinyl)-1H-pyrazole-4-carbonyl]guanidine (114.3 mg, 0.27 mmol) in 2 ml of dichloromethane containing 20% trifluoroacetic acid was stirred at room temperature overnight and treated with ether. The resulting precipitate was filtered, yielding the title compound as a white solid (104.3 mg, 70% yield).

¹H NMR (DMSO-d₆) d 1.29 (d, 6H); 3.23 (m, 1H); 7.68 (q, 1H); 7.8 (dd, 1H); 8.18–8.55 (m, 7H); 9.04 (t, 1H); 11.1 (s, 1H).

The title compound of Example 34B was obtained using a procedure analogous to that used for Example 34A.

EXAMPLE 34B

[5-propyl-1-(6-quinolinyl)-1H-pyrazole-4-carbonyl]guanidine trifluoroacetate 81.2% yield. ¹NMR (DMSO-d₆) d 0.72 (t, 3H); 1.47 (d, 2H); 2.97 (t, 2H); 7.67 (t, 1H); 7.87 (d, 1H); 8.19–8.37 (m, 7H); 8.53 (d, 1H); 9.03 (s, 1H); 11.1 (s, 1H).

What is claimed is:

1. A compound having the Formula I

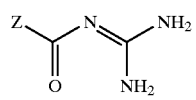

Formula I a prodrug thereof, or a pharmaceutically acceptable salt of said compound or of said prodrug, wherein Z is

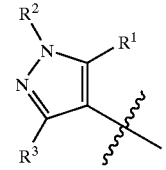

wherein $R^1$ is $(C_3–C_4)$cycloalkyl, phenyl or phenyl $(C_1–C_4)$alkyl, any of said previous $(C_1–C_4)$alkyl moieties optionally having from one to nine fluorines; said $(C_1–C_4)$alkyl or $(C_3–C_4)$cycloalkyl optionally mono- or di-substituted independently with hydroxy $(C_1–C_4)$alkoxy, $(C_1–C_4)$alkylthio, $(C_1–C_4)$alkylsulfinyl, $(C_1–C_4)$alkylsulfonyl; and said $(C_3–C_4)$cycloalkyl optionally having from one to seven fluorines; and $R^2$ is M and M is phenyl;

said M is optionally substituted, with up to three substituents independently selected from $R^6$, $R^7$ and $R^8$, wherein $R^6$, $R^7$ and $R^8$ are optionally a partially saturated, fully saturated, or fully unsaturated three to seven membered ring optionally having one to three heteroatoms selected independently from oxygen, sulfur and nitrogen optionally substituted with $(C_1–C_4)$alkyl, and $R^6$, $R^7$ and $R^8$ are also optionally hydroxy, nitro, halo, $(C_1–C_4)$alkoxy, $(C_1–C_4)$alkoxycarbonyl, $(C_1–C_4)$alkyl, formyl, $(C_1–C_4)$alkanoyl, $(C_1–C_4)$alkanoyloxy, $(C_1–C_4)$alkanoylamino, $(C_1–C_4)$alkoxycarbonylamino, sulfonamido, $(C_1–C_4)$alkylsulfonamido, amino, mono-N- or di-N,N-$(C_1–C_4)$alkylamino, carbamoyl, mono-N- or di-N,N-$(C_1–C_4)$alkylcarbamoyl, cyano, thiol, $(C_1-C_4)$alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines.

2. A compound as recited in claim 1 wherein the compound is

[5-cyclopropyl-1-(2-trifluoromethylphenyl)-1H-pyrazole-4-carbonyl]guanidine;

[5-cyclopropyl-1-phenyl-1H-pyrazole-4-carbonyl]guanidine; or

[5-cyclopropyl-1-(2,6-dichlorophenyl)-1H-pyrazole-4-carbonyl]guanidine or the pharmaceutically acceptable salts thereof.

3. A compound as recited in claim 1 wherein $R^2$ is 2-trifluoromethylphenyl; and $R^1$ is cyclopropyl or the pharmaceutically acceptable salts thereof.

4. A compound as recited in claim 1 wherein $R^2$ is phenyl; and $R^1$ is cyclopropyl or the pharmaceutically acceptable salts thereof.

5. A compound as recited in claim 1 wherein $R^2$ is 2,6-dichlorophenyl; and $R^1$ is cyclopropyl or the pharmaceutically acceptable salts thereof.

6. A compound as recited in claim 1 wherein $R^1$ is $(C_3-C_7)$cycloalkyl; and $R^2$ is phenyl;

said $R^2$ ring is optionally mono-substituted on carbon with a fully saturated or fully unsaturated five to six membered ring optionally having one to two heteroatoms selected independently from oxygen, sulfur and nitrogen, said ring optionally mono-substituted with $(C_1-C_4)$alkyl said $R^2$ ring is also optionally mono- or di-substituted independently on carbon with hydroxy, halo, $(C_1-C_4)$alkoxy, $(C_1-C_4)$alkoxycarbonyl, $(C_1-C_4)$alkyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl wherein said $(C_1-C_4)$alkoxy, $(C_1-C_4)$alkyl, $(C_1-C_4)$alkanoyl, $(C_1-C_4)$alkylthio, mono-N- or di-N,N-$(C_1-C_4)$alkylamino are optionally mono-substituted with hydroxy, $(C_1-C_4)$alkoxycarbonyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines or the pharmaceutically acceptable salts thereof.

* * * * *